(12) United States Patent
Sarubbi et al.

(10) Patent No.: US 8,686,154 B2
(45) Date of Patent: *Apr. 1, 2014

(54) COMPOUNDS AND COMPOSITIONS FOR DELIVERING ACTIVE AGENTS

(75) Inventors: Donald J. Sarubbi, Hartsdale, NY (US); Eugene N. Barantsevitch, Scarsdale, NY (US)

(73) Assignee: Emisphere Technologies, Inc., Roseland, NJ (US)

( * ) Notice: Subject to any disclaimer, the term of this patent is extended or adjusted under 35 U.S.C. 154(b) by 378 days.

This patent is subject to a terminal disclaimer.

(21) Appl. No.: 12/482,320

(22) Filed: Jun. 10, 2009

(65) Prior Publication Data

US 2009/0324540 A1 Dec. 31, 2009

Related U.S. Application Data

(60) Division of application No. 11/354,045, filed on Feb. 13, 2006, now Pat. No. 7,553,872, which is a division of application No. 10/395,685, filed on Mar. 24, 2003, now Pat. No. 7,071,214, which is a continuation of application No. 09/746,548, filed on Dec. 19, 2000, now abandoned, which is a division of application No. 08/796,336, filed on Feb. 7, 1997, now Pat. No. 6,358,504.

(51) Int. Cl.
*C07D 211/60* (2006.01)
*A61K 31/445* (2006.01)

(52) U.S. Cl.
USPC ...... 546/227; 424/85.2; 424/85.4; 424/141.1; 514/3; 514/12; 514/56; 514/773; 514/784; 514/788; 562/430; 562/444; 562/450; 564/15; 546/298; 546/309; 544/176; 544/295; 544/406; 548/253; 548/472; 548/476; 549/402

(58) Field of Classification Search
USPC ............ 424/85.2, 85.4, 141.1; 514/3, 12, 56, 514/773, 784, 788; 562/430, 444, 450; 564/15; 544/176, 295, 406; 546/227, 546/298, 309; 548/253, 472, 476; 549/402
See application file for complete search history.

(56) References Cited

U.S. PATENT DOCUMENTS

| | | | |
|---|---|---|---|
| 24,899 A | 7/1859 | Woodward |
| 2,671,451 A | 3/1954 | Bolger |
| 2,828,206 A | 3/1958 | Rosenberg |
| 2,862,918 A | 12/1958 | Meyer et al. |
| 2,868,740 A | 1/1959 | La Grange, III |
| 2,971,916 A | 2/1961 | Schleicher et al. |
| 3,016,308 A | 1/1962 | Macaulay |
| 3,052,655 A | 9/1962 | Fox et al. |
| 3,057,344 A | 10/1962 | Abella et al. |
| 3,076,790 A | 2/1963 | Fox et al. |
| 3,170,802 A | 2/1965 | Fukushima |
| 3,190,837 A | 6/1965 | Brynko et al. |
| 3,474,777 A | 10/1969 | Figge et al. |
| 3,491,093 A | 1/1970 | Pachter et al. |
| 3,565,559 A | 2/1971 | Sato et al. |
| 3,567,650 A | 3/1971 | Bakan |
| 3,574,832 A | 4/1971 | Engel et al. |
| 3,576,758 A | 4/1971 | Emrick |
| 3,687,926 A | 8/1972 | Arima et al. |
| 3,725,113 A | 4/1973 | Chang |
| 3,748,277 A | 7/1973 | Wagner |
| 3,794,561 A | 2/1974 | Matsukawa et al. |
| 3,795,739 A | 3/1974 | Birkmayer |
| 3,816,404 A | 6/1974 | Kablaoui et al. |
| 3,822,348 A | 7/1974 | Higashi et al. |
| 3,849,550 A | 11/1974 | Teitelbaum et al. |
| 3,933,873 A | 1/1976 | Love et al. |
| 3,937,668 A | 2/1976 | Zolle et al. |
| 3,939,253 A | 2/1976 | Bodor et al. |
| 3,956,172 A | 5/1976 | Saeki et al. |
| 3,962,416 A | 6/1976 | Katzen et al. |
| 3,976,773 A | 8/1976 | Curran et al. |
| 4,035,507 A | 7/1977 | Bodor et al. |
| 4,048,268 A | 9/1977 | Ludwig |
| 4,061,466 A | 12/1977 | Sjoholm et al. |
| 4,117,801 A | 10/1978 | Dannelly et al. |
| 4,147,767 A | 4/1979 | Yapel, Jr. |
| 4,183,849 A | 1/1980 | Hansen et al. |
| 4,199,561 A | 4/1980 | Roth et al. |
| 4,217,370 A | 8/1980 | Rawlings et al. |
| 4,238,506 A | 12/1980 | Stach et al. |
| 4,239,635 A | 12/1980 | Rieder |
| 4,239,754 A | 12/1980 | Sache et al. |
| 4,272,506 A | 6/1981 | Schwarzberg |
| 4,274,043 A | 6/1981 | Heitz |
| 4,289,759 A | 9/1981 | Heavner et al. |

(Continued)

FOREIGN PATENT DOCUMENTS

| | | |
|---|---|---|
| CA | 1077842 | 5/1980 |
| CA | 2203033 | 5/1996 |

(Continued)

OTHER PUBLICATIONS

Leone-Bay CA133:109955 (2000).*
Leone-Bay CA129:113525 (1998).*
Leone-Bay CA128:248408 (1998).*
Browne CA 70:21640 (1969).*
Fasman et al., (1964) Biochemistry, vol. 3, No. 11, pp. 1665-1674.
Fox, S W et al., (1976) BioSystems, vol. 8, pp. 40-44.
Fox, S W et al., Molecular Evolustion and the Origin of Lifem, Maxel Decker, New York (1977).
Fox S W et al., (1968) Biochem. Biophys. Acta., vol. 160, pp. 246-249.
Fox S W et al., (1976) Origins of Life, vol. 7, pp. 49-68.
Fox S.W (1980) Naturwissenschaften, vol. 67, pp. 378-383.
Fox S W et al (1960) Archives of Biochemistry and Biophysics, vol. 86, pp. 281-285.

(Continued)

*Primary Examiner* — Celia Chang
(74) *Attorney, Agent, or Firm* — Blank Rome LLP

(57) ABSTRACT

Carrier compounds and compositions therewith which are useful in the delivery of active agents are provided. Methods of administration and preparation are provided as well.

1 Claim, No Drawings

(56) References Cited

U.S. PATENT DOCUMENTS

| | | | |
|---|---|---|---|
| 4,345,588 A | 8/1982 | Widder et al. | |
| 4,348,384 A | 9/1982 | Horikoshi et al. | |
| 4,351,337 A | 9/1982 | Sidman | |
| 4,352,883 A | 10/1982 | Lim | |
| 4,357,259 A | 11/1982 | Senyei et al. | |
| 4,388,304 A | 6/1983 | Nyeki et al. | |
| 4,393,192 A | 7/1983 | Curatolo et al. | |
| 4,402,856 A | 9/1983 | Schnoring et al. | |
| 4,402,968 A | 9/1983 | Martin et al. | |
| 4,405,598 A | 9/1983 | Brown et al. | |
| 4,442,090 A | 4/1984 | Kakeya et al. | |
| 4,446,138 A | 5/1984 | Pack | |
| 4,450,150 A | 5/1984 | Sidman | |
| 4,457,907 A | 7/1984 | Porter | |
| 4,460,563 A | 7/1984 | Calanchi et al. | |
| 4,462,839 A | 7/1984 | McGinley et al. | |
| 4,462,991 A | 7/1984 | Higuchi et al. | |
| 4,473,620 A | 9/1984 | Wu et al. | |
| 4,483,807 A | 11/1984 | Asano et al. | |
| 4,492,684 A | 1/1985 | Goosen et al. | |
| 4,518,433 A | 5/1985 | McGinley et al. | |
| 4,590,265 A | 5/1986 | Bogan et al. | |
| 4,608,278 A | 8/1986 | Frank et al. | |
| 4,613,500 A | 9/1986 | Suzuki et al. | |
| 4,647,455 A | 3/1987 | De Bold et al. | |
| 4,666,641 A | 5/1987 | Fickat et al. | |
| 4,671,954 A | 6/1987 | Goldberg et al. | |
| 4,673,566 A | 6/1987 | Goosen et al. | |
| 4,683,092 A | 7/1987 | Tsang | |
| 4,690,786 A | 9/1987 | Ninomiya et al. | |
| 4,692,284 A | 9/1987 | Braden | |
| 4,692,433 A | 9/1987 | Hostetler et al. | |
| 4,703,042 A | 10/1987 | Bodor | |
| 4,708,952 A | 11/1987 | Salatinjants | |
| 4,745,161 A | 5/1988 | Saudek et al. | |
| 4,753,804 A | 6/1988 | Iaccheri et al. | |
| 4,757,007 A | 7/1988 | Satoh et al. | |
| 4,757,024 A | 7/1988 | Roper | |
| 4,757,066 A | 7/1988 | Shiokari et al. | |
| 4,766,012 A | 8/1988 | Valenti et al. | |
| 4,774,320 A | 9/1988 | Tagliabue et al. | |
| 4,789,734 A | 12/1988 | Pierschbacher | |
| 4,835,312 A | 5/1989 | Itoh et al. | |
| 4,837,381 A | 6/1989 | Steber et al. | |
| 4,844,904 A | 7/1989 | Hamaguchi et al. | |
| 4,849,222 A | 7/1989 | Broaddus | |
| 4,873,087 A | 10/1989 | Morishita et al. | |
| 4,878,942 A | 11/1989 | Motegi et al. | |
| 4,886,663 A | 12/1989 | Houghten | |
| 4,895,725 A | 1/1990 | Kantor et al. | |
| 4,897,444 A | 1/1990 | Brynes et al. | |
| 4,900,730 A | 2/1990 | Miyauchi et al. | |
| 4,908,233 A | 3/1990 | Takizawa et al. | |
| 4,919,939 A | 4/1990 | Baker | |
| 4,925,673 A | 5/1990 | Steiner et al. | |
| 4,927,928 A | 5/1990 | Shroot et al. | |
| 4,963,364 A | 10/1990 | Fox et al. | |
| 4,976,968 A | 12/1990 | Steiner | |
| 4,983,402 A | 1/1991 | Steiner | |
| 4,996,292 A | 2/1991 | Fox et al. | |
| 5,019,400 A | 5/1991 | Gombotz et al. | |
| 5,023,374 A | 6/1991 | Simon et al. | |
| 5,039,481 A | 8/1991 | Pacifici et al. | |
| 5,041,291 A | 8/1991 | Bader et al. | |
| 5,055,300 A | 10/1991 | Gupta | |
| 5,066,487 A | 11/1991 | Morelle et al. | |
| 5,067,961 A | 11/1991 | Kelman et al. | |
| 5,069,936 A | 12/1991 | Yen | |
| 5,077,278 A | 12/1991 | Hafner et al. | |
| 5,100,918 A | 3/1992 | Sunshine et al. | |
| 5,122,367 A | 6/1992 | Ron et al. | |
| 5,126,147 A | 6/1992 | Silvestri et al. | |
| 5,137,892 A | 8/1992 | Chu et al. | |
| 5,186,947 A | 2/1993 | Goettsche et al. | |
| 5,204,099 A | 4/1993 | Barbier et al. | |
| 5,206,384 A | 4/1993 | Shibahara et al. | |
| 5,216,124 A | 6/1993 | Hansen, Jr. et al. | |
| 5,244,653 A | 9/1993 | Berke et al. | |
| 5,250,236 A | 10/1993 | Gasco et al. | |
| 5,271,934 A | 12/1993 | Goldberg et al. | |
| 5,271,961 A | 12/1993 | Mathiowitz et al. | |
| 5,278,148 A | 1/1994 | Branca et al. | |
| 5,310,535 A | 5/1994 | Kruper, Jr. et al. | |
| 5,328,992 A | 7/1994 | Peter et al. | |
| 5,352,461 A | 10/1994 | Feldstein et al. | |
| 5,384,133 A | 1/1995 | Boyes et al. | |
| 5,389,377 A | 2/1995 | Chagnon et al. | |
| 5,389,379 A | 2/1995 | Dirix et al. | |
| 5,401,516 A | 3/1995 | Milstein et al. | |
| 5,418,010 A | 5/1995 | Janda et al. | |
| 5,439,686 A | 8/1995 | Desai et al. | |
| 5,443,841 A | 8/1995 | Milstein et al. | |
| 5,447,728 A | 9/1995 | Milstein et al. | |
| 5,451,410 A | 9/1995 | Milstein et al. | |
| 5,474,997 A | 12/1995 | Gray et al. | |
| 5,536,813 A | 7/1996 | Charpenel et al. | |
| 5,540,939 A | 7/1996 | Milstein et al. | |
| 5,541,155 A | 7/1996 | Leone-Bay et al. | |
| 5,578,323 A | 11/1996 | Milstein et al. | |
| 5,583,020 A | 12/1996 | Sullivan | |
| 5,601,846 A | 2/1997 | Milstein et al. | |
| 5,629,020 A | 5/1997 | Leone-Bay et al. | |
| 5,643,957 A | 7/1997 | Leone-Bay et al. | |
| 5,650,386 A | 7/1997 | Leone-Bay et al. | |
| 5,665,700 A | 9/1997 | Cho et al. | |
| 5,693,338 A | 12/1997 | Milstein | |
| 5,705,529 A | 1/1998 | Matyus et al. | |
| 5,709,861 A | 1/1998 | Santiago et al. | |
| 5,714,167 A | 2/1998 | Milstein et al. | |
| 5,750,147 A | 5/1998 | Kantor | |
| 5,766,633 A | 6/1998 | Milstein et al. | |
| 5,773,647 A * | 6/1998 | Leone-Bay et al. | 562/444 |
| 5,776,888 A * | 7/1998 | Leone-Bay et al. | 514/2 |
| 5,792,451 A | 8/1998 | Sarubbi et al. | |
| 5,804,688 A * | 9/1998 | Leone-Bay et al. | 562/444 |
| 5,811,127 A | 9/1998 | Milstein et al. | |
| 5,820,881 A | 10/1998 | Milstein | |
| 5,824,345 A | 10/1998 | Milstein | |
| 5,840,340 A | 11/1998 | Milstein et al. | |
| 5,863,944 A * | 1/1999 | Leone-Bay et al. | 514/559 |
| 5,866,536 A * | 2/1999 | Leone-Bay et al. | 514/2 |
| 5,876,710 A | 3/1999 | Leone-Bay et al. | |
| 5,879,681 A | 3/1999 | Leone-Bay et al. | |
| 5,935,601 A | 8/1999 | Leone-Bay et al. | |
| 5,939,381 A * | 8/1999 | Leone-Bay et al. | 514/2 |
| 5,955,503 A | 9/1999 | Leone-Bay et al. | |
| 5,958,457 A | 9/1999 | Santiago et al. | |
| 5,962,710 A | 10/1999 | Gschneidner et al. | |
| 5,965,121 A * | 10/1999 | Leone-Bay et al. | 424/85.2 |
| 5,972,387 A | 10/1999 | Milstein et al. | |
| 5,976,569 A | 11/1999 | Milstein | |
| 5,989,539 A | 11/1999 | Leone-Bay et al. | |
| 5,990,166 A * | 11/1999 | Leone-Bay et al. | 514/563 |
| 6,001,347 A * | 12/1999 | Leone-Bay et al. | 424/85.1 |
| 6,011,000 A | 1/2000 | Perrine et al. | |
| 6,051,258 A | 4/2000 | Kantor | |
| 6,051,561 A * | 4/2000 | Leone-Bay et al. | 514/56 |
| 6,060,513 A * | 5/2000 | Leone-Bay et al. | 514/559 |
| 6,071,510 A | 6/2000 | Leone-Bay et al. | |
| 6,071,538 A | 6/2000 | Milstein et al. | |
| 6,084,112 A | 7/2000 | Ho et al. | |
| 6,090,958 A * | 7/2000 | Leone-Bay et al. | 554/112 |
| 6,099,856 A | 8/2000 | Milstein et al. | |
| 6,100,285 A | 8/2000 | Kantor | |
| 6,100,298 A | 8/2000 | Leone-Bay et al. | |
| 6,194,193 B1 | 2/2001 | Drahos et al. | |
| 6,242,495 B1 * | 6/2001 | Leone-Bay et al. | 514/617 |
| 6,313,088 B1 * | 11/2001 | Leone-Bay et al. | 514/2 |
| 6,346,242 B1 * | 2/2002 | Leone-Bay et al. | 424/85.1 |
| 6,358,504 B1 * | 3/2002 | Leone-Bay et al. | 424/85.1 |
| 6,358,508 B1 | 3/2002 | Ni et al. | |
| 6,428,780 B2 * | 8/2002 | Leone-Bay et al. | 424/85.1 |
| 6,440,929 B1 * | 8/2002 | Milstein et al. | 514/2 |
| 6,693,073 B2 * | 2/2004 | Milstein et al. | 514/3 |

(56) References Cited

U.S. PATENT DOCUMENTS

| | | | |
|---|---|---|---|
| 6,991,798 B1 * | 1/2006 | Gschneidner et al. | 424/400 |
| 7,067,119 B2 * | 6/2006 | Leone-Bay et al. | 424/85.2 |
| 7,071,214 B2 * | 7/2006 | Sarubbi et al. | 514/323 |
| 7,125,910 B2 * | 10/2006 | Leone-Bay et al. | 514/570 |
| 7,186,414 B2 * | 3/2007 | Gschneidner et al. | 424/400 |
| 7,309,698 B2 * | 12/2007 | Boyd et al. | 514/102 |
| 7,351,741 B2 * | 4/2008 | Weidner et al. | 514/557 |
| 7,417,022 B2 * | 8/2008 | Leone-Bay et al. | 514/559 |
| 7,429,564 B2 * | 9/2008 | Arbit et al. | 514/4 |
| 7,495,030 B2 * | 2/2009 | Gschneidner | 514/557 |
| 7,553,872 B2 * | 6/2009 | Sarubbi et al. | 514/563 |
| 7,744,910 B2 * | 6/2010 | Gschneidner et al. | 424/400 |

FOREIGN PATENT DOCUMENTS

| | | |
|---|---|---|
| CA | 2214323 | 10/1996 |
| CN | 1099558 | 3/1995 |
| DE | 2424169 | 12/1974 |
| DE | 2343037 | 3/1975 |
| DE | 3202255 | 10/1982 |
| EH | 9747270 | 12/1997 |
| EP | 0000667 | 2/1979 |
| EP | 0036145 | 9/1981 |
| EP | 0068314 | 1/1983 |
| EP | 0105804 | 4/1984 |
| EP | 130162 | 1/1985 |
| EP | 170540 | 2/1986 |
| EP | 226223 | 6/1987 |
| EP | 342054 | 11/1989 |
| EP | 342056 | 11/1989 |
| EP | 365183 | 4/1990 |
| EP | 366277 | 5/1990 |
| EP | 418642 | 3/1991 |
| EP | 448057 | 9/1991 |
| EP | 452161 | 10/1991 |
| EP | 459795 | 12/1991 |
| EP | 467389 | 1/1992 |
| EP | 0477912 | 4/1992 |
| EP | 490549 | 6/1992 |
| EP | 517211 | 12/1992 |
| EP | 0576941 | 1/1994 |
| EP | 616799 | 9/1994 |
| ES | 369853 A1 | 7/1971 |
| FR | 1351358 | 2/1964 |
| FR | 1468601 | 2/1967 |
| FR | 2133926 | 12/1972 |
| FR | 2326934 | 5/1977 |
| FR | 2565102 | 12/1985 |
| GB | 929401 | 6/1963 |
| GB | 1075952 | 7/1967 |
| GB | 1236885 | 6/1971 |
| GB | 1484848 | 9/1977 |
| GB | 1567763 | 5/1980 |
| GB | 2095994 | 10/1982 |
| IL | 71258/2 | 12/1987 |
| JP | 48-24246 | 3/1973 |
| JP | 51-136646 | 11/1976 |
| JP | 56-68612 | 6/1981 |
| JP | 58-35111 | 3/1983 |
| JP | 2239980 | 9/1990 |
| JP | 5168469 | 7/1993 |
| JP | 6107682 | 4/1994 |
| JP | 06-239822 | 8/1994 |
| NL | 280825 | 12/1964 |
| NL | 280826 | 12/1964 |
| NO | B-146698 | 11/1982 |
| WO | WO-8500105 | 1/1985 |
| WO | WO-8500110 | 1/1985 |
| WO | WO-8500809 | 2/1985 |
| WO | WO-8502772 | 7/1985 |
| WO | WO-87/04076 | 7/1987 |
| WO | WO-8704076 | 7/1987 |
| WO | WO-8801213 | 2/1988 |
| WO | WO-9219263 | 11/1992 |
| WO | WO-9318754 | 9/1993 |
| WO | WO-9325583 | 12/1993 |
| WO | WO-9411015 | 5/1994 |
| WO | WO-9414420 | 7/1994 |
| WO | WO-9418950 | 9/1994 |
| WO | WO-9418997 | 9/1994 |
| WO | WO-9421234 | 9/1994 |
| WO | WO-9423702 | 10/1994 |
| WO | WO-9423767 | 10/1994 |
| WO | WO-9424291 | 10/1994 |
| WO | WO-9428878 | 12/1994 |
| WO | WO-9511690 | 5/1995 |
| WO | WO-9528838 | 11/1995 |
| WO | WO-9528920 | 11/1995 |
| WO | WO-9609813 | 4/1996 |
| WO | WO-9610396 | 4/1996 |
| WO | WO-9612473 | 5/1996 |
| WO | WO-9612474 | 5/1996 |
| WO | WO-9612475 | 5/1996 |
| WO | WO-9621464 | 7/1996 |
| WO | WO-96/30036 | 10/1996 |
| WO | WO-9630036 | 10/1996 |
| WO | WO-9633699 | 10/1996 |
| WO | WO-9639835 | 12/1996 |
| WO | WO-9640070 | 12/1996 |
| WO | WO-9640076 | 12/1996 |
| WO | WO-9710197 | 3/1997 |
| WO | WO-9731938 | 9/1997 |
| WO | WO-9736480 | 10/1997 |
| WO | WO-9747288 | 12/1997 |
| WO | WO-9825589 | 6/1998 |
| WO | WO-9834632 | 8/1998 |
| WO | WO-9849135 | 11/1998 |
| WO | WO-9850341 | 11/1998 |
| WO | WO-9916427 | 4/1999 |
| WO | WO-0006184 | 2/2000 |
| WO | WO-0006534 | 2/2000 |
| WO | WO-0007979 | 2/2000 |
| WO | WO-0040203 | 7/2000 |
| WO | WO-0046182 | 8/2000 |
| WO | WO-0047188 | 8/2000 |
| WO | WO-0048589 | 8/2000 |
| WO | WO-0050386 | 8/2000 |
| WO | WO-0059480 | 10/2000 |
| WO | WO-0059863 | 10/2000 |

OTHER PUBLICATIONS

Fox S W et al., (1974) Origins of Life, vol. 5, pp. 227-237.
Fox S W et al., (1984) Origins of Life vol. 14, pp. 485-488.
Gol'dovskii, A M (1978) Zhurnal Evolyutsionnoi Biokhimii I Fiziologii vol. 14(6), pp. 437-439.
Gurrieri S et al., (1973) Thermochimica Acta, vol. 7, pp. 231-239.
Harada K, et al., (1979) Biosystems, vol. 11, pp. 47-53.
Harada et al., (1960) Archives of Biochemistry and Biophysics, vol. 86, pp. 274-280.
Hare (1970) Etude Cenetique De La Polycondensation Thermique D' x-Amino Acides, vol. 45, pp. 330-339.
Heinrich M R et al., (1969) Archives of Biochemistry and Biophysics vol. 130, pp. 441-448.
Heinz B et al., (1981) Biosystems vol. 14, pp. 33-40.
Hennon G et al., (1975) Biochimie, vol. 57, pp. 1395-1396.
Hsu L L et al., (1976) Biosystems, vol. 8 pp. 89-101.
Hsu L L et al., (1971) Currents in Modern Biology, vol. 4, pp. 12-25.
Ishima Y et al (1981) Biosystems, vol. 14, pp. 243-251.
Jackson et al., (1991) "Pharmacological . . . " J Pharm. & Exp Thera., vol. 261. No. 1, pp. 546-552.
Jungck J R et al., (1973) Naturwissenschaften, vol. 60, pp. 425-427.
Kokufuta E et al., (1984) Biosystems, vol. 16, pp. 175-181.
Krampitz G et al., (1967) Naturwissenschaften pp. 516-517.
Krampitz G et al. (1968) Naturwissenschaften pp. 345-346.
Krampitz G et al. (1966) Naturwissenschaften pp. 7-8.
Lacey Jr. J C et al., (1979) Biosystems vol. 11, pp. 9-17.
Lacey Jr. J C et al., (1979) Biosystems vol. 11, pp. 1-7.
Martinez Luque-Romero M et al., (1986) BioSystems, vol. 19, pp. 267-272.
Masinovsky Z et al., (1989) Biosystems, vol. 22, pp. 305-310.

(56) References Cited

OTHER PUBLICATIONS

Matsuno K (1982) Biosystems vol. 15, pp. 1-11.
Matsuno K (1984) Biosystems vol. 17, pp. 11-14.
Matsuno K (1981) Biosystems col. 14, pp. 163-170.
McAlhaney W W et al., (1976) BioSystems, vol. 8, pp. 45-40.
Melius P et al., (1987) BioSystems, vol. 20, pp. 213-217.
Melius P et al., (1975) Bioorganic Chemistry, vol. 4, pp. 385-391.
Melius P et al., (1979) Biosystems, vol. 11, pp. 125-132.
Miquel J et al., (1971) Currents in Modern Biology, vol. 3, pp. 299-306.
Nakashima T et al., (1980) J Mol Evol, vol. 15, pp. 161-168.
Nakashima T et al., (1981) Biosystems, vol. 14, pp. 151-161.
Novak, V. J. A. (1984) Origins of Life, vol. 14, pp. 513-522.
Olafsson P G et al., (1971) Polymer Letters, vol. 9, pp. 521-528.
Phillips, R. D. et al., (1974) Int. J. Peptide Protein Res., vol. 6, pp. 309-319.
Przybylski A T et al., (1982) Die Naturwissenschaften, vol. 69, pp. 561-563.
Przybylski A T et al., (1984) Applied Biochemistry and Biotechnology, vol. 10, pp. 301-307.
Przybylski A T et al., (1985) BioSystems, vol. 17, pp. 281-288.
Rohlfing D L (1975) Origins of Life, vol. 6, pp. 203-209.
Rohlfing D L (1970) Science, vol. 169, pp. 998-1000.
Rohlfing D L (1967) Archives of Biochemistry and Biophysics, vol. 118, pp. 468-474.
Rohlfing D L (1969) Catalytic Activities of Thermal Polyanhydro-alpha-Amino Acids, pp. 373-418.
Rohlfing D L (1976) Biosystems, vol. 8, pp. 139-145.
Ryan J W et al., (1973) Biosystems vol. 5, pp. 115-118.
Saunders M A et al., (1974) Biosystems vol. 6, pp. 81-92.
Snyder W D et al., (1975) Biosystems, vol. 7, pp. 222-229.
Sokol P E (1974) Journal of the American Oil Chemists' Society, vol. 52, pp. 101-102.
Tschager et al., (1988) Milchwirtschaftliche Berichte, vol. 95, pp. 79-83.
Vaughan G et al., (1987) Biosystems, vol. 20, pp. 219-223.
Vol'kenshtein M V et al.,(1989) Molekulyarnaya Biologiya, vol. 23(1), pp. 23-37.
Waehneldt T V et al., (1968) Biochim. Biophys. Acta. vol. 160 pp. 239-245.
Williams et al., (1999) J Biol. Chem., vol. 266, No. 8, pp. 5182-5190.
Yuki A et al., (1969) Biochemical and biophysical research communications, vol. 36(4), pp. 657-663.
Zulaski et al., (1983) New Carboxyalkyl Inhibitors of Brain Enkenphalinase, J Med. Chem., 26, pp. 60-65.
Chemical Abstract vol. No. 105(1), (1985) No. 12027p.
Chemical Abstract vol. No. 102(6) (1985) No. 50870d.
Chemical Abstract vol. No. 80(9) No. 52392a.
Bergeron Raymond J et al., (1994) Macromolecular Self-Assembly of Diketopiperazine Tetrapeptides Journal of the American Chemical Society, vol. 116, pp. 8479-8484.
Bergeron Raymond J et al., (1993) A Comparative Study of the ironclearing properties of desferrithiocin analogues with desferrioxamine B in a cebus monkey model, Blood, vol. 81, No. 8, pp. 2166-2173.
Bergeron Raymond J et al., (1992) A Comparison of the Iron-clearing Properties of 1,2-dimethyl-3-hydroxypyrid-4-one, 1,2-diethyl-3-hydroxypyrid-4-one, and deferoxamine Blood, vol. 79, No. 7, pahes 1882-1890.
Bergeron Raymond J et al., (1991) Evaluation of Desferrithiocin and its synthetic analogs as orally effective iron chelators, Journal of Medicinal chemistry, vol .34, No. 7, pp. 2072-2078.
Bergeron Raymond J et al., (1990) A comparative evaluation of Iron Clearance models, Annals New York Academy of Science, pp. 278-293. Mar. 13-15.
Andriuoli G et al., (1990) Haemostasis 20(suppl.1) 154-158.
Caramazza I et al., (1991) Thrombosis Research 62:785-789.
Guarini S et al., (1983) Experimentia 41:350-352.
Guarini S et al., (1985) Pharmacological Research Communications 17(8):685-697.

Dal Pozzo A et al., (1989) Thrombosis Research 56:119-124.
Gelb R et al., (1983) Lite Sciences 33(1):83-85.
Watterberg et al., (1988) Pediatric Research vol. 23. No. 4, part 2, p. 570A, col. 1, abstract No. 2209.
Bernstein (1985) Chest 87(1):68S-73S.
Darnge et al., (1988) Diabetes 37:246-251.
Chemical Abstracts (1975) 83:184360k.
Amino Y et al., Chem Pharm Bull. 36(11):4426-4434.
Baughman, R.A. et al., Proc. of the 6th Inter'l. Symp. on Recent Advs. in Drug Delivery Systems, Ctr. for Controlled Chern. Delivery, University of Utah, Feb. 22-25, 1993, Salt Lake City, UT, pp. 179-180 "Method for Assessing The Stability of Proteinoid Microspheres".
Haas, S. et al., "Assessment Of Stability Of Proteinoid Microspheres", Proceed. Intern. Symp. Control. Rel. Bioact. Mater., 20 (1993),Controlled Release Society, Inc.
X. Ma, et al., Proceed. Intern. Symp. Control. Rel. Bioact. Mater., 20 (1993), Cop-trolled Release Society, Inc. "In Vitro Mechanistic Investi.e;ation of the Proteinoid Microsphere Oral Delivery System".
Yen, H.-R H., et al., "Adsorption of Sulforhodamine 101 on Proteinoid Microspheres" Proceed. Intern. Symp. Control. Rel. Bioart. Mater., 20 (1993), Controlled Release Society, Inc.
Presented at "IBC Rational Drug Design Conference", San Diego, Calif. -Dec. 1994.
Leone-Bay et al., Presented at "Winter Conference on Medicinal and Bioorganic Chemistry" Steamboat Springs, Colorado—Feb. 1995 "Microsphere Formation and Drug Delivery in a Series of Derivatized Amino Acids".
Santiago et al., Pharm. Res. 11: 1994, p. S-298 "Oral Delivery of Heparin Microspheres made with Modified Amino Acids".
Leone-Bay et al., Pharm. Res. 11: 1994, p. S-121 "Oral Delivery of Heparin using Acylated Amino Acids".
Sarubbi et al., Pharm. Res. 11: 1994, p. S-299 "Oral Calcitonin Delivery using the PODDS Technology".
Leipold et al., Pharm. Res. 11: 1994, p. S-298 Oral Delivery of Interferon in Rats and Primates II.
Santiago et al., Pharm. Res. 11: 1994, p. S-298 "Evaluation in Rats of Vehicles for the Oral Delivery of Low Molecular Weight Heparin".
X. Ma et al., PDD 7303 Pharmaceutical Research .2(1O):S-244, 1992 (October Supplement).
Milstein et al., Symposia Abstracts. AAPS Annual Meeting, San Antonia, TX, Nov. 15-19, 1993.
Santiago et al. "Initial Studies In The Assessment of Proteinoid Microsphere Activity" Proceed. Intern. Symp. Control. Rel. Biaaet. Mater., 20 (1993), Controlled Release Society, Inc.
Santiago et at. Oral Inununization of Rats with Influenza Virus M Protein (M1) Microspheres II Proceed. Intern. Symp. Control. Rel. Biaaet. Mater., 19 (1992), Controlled Release Society, Inc., p. 116-117.
Santiago et al. ,"Proteinoid Microspheres For The Oral Delivery of Heparin" Proceed. Intern. Symp. Control. Rei. Bioact. Mater 19 (1992), Controlled Release Society, Inc. p. 514-515.
Santiago et al. American Society for Microbiology 92nd General Meeting, Abstract of the General Meeting, p. 159, May 26-30, 1992.
Milstein et at. "Preparation And In Vitro Characterization Of Proteinoid Microspheres" Proceed Intern. Symp. Control. Rel. Bioact. Mater., 19 (1992), Controlled Release Society, Inc. p. 516-517.
Doris K. Chiappetta, Eastern Analytical Symposium, Nov. 17, 1992 "Solutions for Problems in Bioanalysis".
Elizabeth A. Harris. M.S., Eastern Analytical Symposium, Nov. 17, 1992 Solutions for Problems in Bioanalysis.
AAPS 6TH Ann. Meeting and Expo. ,"Proteinoids—A Novel Drug Delivery System" Nov. 19 1992,p. 33.
Milstein et al., "Efficient Oral Delivery Of Monoclonal Antibodies By Proteinoid Encapsulation" The 1993 Miami Bio/Technology Winter Symposium—Advances in Gene Technology: Protein Engineering and Beyond, Jan. 17-22. 1993.
Xinghang Ma, et al. "Stability Study of Drug-loaded Proteinoid Microsphere Formulations during Freeze-drying" Journal of Drug Targeting, 1994, vol. 2, pp. 9-21.

(56) References Cited

OTHER PUBLICATIONS

Bauglunan et al., "Screening Candidate Microsphere Formulations By Incubating In Simulated Digestive Fluids". Proc. ofthe 6th InternSympo. on Recent Advances in Drug Delivery Systems, Ctr. for Controlled Chern. Delivery, University of Utah, Feb. 22-25, 1993, pp. 181-182.
Robert O. Dillman, M.D., Annals of Internal Medicine 1989: 111 pp. 592-600, "Monoclonal Antibodies for Treating Cancer".
Brendan D. Curti, Critical Reviews in Oncology/Hematology, 1993: 14 pp. 29-39 "Physical barriers to drug delivery in tumors".
V. Hird et al, Genes and Cancer, edited by Desmond Carney & Karol Sikora, pp. 183-189, Immunotherapy with Monoclonal Antibodies. 1990.
Michael E. Osband et al., Immunology Today, Vol11, No. 6 1990, pp. 193-195, "Problems in the investigational study and clinical use of cancer inununotherapy".
William J. Harris, Tibtech Feb. 1993 vol. II, pp. 42-44 "Therapeutic antibodies—the cominJ:!; of aJ:!;e".
Thomas A. Waldmann, Science, Jun. 21, 1991. 252:1657-1662, "Monoclonal Antibodies in Diagnosis and Therapy".
Chemical Abstracts, 76(14):72994u, (1971).
Chemical Abstracts, 84(7):44660d. (1975).
Chemical Abstracts. 86(16):107529g, (1976).
Chemical Abstracts, 112(15): 134663h, (1989).
Chemical Abstracts, 114(22):214519x, (1990).
J. Gyore et at., Thermal Analysis, vol. 2—Proceeding Fourth ICTA Budaoest 1974 0.387-394.
Chemical Abstracts, 99(19) 158832b, (1982).
Derwent Abstracts, IP 67008622, (1967).
Journal of Medicinal Chemistry, vol. 38, No. 21, pp. 4257-4262, (1995), "Microsphere Formation in a Series of Derivatized a-Amino Acids: Properties, Molecular Modeling, and Oral Delivery of Salmon Calcitonin".
Andrea Leone-Bay et al., Journal of Medicinal Chemistry, vol. 38, No. 21, pp. 4263-4269, (1995), "N-Acylated a-Amino Acids as Novel Oral Delivery Agents for Proteins".
The Extra Pharmacopoeia, Thirtieth Edition, pp. 325-326, (1993).
Stephen L. Douglas et al., Chemistry and Industry, vol. 22:748-751, 1985.
C.A. Finch, Chemistry and Industry, vol. 22:752-756, 1985.
John A. Butera et al., J. Med. Chern., vol. 34:3212~3228, 1990.
Madeline G. Cimini et al., Ann. Report in Med Chern., Vol. 27:89-98.,1992.
Bernadette Earley et al., Brain Research, vol. 546:282-286, 1991.
John W. Ellingboe et al., J. Med Chern., vol. 35:705-716, 1992.
William C. Lumma et a!., J. Med Chern., vol. 30:755-758, 1987.
Joseph J. Lynch et al., J. of Pharm. and Exp. Therap., vol. 269:541-554, 1994.
Kiyoshi Matsuno et al., Brain Research, vol. 575:315-319, 1992.
Thomas K. Morgan et al., J. Med. Chern., vol. 33:1091-1097, 1990.
Hitoshi Oinuma et al., J. Med Chern., vol. 33:903-905, 1990.
Tadimeti S. Rao et al., Molecular Pharmacology, vol. 37:978-982, 1990.
Asaji Kondo, Microcapsule Processing and Technology. pp. 154-165, 1979.
G. Pastores et al., J. Liquid Chromatopgraphy, 18(15):3049-3059, 1995.
D. Sinha et al. J. Bio. Chern.. 260(19):10714-10719. 1985.
E. Franssen et a!., J. Med. Chern . 35: 1246-1259, 1992.
Chemical Abstracts, 99(23): 191473h, Dec. 5, 1983.
R. Langer, Science, 249:1527-1533,Sep. 28, 1990.
M. Alonso et al., Vaccine, 12:299, 1994.
A. Leone-Bay et al., J. Med. Chern., 39:2571-2578, 1996.
R. Thompson, Biochemistry, 12:47-51, 1973.
S.Thompson, J. Med. Chern., abstract, 86:174780, 1986.
Leone-Bay et al., DRURS of the Future, 22(8):885-891, 1997.
Leone-Bay et al., J Med Chem., 41(7):1163-1171 (1998).
G. Picciola, II Farmaco, 31:655-664 (1976).
Tanaka et al., Biophysical Chemistry, vol. 50 (1994) 47-61.
Degrado et al., Science, vol. 243, (1989) 622-628.
Lynee Regan et a!., Science, vol. 241 (1988), 976-978.
Matouschek et al., Nature, vol. 340, (1989) 122-126.
Parker et a!., Peptide Research 347, vol. 4, No. 6 (1991).
Parker et a!., Peptide Research 355, vol. 4, No. 6 (1991).
Fedorov et al., J. Mol. Biol. (1992) 225,927-931.
Ptitsyn et al., Biopolymers, Yol. 22, 15-25 (1983) 15-25.
Ptitsyn et a!., Protein Engineering vol. 2, No. 6 I 443-447, 1989.
J. M. Lehn, Makromol. Chern., Macromol. Symp. (1993) vol. 69, 1-17.
Paolo Scrimin, Chemistry Chimicaoggi (1989).
J.M. Lehn, Angew. Chern. Int. Ed. Eng!. 27 (1988) 89-112.
Chemical Abstracts Registry No. 70204-54-5.
Chemical Abstracts Registry No. 73548-12-6.
Alder et al., "Introduction of probability and statistics" Fremman Co, p. 156-157.
European Search Report dated Feb. 28, 2001 for European Patent Application No. 00122704.0.
Greenfeld et al., "Antiinflammator" CA 74;12838 (1971).
Mase et al., "Preparation of phenylene" CA 107:39428 (1987).
Gachbeudber et al., "Preparation of arylamindoalkylcarboxylic acid" CA 132:151567 (2000).
Suling et al., "Increased mutagnicity of chloroethylniytosoureas in the presence of a rat liver S9 microsome mixture" CA 98:211346 (1983).
Kappas et al., "Genotoxic activity of plant growth regulating hormones". CA 100:81016 (1983).
Schoebel et al., Synthesis and confomation of the pentapeptide CA 76:137103 (1975).
Losert et al., "Effect of indole-e-akanecarbonylic acid" CA 83:157934 (1975).
Badenoch-jones et al., "Phytohormones" CA 101:147905 (1984).
Stacey et al., "Pentasaccharide phytohormones" CA 121:104372 (1994).
Chemical Abstracts Registry No. 19878-22-9, (1968).
Chemical Abstracts Registry No. 108179-99-3, (1986).
Chemical abstracts registry No. 101732-48-3, (1959).
Chemical abstracts registry No. 183990-59-2, (1996).
Chemical abstracts registry No. 487-54-7, (1980).
Chemical abstracts registry No. 156806-79-0, (1994).
Chemical abstracts registry No. 21084-57-1, (1968).
Chemical abstracts registry No. 78121-44-5, (1979).
Chemical abstracts registry No. 35197-20-7, (1972).
Brown, G and Foubister, A. J., J Med Chem. 27:79-81, (1984).
Suling et al,. JNCI 70(4): 767-769, (Apr. 1983).
Airaudo, C.B et al., (1987) Journal of Food Science, vol. 52(6), pp. 1750-1752.
Andini, S, et al., (1975) Origins of Life, vol. 6, pp. 147-153.
Brooke S et al., (1977) Biosystems, vol. 9, pp. 1-22.
Chen et al., (1975) "Evidence for Hemiacetal Formation" Biochemistry vol. 18, No. 5, pp. 921-925.
Davis et al., (1983) "Leucinal Inhibits . . . ", Pharmacology Biochemistry Behavior, vol. 19, pp. 791-794.
Dose K (1974) Origins of Life, vol. 5, pp. 239-252.

\* cited by examiner

COMPOUNDS AND COMPOSITIONS FOR DELIVERING ACTIVE AGENTS

This application is a divisional of prior application Ser. No. 11/354,045, filed Feb. 13, 2006 now U.S. Pat. No. 7,553,872 which is a divisional of application Ser. No. 10/395,685 now U.S. Pat. No. 7,071,214, filed Mar. 24, 2003, which is a continuation of application Ser. No. 09/746,548, filed Dec. 19, 2000 now abandoned, which is a divisional of prior application Ser. No. 08/796,336, filed Feb. 7, 1997 now U.S. Pat. No. 6,358,504. Each of these prior filed applications are hereby incorporated by reference in their entirety.

FIELD OF THE INVENTION

The present invention relates to compounds for delivering active agents, and particularly biologically or chemically active agents. These compounds are used as carriers to facilitate the delivery of a cargo to a target. The carrier compounds are well suited to form non-covalent mixtures with biologically-active agents for oral administration to animals. Methods for the preparation administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers.

For example in the delivery to animals of biologically active or chemically active pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastro-intestinal (GI) tract, powerful digestive enzymes, and active agent impermeable gastro-intestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargoes, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents.

SUMMARY OF THE INVENTION

Compounds and compositions which are useful in the delivery of active agents are provided. These compositions include at least one active agent, preferably a biologically or chemically active agent, and at least one of the following compounds 1-193, or salts thereof.

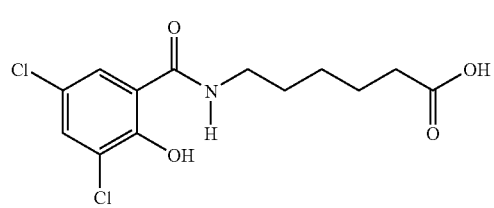

6-N-(3,5-dichloro-2-hydroxybenzoyl) aminocaproic acid

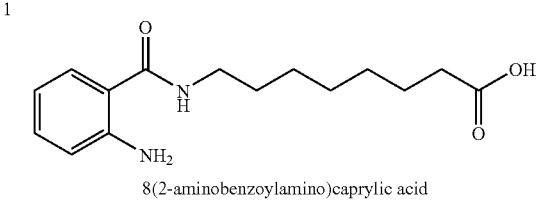

8(2-aminobenzoylamino)caprylic acid

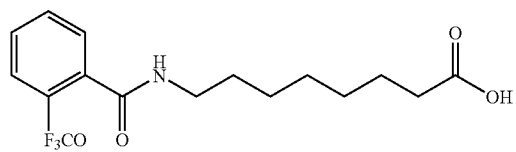

8(2-trifluoromethoxy)benzoylamino caprylic acid

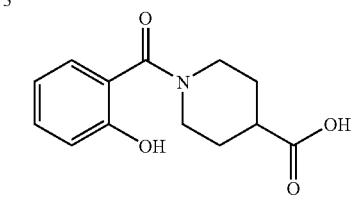

N-(2-hydroxybenzoyl)isonipecotic acid

-continued

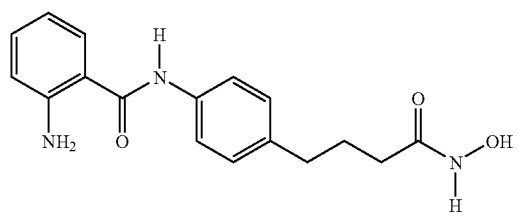
4-[4-(2-aminobenzoylamino)phenyl]butyrylhydroxamic acid

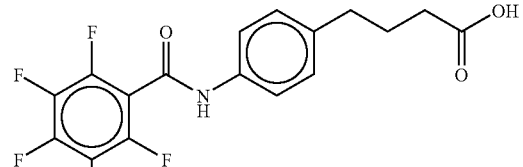
4-(4-(pentafluorobenzoyl)aminophenyl)butyric acid

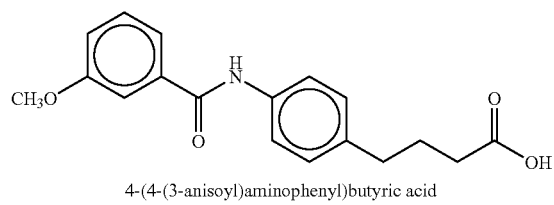
4-(4-(3-anisoyl)aminophenyl)butyric acid

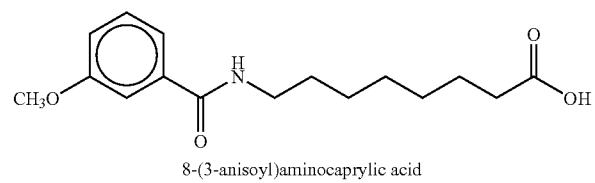
8-(3-anisoyl)aminocaprylic acid

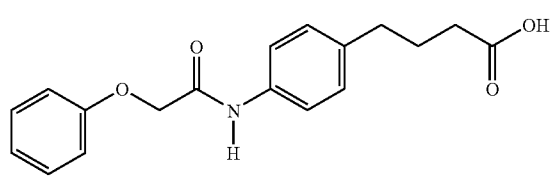
4-(4-(phenoxyacetyl)aminophenyl)butyric acid

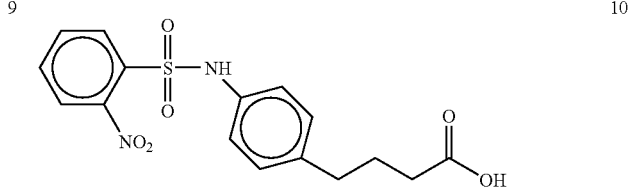
4-(4-(2-nitrobenzenesulfonyl)aminophenyl)butyric acid

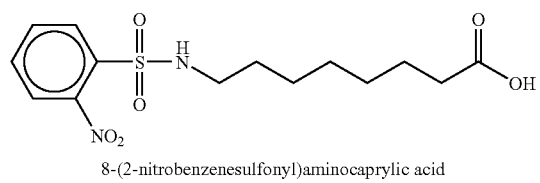
8-(2-nitrobenzenesulfonyl)aminocaprylic acid

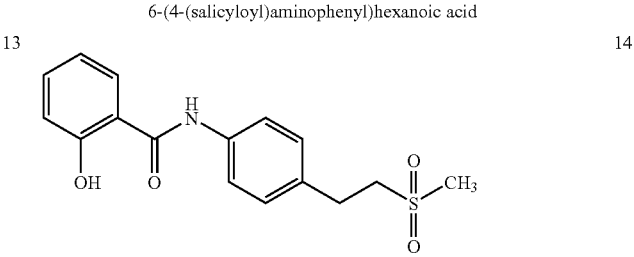
6-(4-(salicyloyl)aminophenyl)hexanoic acid

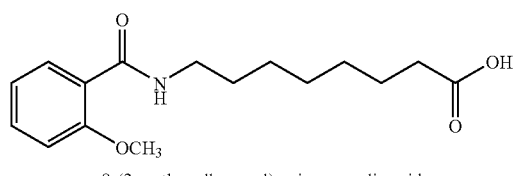
8-(2-methoxylbenzoyl)amino caprylic acid

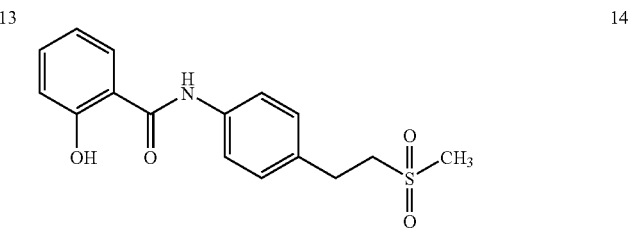
2-[4-(Salicyloylamino)phenyl]ethyl methyl sulfone

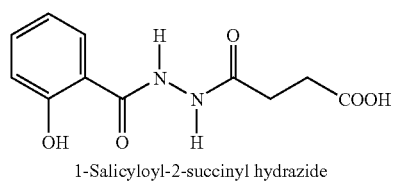
1-Salicyloyl-2-succinyl hydrazide

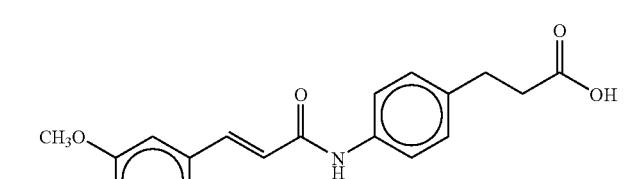
3-(4-(2,5-dimethoxycinnamoyl)aminophenyl)propionic acid

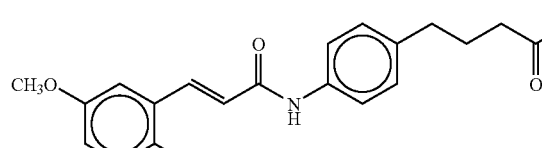
4-(4-(2,5-dimethoxycinnamoyl)aminophenyl)butyric acid

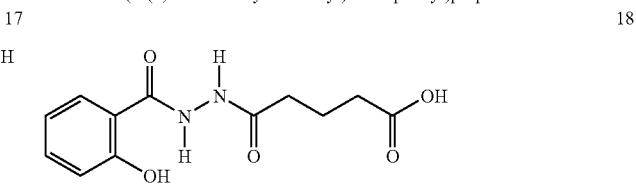
1-salicyloyl-2-glutaryl hydrazide

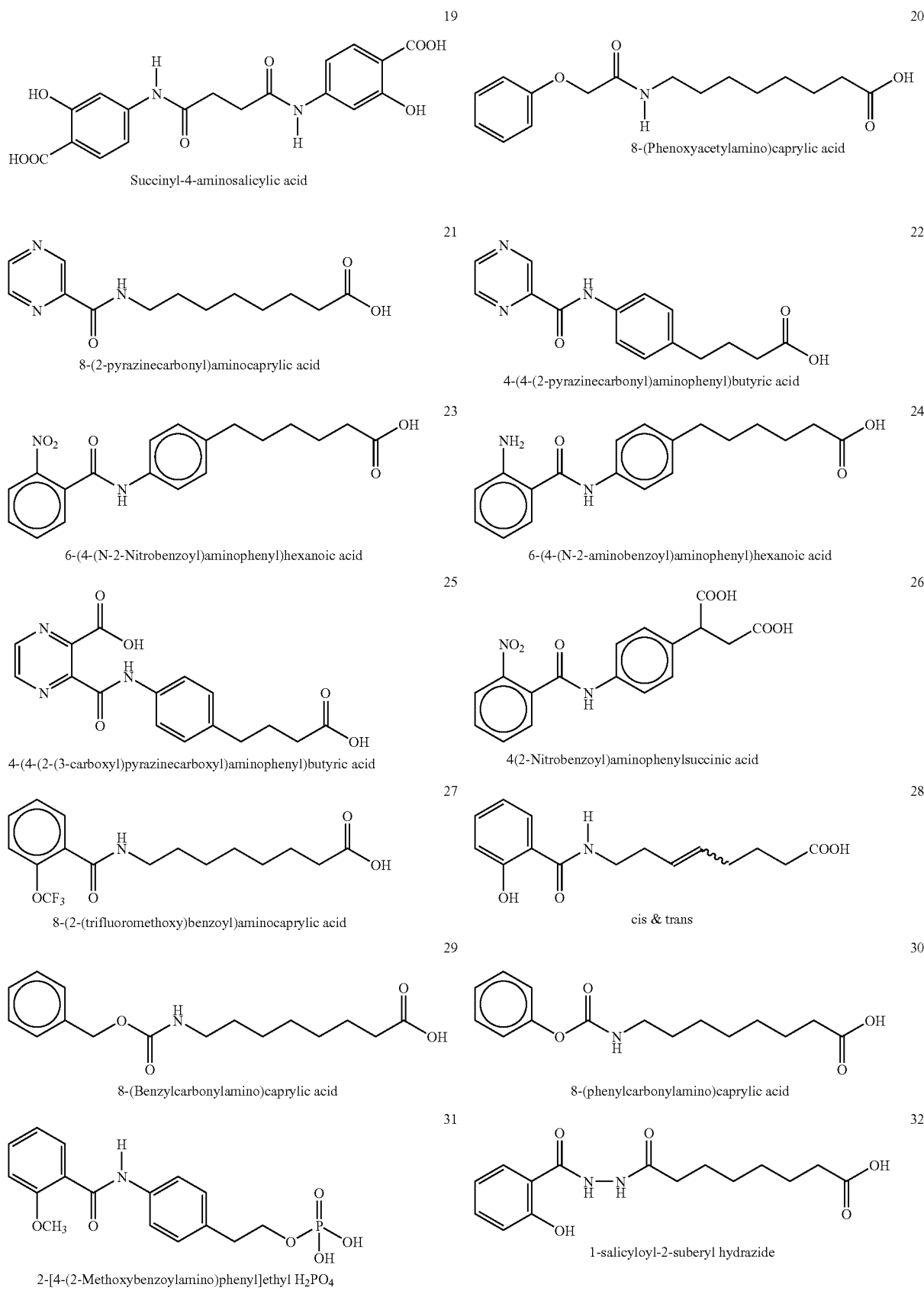

-continued

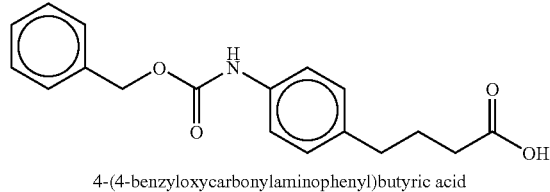
4-(4-benzyloxycarbonylaminophenyl)butyric acid

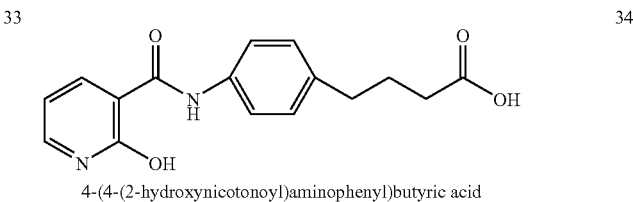
4-(4-(2-hydroxynicotonoyl)aminophenyl)butyric acid

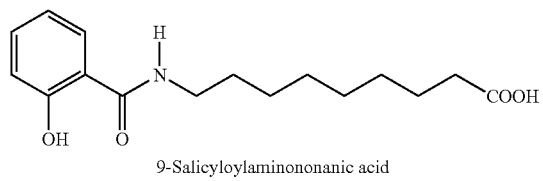
9-Salicyloylaminononanic acid

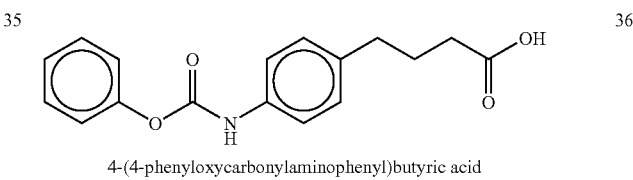
4-(4-phenyloxycarbonylaminophenyl)butyric acid

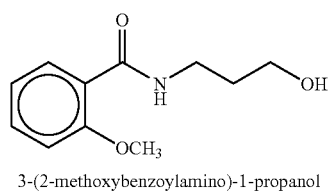
3-(2-methoxybenzoylamino)-1-propanol

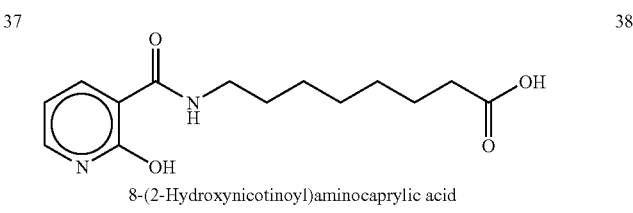
8-(2-Hydroxynicotinoyl)aminocaprylic acid

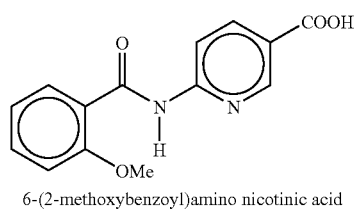
6-(2-methoxybenzoyl)amino nicotinic acid

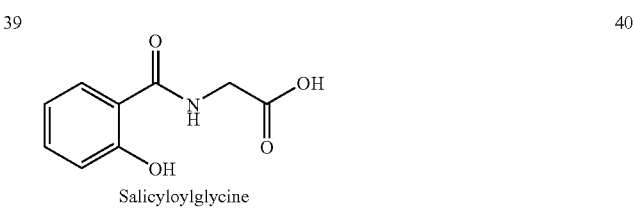
Salicyloylglycine

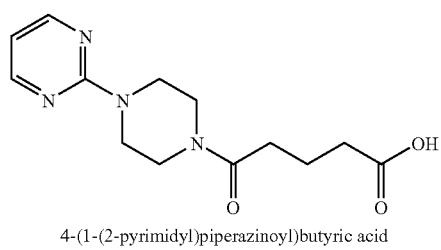
4-(1-(2-pyrimidyl)piperazinoyl)butyric acid

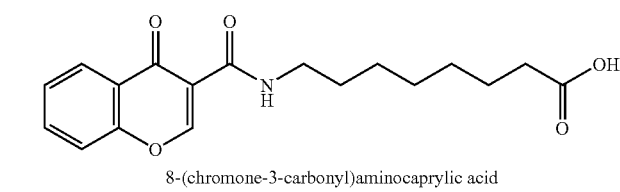
8-(chromone-3-carbonyl)aminocaprylic acid

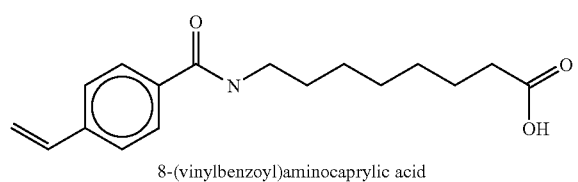
8-(vinylbenzoyl)aminocaprylic acid

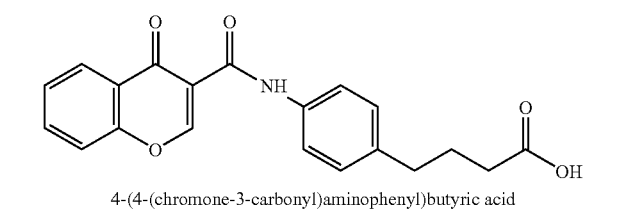
4-(4-(chromone-3-carbonyl)aminophenyl)butyric acid

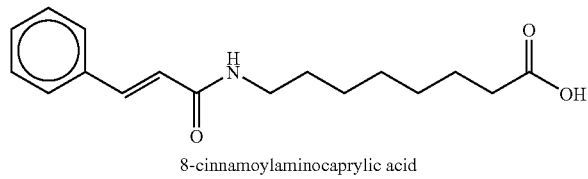
8-cinnamoylaminocaprylic acid

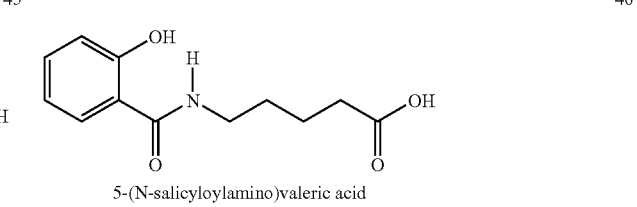
5-(N-salicyloylamino)valeric acid

-continued

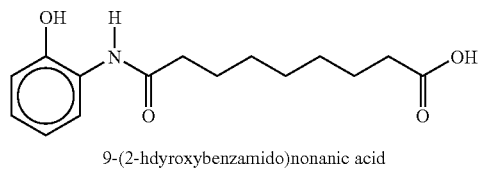
9-(2-hdyroxybenzamido)nonanic acid

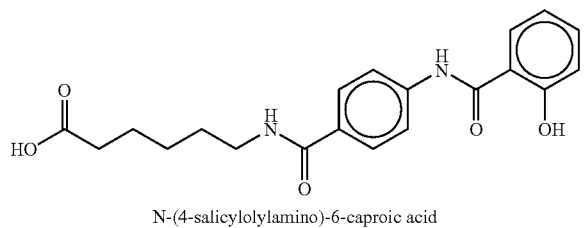
N-(4-salicylolylamino)-6-caproic acid

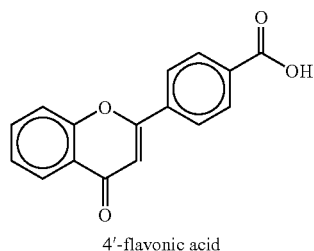
4'-flavonic acid

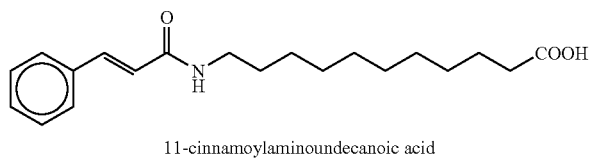
11-cinnamoylaminoundecanoic acid

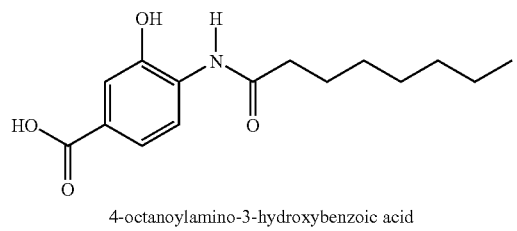
4-octanoylamino-3-hydroxybenzoic acid

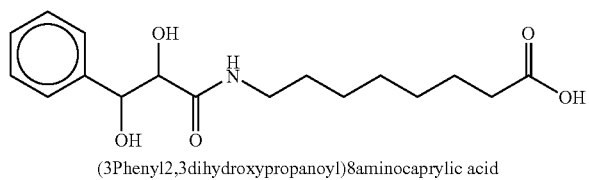
(3Phenyl2,3dihydroxypropanoyl)8aminocaprylic acid

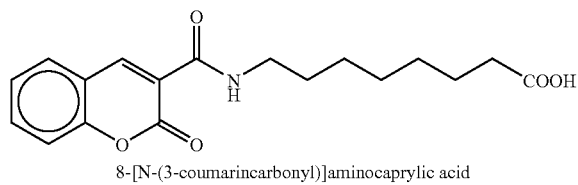
8-[N-(3-coumarincarbonyl)]aminocaprylic acid

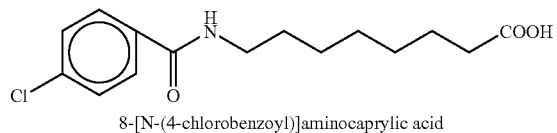
8-[N-(4-chlorobenzoyl)]aminocaprylic acid

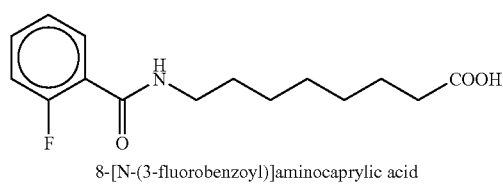
8-[N-(3-fluorobenzoyl)]aminocaprylic acid

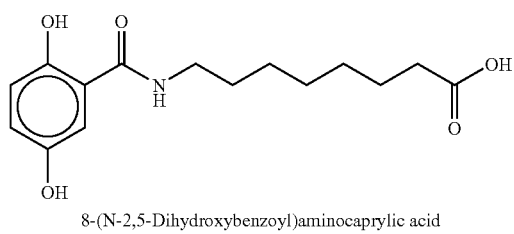
8-(N-2,5-Dihydroxybenzoyl)aminocaprylic acid

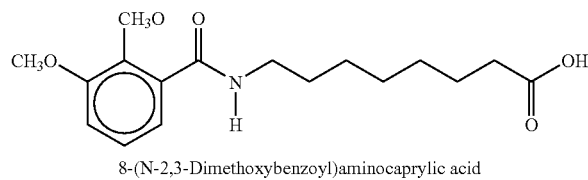
8-(N-2,3-Dimethoxybenzoyl)aminocaprylic acid

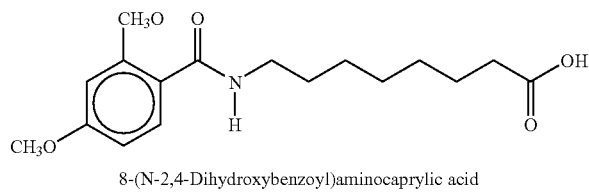
8-(N-2,4-Dihydroxybenzoyl)aminocaprylic acid

-continued

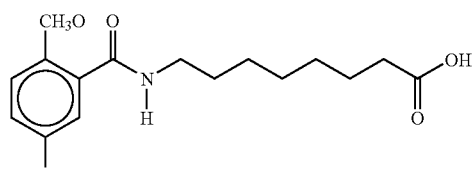
8-(N-2,5-Dimethoxybenzoyl)aminocaprylic acid

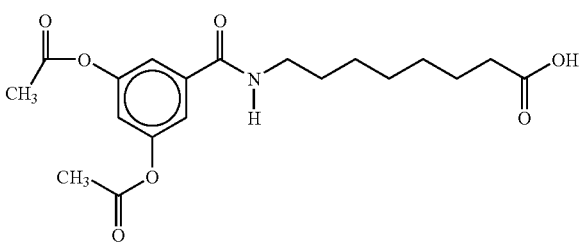
8-(N-3,5-Diacetyloxybenzoyl)aminocaprylic acid

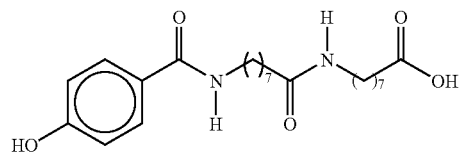
8-(N-4-Hydroxybenzoyl)aminocaprylic acid (dimer)

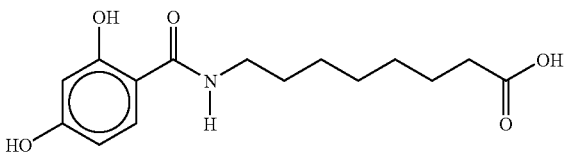
8-(N-2,4-Dihydroxybenzoyl)aminocaprylic acid

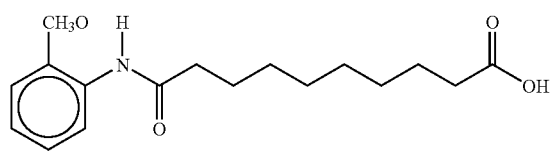
10-(N-2-Methoxyanilino)sebalic acid

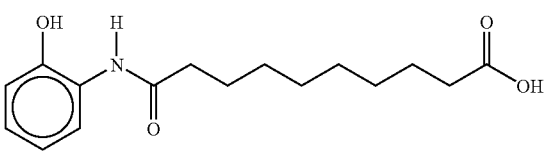
10-(N-2-Methoxyanilino)sebacic acid

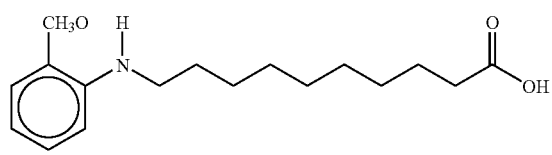
2-Methoxybenzenaminodecanoic acid

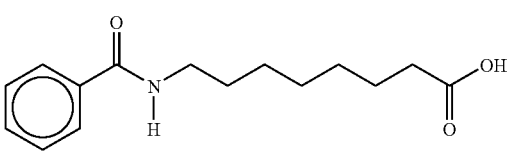
8-(N-benzoyl)aminocaprylic acid

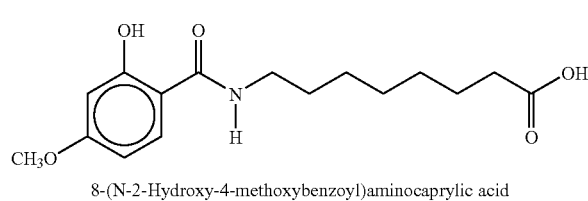
8-(N-2-Hydroxy-4-methoxybenzoyl)aminocaprylic acid

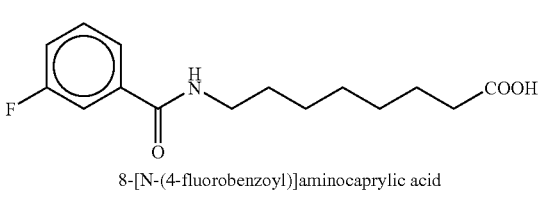
8-[N-(4-fluorobenzoyl)]aminocaprylic acid

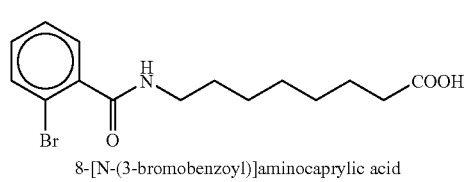
8-[N-(3-bromobenzoyl)]aminocaprylic acid

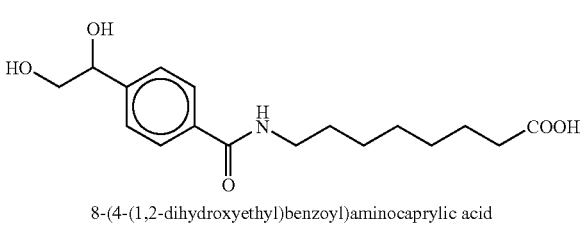
8-(4-(1,2-dihydroxyethyl)benzoyl)aminocaprylic acid

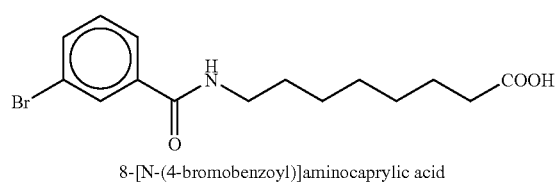
8-[N-(4-bromobenzoyl)]aminocaprylic acid

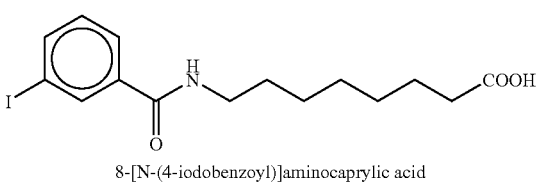
8-[N-(4-iodobenzoyl)]aminocaprylic acid

-continued

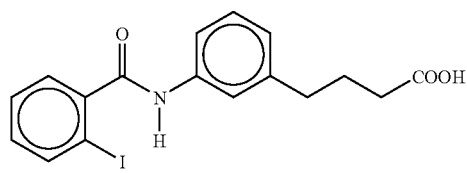
4-{4-[N-(2-iodobenzoyl)aminophenyl]}butyric acid

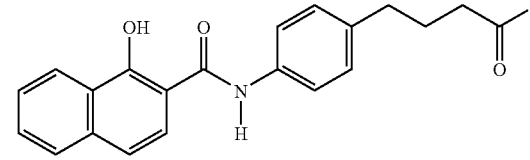
4-{4-[N-(1-hydroxy-2-naphthyoyl)aminophenyl]}butyric acid

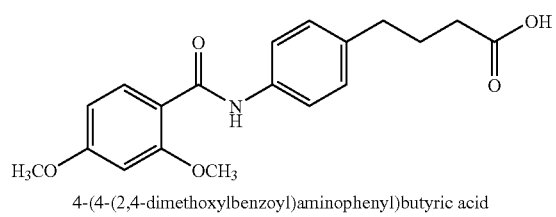
4-(4-(2,4-dimethoxylbenzoyl)aminophenyl)butyric acid

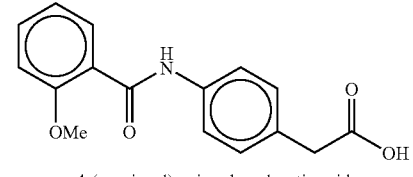
4-(o-anisoyl)aminophenylacetic acid

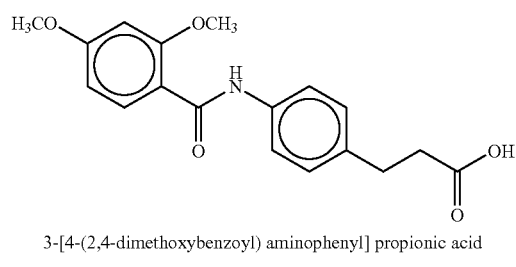
3-[4-(2,4-dimethoxybenzoyl) aminophenyl] propionic acid

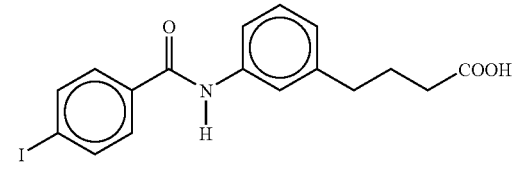
4-{4-[N-(4-iodobenzoyl)] aminophenyl} butyric acid

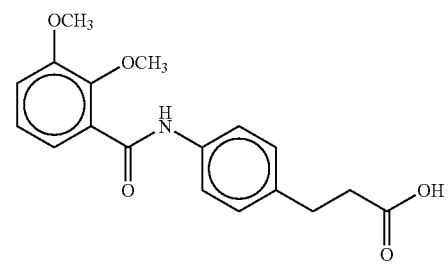
3-[4-(2,3-dimethoxybenzoyl) aminophenyl] propionic acid

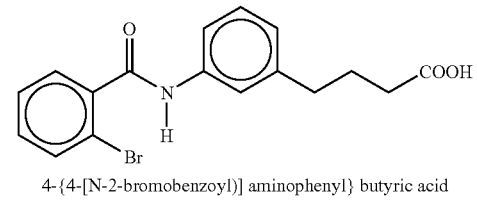
4-{4-[N-2-bromobenzoyl)] aminophenyl} butyric acid

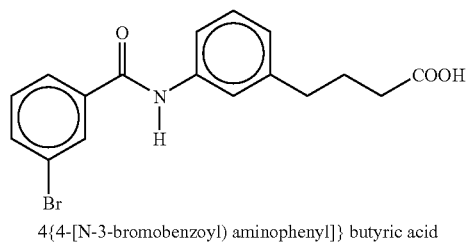
4{4-[N-3-bromobenzoyl) aminophenyl]} butyric acid

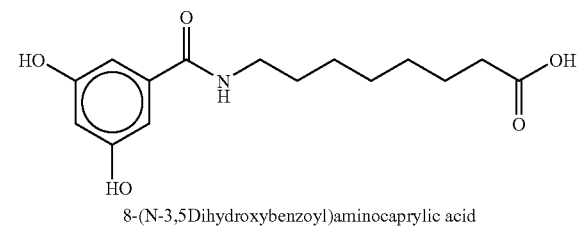
8-(N-3,5Dihydroxybenzoyl)aminocaprylic acid

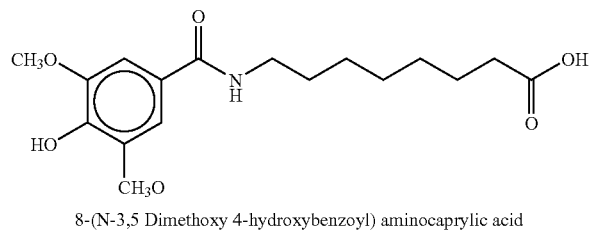
8-(N-3,5 Dimethoxy 4-hydroxybenzoyl) aminocaprylic acid

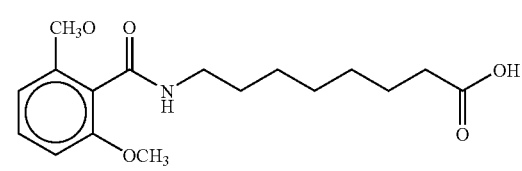
8(N-2-6-Dimethoxybenzoyl)aminocaprylic acid

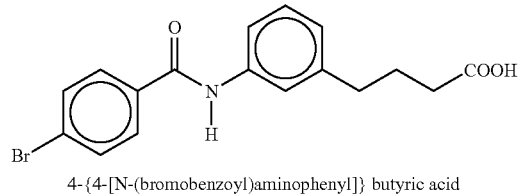
4-{4-[N-(bromobenzoyl)aminophenyl]} butyric acid

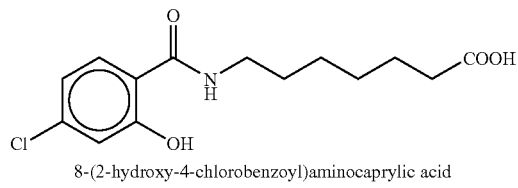
8-(2-hydroxy-4-chlorobenzoyl)aminocaprylic acid

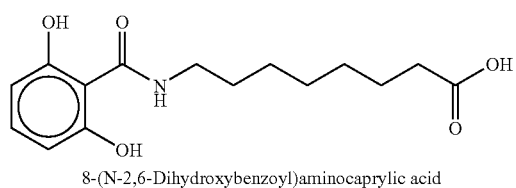
8-(N-2,6-Dihydroxybenzoyl)aminocaprylic acid

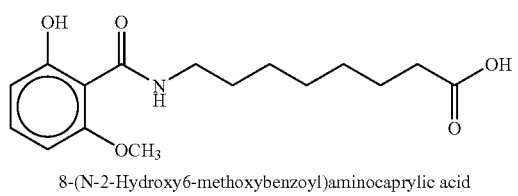
8-(N-2-Hydroxy6-methoxybenzoyl)aminocaprylic acid

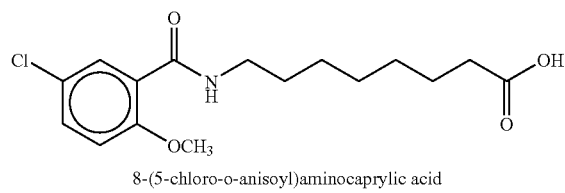
8-(5-chloro-o-anisoyl)aminocaprylic acid

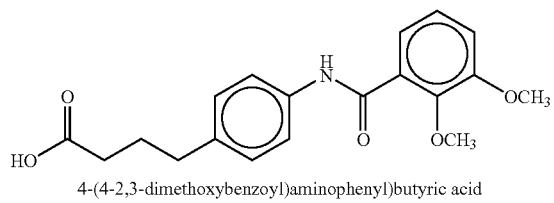
4-(4-2,3-dimethoxybenzoyl)aminophenyl)butyric acid

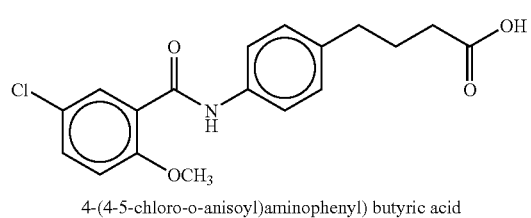
4-(4-5-chloro-o-anisoyl)aminophenyl) butyric acid

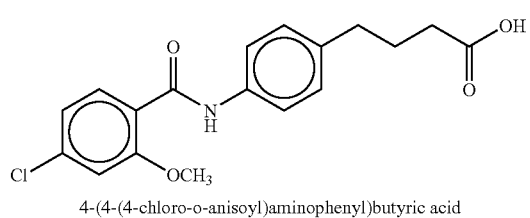
4-(4-(4-chloro-o-anisoyl)aminophenyl)butyric acid

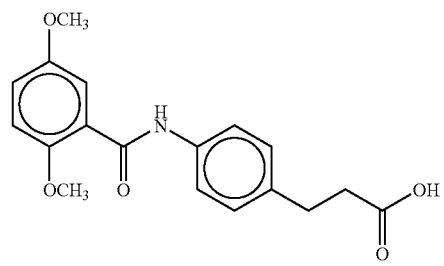
3-(4-(2,5-dimethoxybenzoyl)aminophenyl)propionic acid

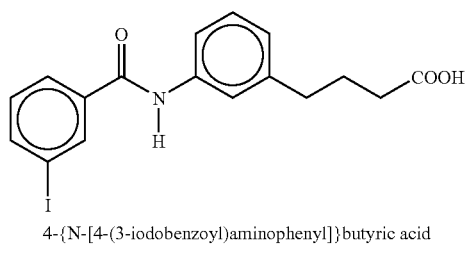
4-{N-[4-(3-iodobenzoyl)aminophenyl]}butyric acid

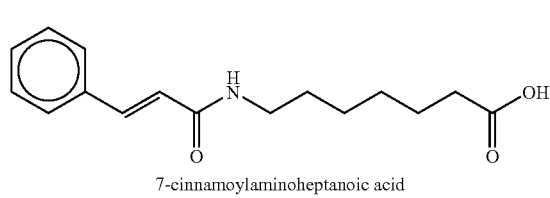
7-cinnamoylaminoheptanoic acid

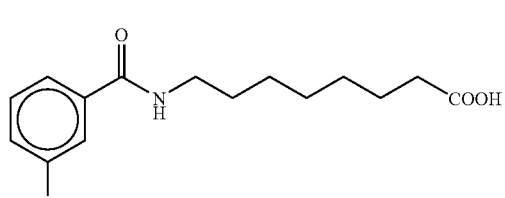
8-N-(3-iodobenzoyl)aminocaprylic acid

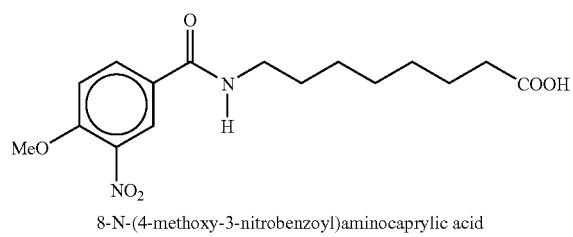
8-N-(4-methoxy-3-nitrobenzoyl)aminocaprylic acid

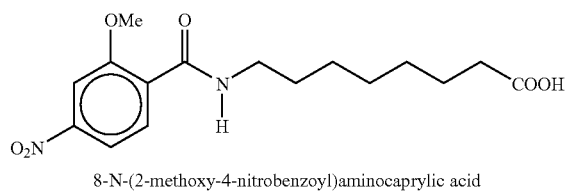
8-N-(2-methoxy-4-nitrobenzoyl)aminocaprylic acid

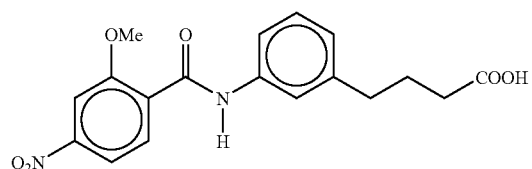
4-{N-[4-(2-methoxy-4-nitrobenzoyl)aminophenyl]}butyric acid

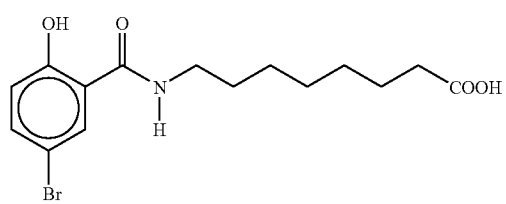
8-(N-2-hydroxy-5-bromobenzoyl)aminocaprylic acid

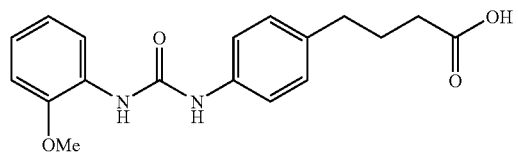

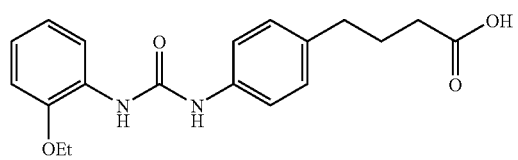

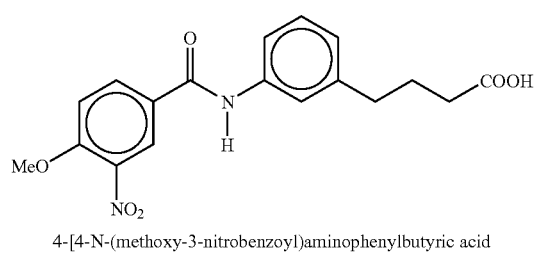
4-[4-N-(methoxy-3-nitrobenzoyl)aminophenylbutyric acid

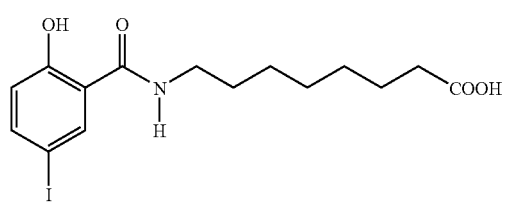
8-(N-2-hdyroxy-5-iodobenzoyl)aminocaprylic acid

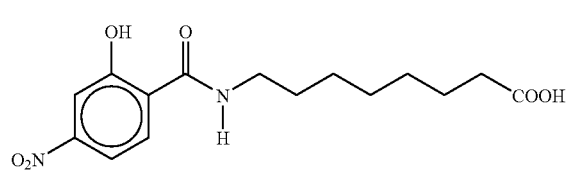
8-(N-2-hydroxy-4-nitrobenzoyl)aminocaprylic acid

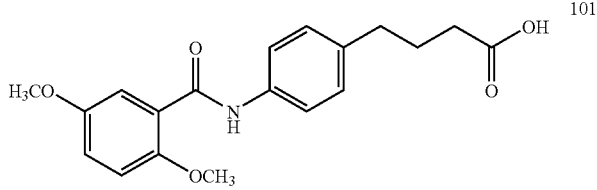
4-(4-(2,5-dimethoxybenzoyl)aminophenyl)butyric acid

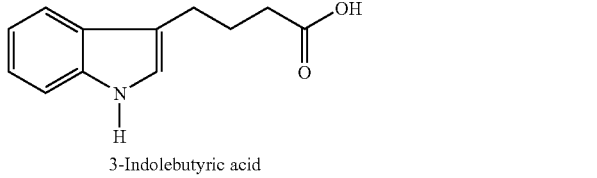
3-Indolebutyric acid

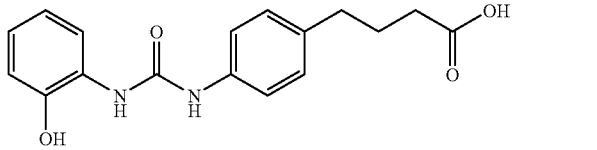

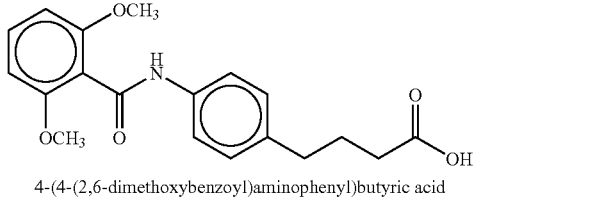
4-(4-(2,6-dimethoxybenzoyl)aminophenyl)butyric acid

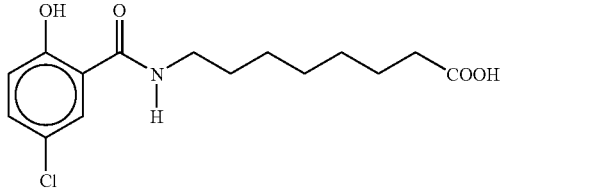
8-(N-2-hydroxy-5-chlorobenzoyl)aminocaprylic acid

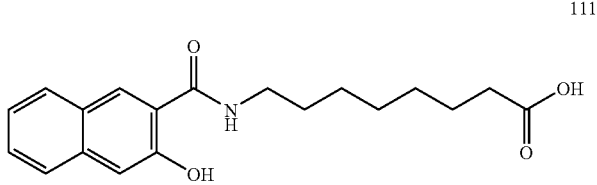
8-(3-hydroxy-2-naphthoyl)aminocaprylic acid

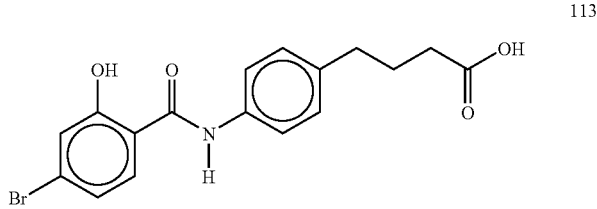
4-[-N-(2-hydroxy-4-bromobenzoyl)aminophenyl]butyric acid

-continued

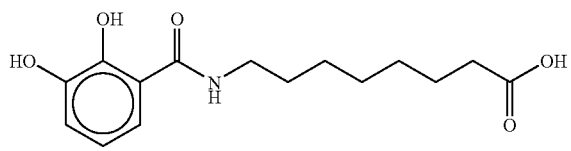
8-(N-2,3-Dihydroxybenzoyl)aminocaprylic acid

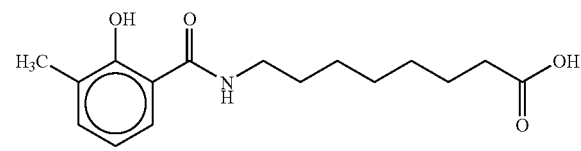
8-(N-3-methylsalicyloyl)aminocaprylic acid

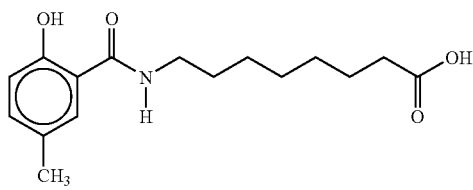
8-(N-5-methylsalicyloyl)aminocaprylic acid

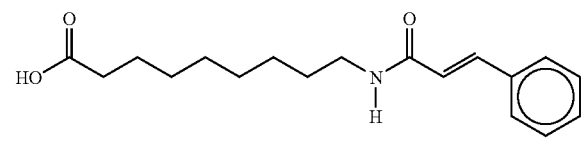
9-(cinnamoylamino)nonanoic acid

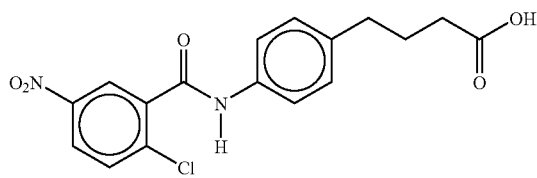
4-(4-(2-chloro-5-nitrobenzoyl)aminophenyl)butyric acid

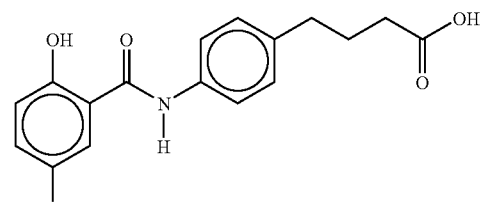
4-{-[N-(2-hydroxy-5-iodobenzoyl)]aminophenyl}butyric acid

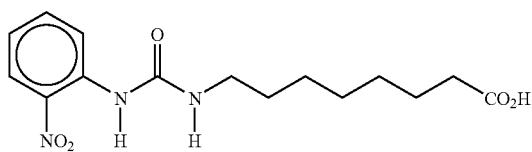
N-2-nitrophenyl-N'-(8-octanoic acid)urea

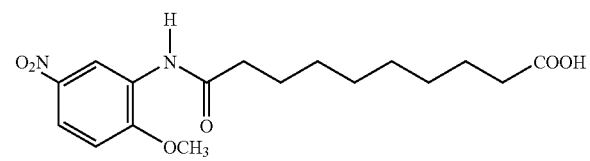
N-(2-methoxy-5-nitrophenyl) sebecoyl amide acid

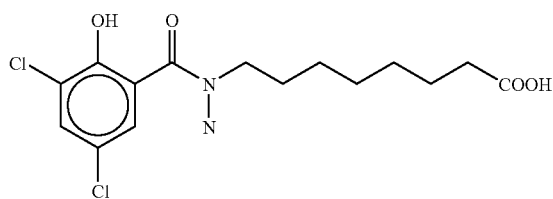
8-[N-(2-acetoxy-3,5-dichlorobenzoyl)]aminocaprylic acid

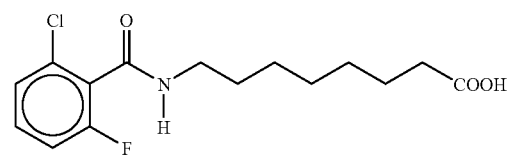
8-N-(2-chloro-6-fluorobenzoyl)aminocaprylic acid

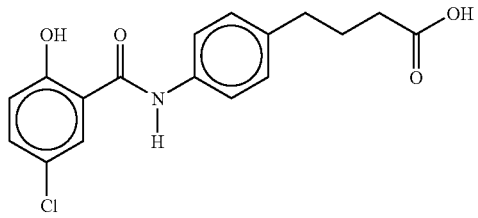
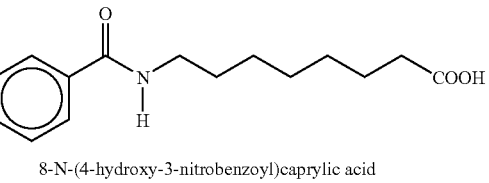
8-N-(4-hydroxy-3-nitrobenzoyl)caprylic acid

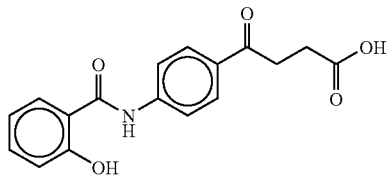
4-(4-Salicyloylaminophenyl)-4-oxobutryic acid

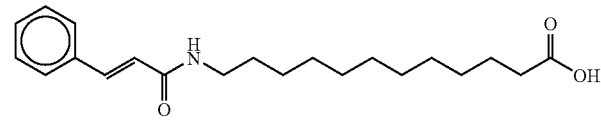
12-cinnamoyldodecanoic acid

129

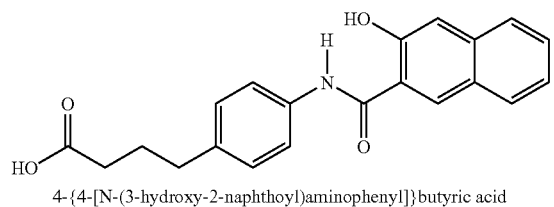

4-{4-[N-(3-hydroxy-2-naphthoyl)aminophenyl]}butyric acid

130

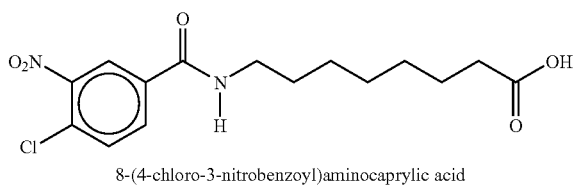

8-(4-chloro-3-nitrobenzoyl)aminocaprylic acid

131

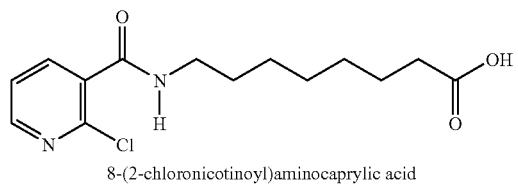

8-(2-chloronicotinoyl)aminocaprylic acid

132

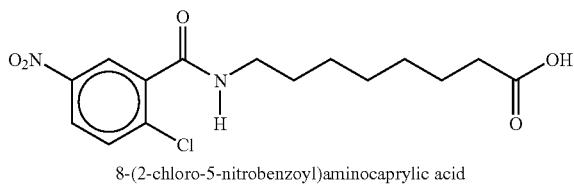

8-(2-chloro-5-nitrobenzoyl)aminocaprylic acid

133

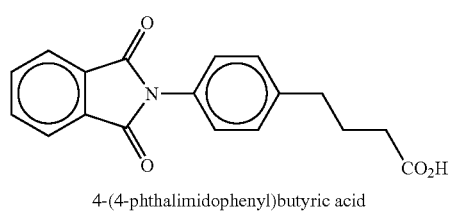

4-(4-phthalimidophenyl)butyric acid

134

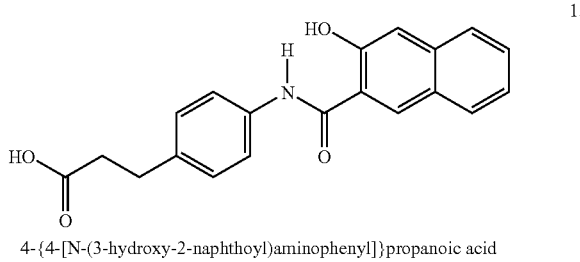

4-{4-[N-(3-hydroxy-2-naphthoyl)aminophenyl]}propanoic acid

135

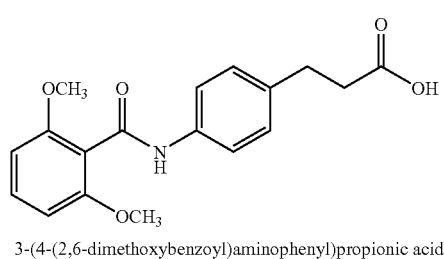

3-(4-(2,6-dimethoxybenzoyl)aminophenyl)propionic acid

136

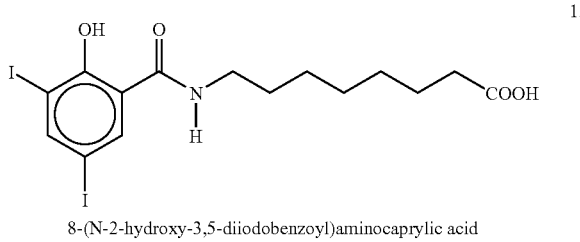

8-(N-2-hydroxy-3,5-diiodobenzoyl)aminocaprylic acid

137

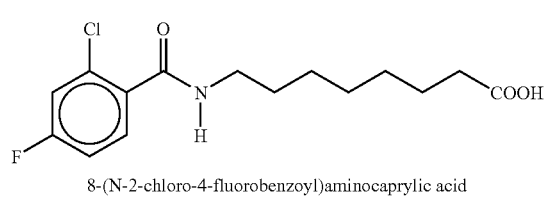

8-(N-2-chloro-4-fluorobenzoyl)aminocaprylic acid

138

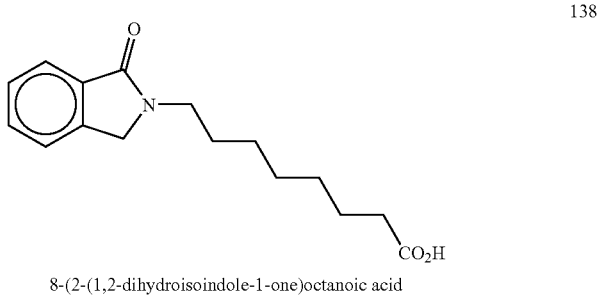

8-(2-(1,2-dihydroisoindole-1-one)octanoic acid

139

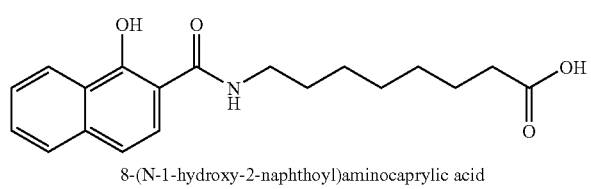

8-(N-1-hydroxy-2-naphthoyl)aminocaprylic acid

140

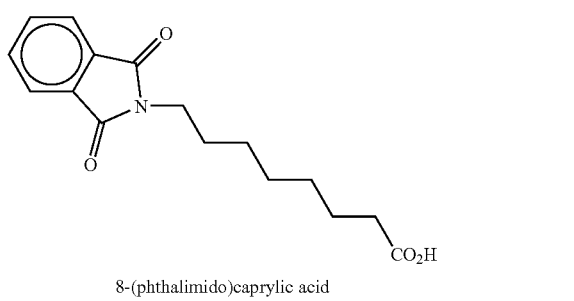

8-(phthalimido)caprylic acid

141

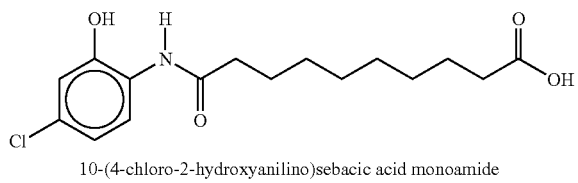

10-(4-chloro-2-hydroxyanilino)sebacic acid monoamide

142

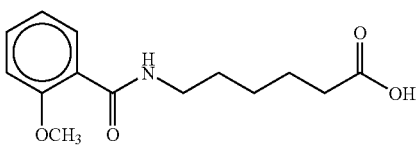

6-(anisoyl)aminocaproic acid

143

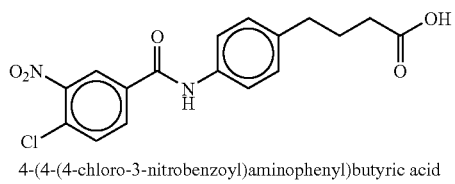

4-(4-(4-chloro-3-nitrobenzoyl)aminophenyl)butyric acid

144

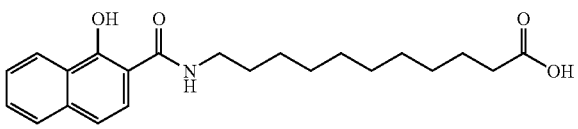

11-N-(1-hydroxy-2-naphthoyl)aminoundecanoic acid

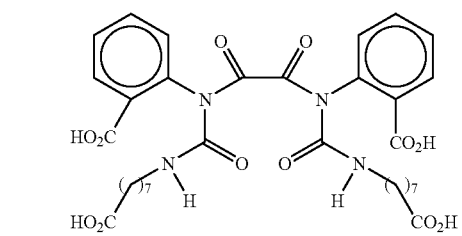

Bis(N-2carboxylphenyl-N-(N'-8-octanoic acid)ureal)oxalyl diamide

145

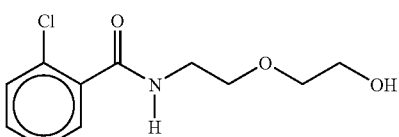

2-[2-N-(2-chlorobenzoyl)aminoethoxy]ethanol

146

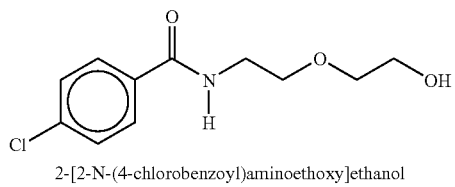

2-[2-N-(4-chlorobenzoyl)aminoethoxy]ethanol

147

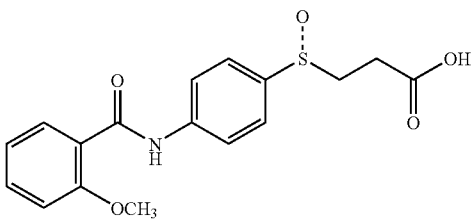

4-(2-methoxybenzoyl)amino 3-carboxysulfoxide

148

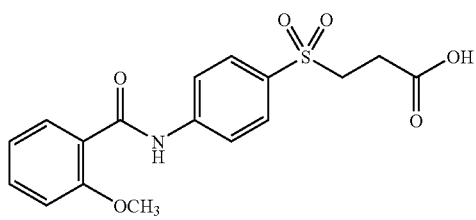

4-(2-methoxybenzoyl)amino 3-carboxypropylsulfone

149

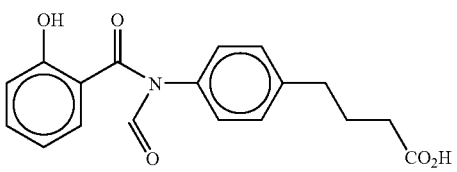

4-(4-(3-hydroxyphthalimido)phenyl)butyric acid

150

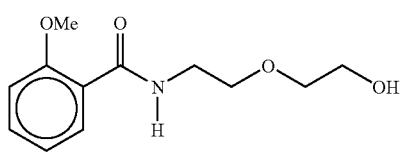

151

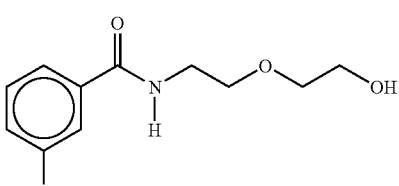

2-[2-N-(3-chlorobenzoyl)aminoethoxy]ethanol

152

153

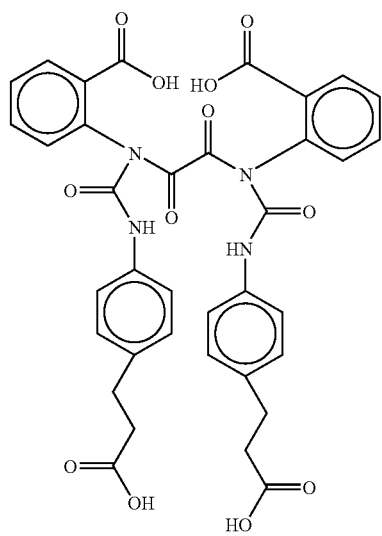

Bis(N-2-carboxyphenyl-N-(N'-3(4-aminophenyl)propionic acid)
ureal)oxaylyl diamide

154

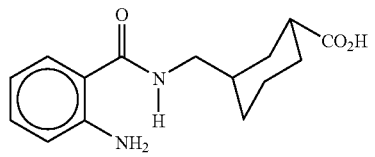

trans-4-(2-aminobenzamidomethyl)cyclohexamecarboxylic acid

155

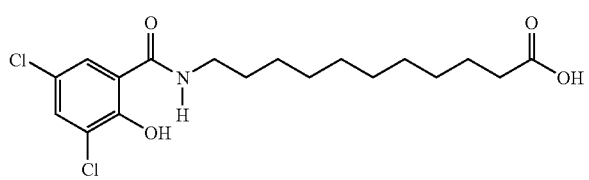

11-N-(3,5-dichloro-2-hdyroxybenzoyl)aminoudecanoic acid

156

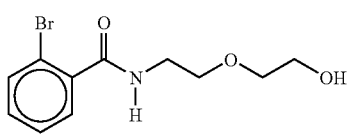

2-[N-(2-bromobenzoyl)aminoethoxy]ethanol

157

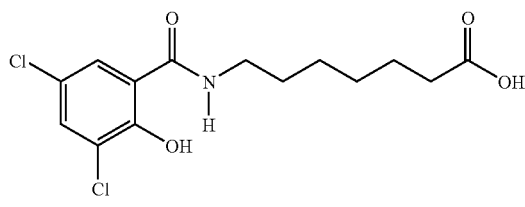

7-N-(3,5-dichloro-2-hydroxybenzoyl)aminoheptanoic acid

158

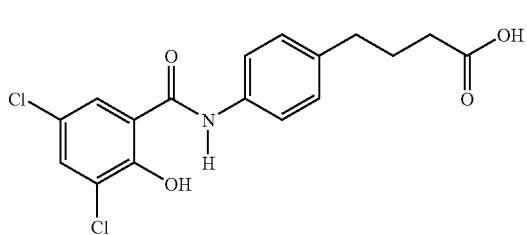

N-[3,5-dichloro-2-hydroxybenzoyl-4(4-aminophenyl)butyric acid

159

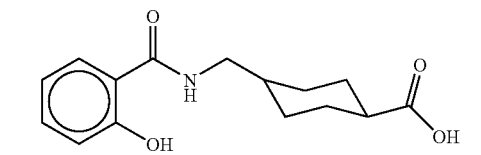

Trans-4-(N-salicyloylaminomethyl)cyclohexane carboxylic acid

160

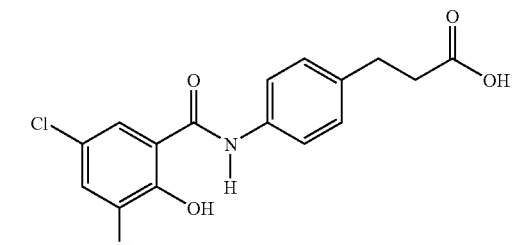

N-[3,5-dichloro-2-hydroxybenzoyl-3-(4-aminophenyl)]propionic acid

161

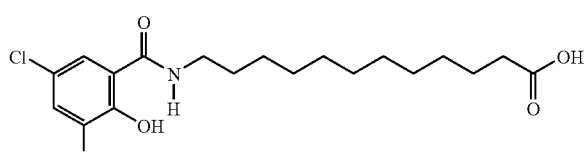

12-N-(3,5-dichloro-2-hydroxybenzoyl)aminododecanoic acid

162

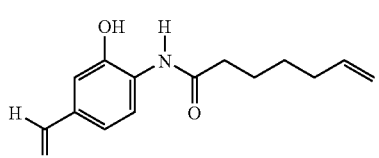

N-(2-hydroxy-4-carboxyl)-6-heptenamide

| | |
|---|---|
| 163 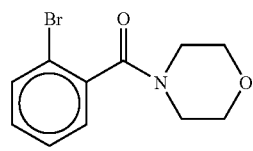<br>N-(2-bromobenzoyl)morpholine | 164 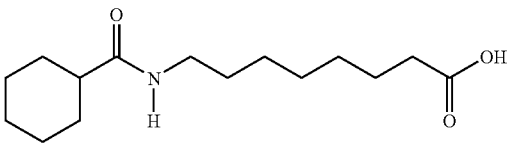<br>8-N-cyclohexanoylaminocaprylic acid |
| 165 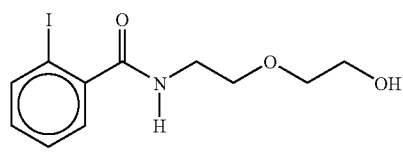<br>2-[N-(2-iodobenzoyl)aminoethoxy]ethanol | 166 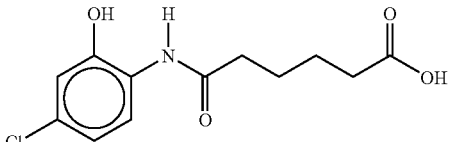<br>5-(4-chloro-2-hydroxyanilinocarbonyl)valeric acid |
| 167 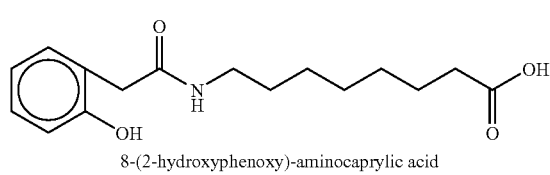<br>8-(2-hydroxyphenoxy)-aminocaprylic acid | 168 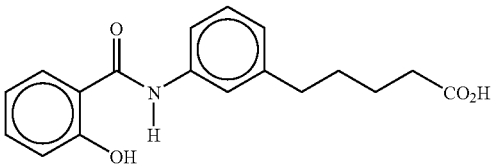<br>N-Salicoyl-5-(3-aminophenyl)valeric acid |
| 169 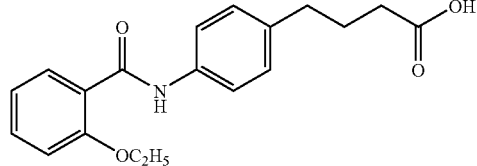<br>4-(4-(2-ethoxylbenzoyl)aminophenyl)butyric acid | 170 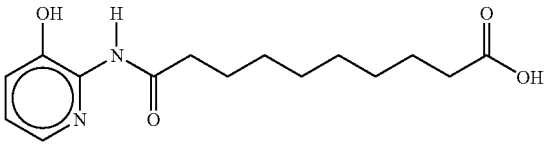<br>9-[2-(3-hydroxy)pyridylaminocarbonyl] nonanic acid |
| 171 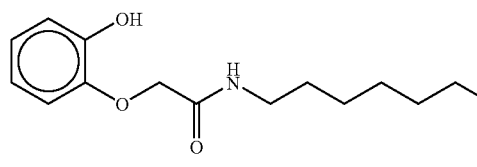<br>7-(2-hydroxyphenoxyacetyl)aminocaprylic acid | 172 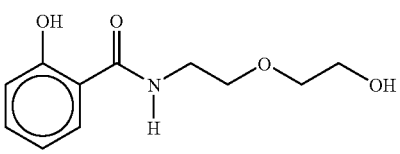<br>2-[N-(2-hydroxybenzoylamino)ethoxy]ethanol |
| 173 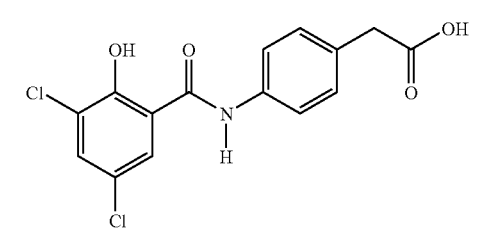<br>4-[N-(3,5-dichloro-2-hydroxybenzoyl)]aminophenylacetic acid | 174 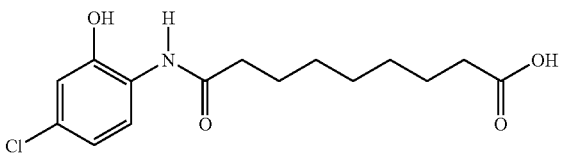<br>8-(2-hydroxy-5-chloroanilinocarboynl)ocatnoic acid |
| 175 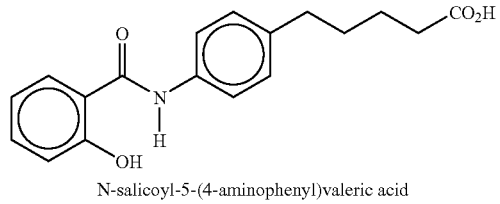<br>N-salicoyl-5-(4-aminophenyl)valeric acid | 176 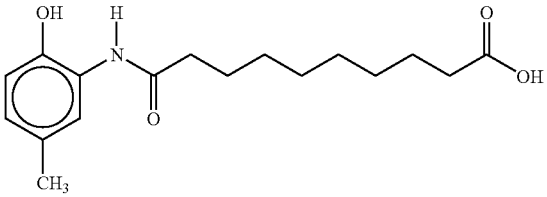<br>9-(2-hydroxy-5-methylanilinocarbonyl)nonanoic acid |

-continued

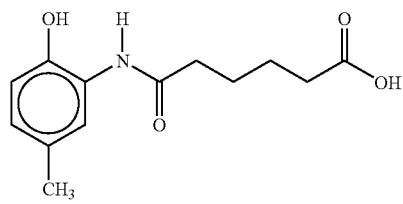
5-(2-hydroxy-5-methylanilinocarbonyl)valeric acid

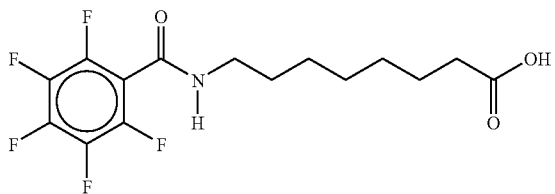
8-(pentafluorobenzoyl)aminocaprylic acid

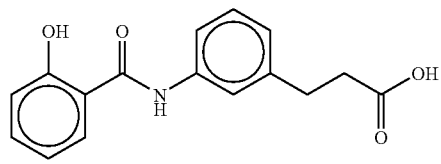
3-(3-(salicyloyl)aminophenyl)propionic acid

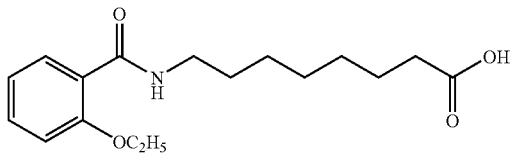
8-(2-ethoxybenzoyl)aminocaprylic acid

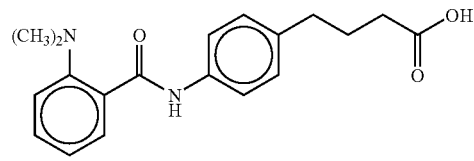
4-(4-(2-Dimethylamino benzoic)aminophenyl)butyric acid

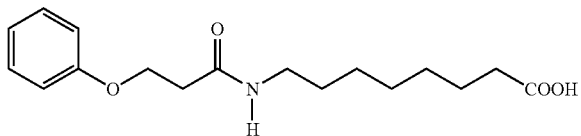
8-(3-Phenoxylpropionylamino)caprylic acid

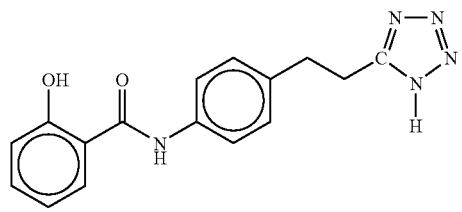
4-(Salicyloyl)aminophenylethyltetrazole

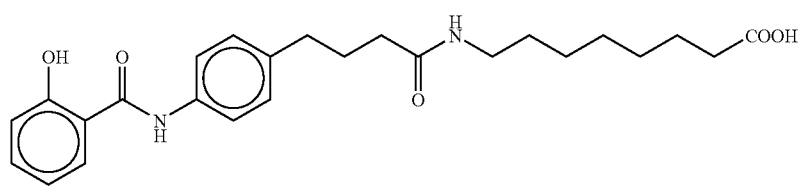
8(-(4(N-Saliciloyl-4aminophenyl)butyric)aminocaprylic acid [sic]

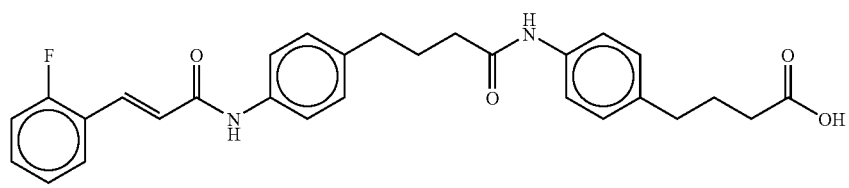
4-(4-(N-(2-Fluorocinnamoyl))aminophenyl) butyric

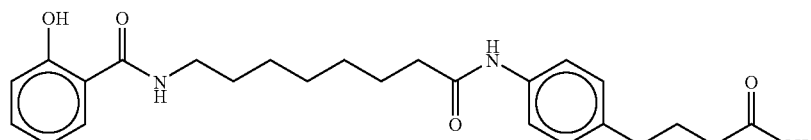
4-(4-(N-8(N-Salicyloyl)aminocaprylic)aminophenyl)butyric acid

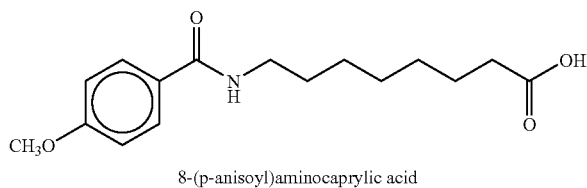
8-(p-anisoyl)aminocaprylic acid

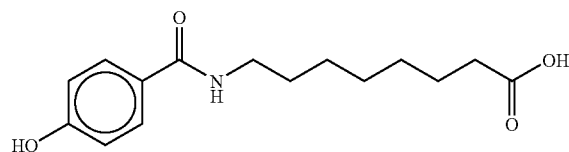
8-(4-Hydroxybenzoyl)aminocaprylic acid

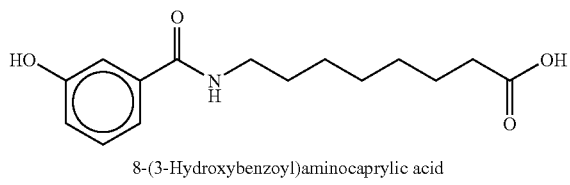
8-(3-Hydroxybenzoyl)aminocaprylic acid

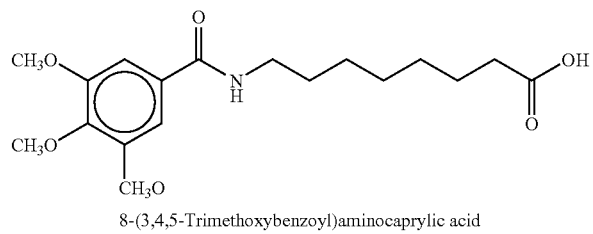
8-(3,4,5-Trimethoxybenzoyl)aminocaprylic acid

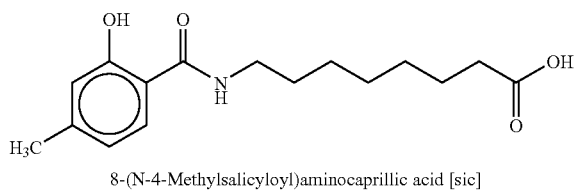
8-(N-4-Methylsalicyloyl)aminocaprillic acid [sic]

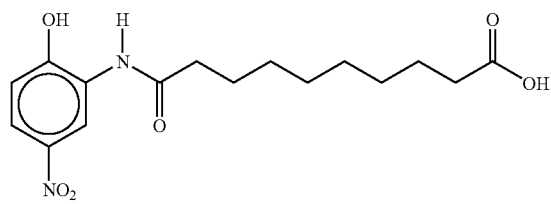
N-10-(2-hydroxy-5-nitroanilino)decanoic acid

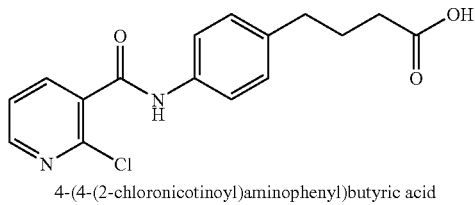
4-(4-(2-chloronicotinoyl)aminophenyl)butyric acid

Compositions comprising the carrier compounds discussed above and active agents are effective in delivering active agents to selected biological systems.

DETAILED DESCRIPTION OF THE INVENTION

The specific compositions of the present invention include an active agent and a carrier. These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds including, but not limited to, chickens; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Subcutaneous, sublingual, and intranasal coadministration of an active agent, such as, for example, recombinant human growth hormone (rhGH); salmon calcitonin; heparin, including, but not limited to, low molecular weight heparin; parathyroid hormone; and compounds in compositions as described herein result in an increased bioavailability of the active agent compared to administration of the active agent alone.

Active Agents

Active agents suitable for use in the present invention include biologically or chemically active agents, chemically active agents, including, but not limited to, fragrances, as well as other active agents such as, for example, cosmetics.

Biologically or chemically active agents include, but are not limited to, pesticides, pharmacological agents, and therapeutic agents. For example, biologically or chemically active agents suitable for use in the present invention include, but are not limited to, peptides, and particularly small peptides; hormones, and particularly hormones which by themselves do not or only a fraction of the administered dose passes through the gastro-intestinal mucosa and/or are susceptible to chemical cleavage by acids and enzymes in the gastro-intestinal tract; polysaccharides, and particularly mixtures of mucopolysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); parathyroid hormone antimicrobials, including, but not limited to anti-fungal agents; or any combination thereof.

Carriers

Although compounds 1-193 above have been found to act as carriers for the oral delivery of biologically or chemically active agents, special mention is made of compounds 9, 35, 64, 67, 79, 102, 109, 111, 117, 122, 136, and 141, above.

Properties of compounds 1-193 are listed in Table 1, below.

TABLE 1

| | Carrier Properties | | | | | | | | |
|---|---|---|---|---|---|---|---|---|---|
| | Anal. Calculated For | | | | Found | | | | Melting Point |
| Compound | C | H | N | S | C | H | N | S | (° C.) |
| 1. | 48.8 | 4.70 | 4.40 | | 48.81 | 4.64 | 4.39 | | |
| 2. | 64.73 | 7.97 | 10.06 | | 64.54 | 7.81 | 10.19 | | |
| 3. | 55.33 | 5.80 | 4.03 | | 55.40 | 5.79 | 3.96 | | 69-71 |
| 4. | 62.64 | 6.06 | 5.62 | | 62.75 | 6.08 | 5.51 | | 151-154 |
| 5. | 65.16 | 6.11 | 13.40 | | 65.29 | 6.03 | 13.29 | | 144-145 |
| 6. | 54.70 | 3.24 | 3.75 | | 54.29 | 3.24 | 3.54 | | 165-169 |
| 7. | 69.00 | 6.11 | 4.47 | | 69.09 | 6.24 | 4.43 | | 126-129 |
| 8. | 65.51 | 7.90 | 4.78 | | 65.60 | 8.25 | 4.83 | | 89-90 |
| 9. | 68.99 | 6.11 | 4.47 | | 69.01 | 6.08 | 4.47 | | 104-107 |
| 10. | 52.74 | 4.42 | 7.69 | | 52.91 | 4.45 | 7.49 | | 142-145 |
| 11. | 48.83 | 5.85 | 8.14 | | 48.95 | 5.89 | 8.02 | | 120-122 |
| 12. | 69.71 | 6.47 | 4.28 | | 69.56 | 6.47 | 4.38 | | 144-146 |
| 13. | 65.51 | 7.90 | 4.77 | | 65.23 | 7.88 | 4.72 | | 72.5-74.5 |
| 14. | 60.17 | 5.36 | 4.39 | 10.04 | 60.09 | 5.36 | 4.35 | 9.99 | 155-156 |
| 15. | 52.38 | 4.79 | 11.11 | | 52.45 | 4.94 | 11.08 | | 220-222 |
| 16. | 67.60 | 5.95 | 3.94 | | 67.34 | 6.01 | 3.91 | | 219-222 |
| 17. | 68.09 | 6.53 | 3.78 | | 67.77 | 6.24 | 3.81 | | 130-133 |
| 18. | 54.13 | 5.30 | 10.52 | | 54.12 | 5.24 | 10.54 | | 192.5-195.5 |
| 19. | 55.26 | 4.21 | 7.16 | | 54.48 | 4.32 | 6.86 | | >280 dec |
| 20. | 65.51 | 7.90 | 4.77 | | 65.52 | 7.90 | 4.77 | | 75-80 |
| 21. | 58.85 | 7.21 | 15.84 | | 58.86 | 7.16 | 15.69 | | 120-122 |
| 22. | 63.15 | 5.30 | 14.73 | | 63.30 | 5.43 | 14.18 | | 197-201 |
| 23. | 64.04 | 5.66 | 7.86 | | 64.17 | 5.67 | 7.75 | | 188-190 |
| 24. | 69.91 | 6.88 | 8.46 | | 69.98 | 6.79 | 8.58 | | 131-134 |
| 25. | 58.36 | 4.56 | 12.76 | | 58.20 | 4.63 | 12.61 | | 138-141 |
| 26. | 56.98 | 3.94 | 7.82 | | 56.39 | 3.92 | 7.74 | | 221-223 |
| 27. | 55.33 | 5.80 | 4.03 | | 55.47 | 6.10 | 4.04 | | 70-72 |
| 28. | | | | | | | | | |
| 29. | 65.74 | 7.58 | 4.79 | | 65.51 | 7.89 | 4.78 | | 52-55 |
| 30. | 64.50 | 7.57 | 5.02 | | 64.07 | 7.81 | 5.40 | | 70-74 |
| 31. | 54.70 | 5.17 | 3.99 | | 54.50 | 4.99 | 3.95 | | 173-174 |
| 32. | 58.63 | 5.94 | 9.12 | | 58.73 | 6.20 | 10.34 | | 125-129 |
| 33. | 69.00 | 6.10 | 4.47 | | 69.18 | 6.08 | 4.54 | | 100-102 |
| 34. | 63.99 | 5.37 | 9.33 | | 63.46 | 5.35 | 9.06 | | 218-221 c. |
| 35. | 65.5 | 7.90 | 4.78 | | 65.37 | 8.00 | 4.66 | | 96-97 c. |
| 36. | 68.22 | 5.72 | 4.68 | | 67.88 | 5.65 | 4.55 | | 134-137 |
| 37. | 63.14 | 7.23 | 6.69 | | 63.15 | 7.29 | 6.58 | | 53.5-56 |
| 38. | 60.00 | 7.14 | 10.00 | | 59.78 | 7.31 | 9.94 | | 135-138 |
| 39. | 61.67 | 4.41 | 10.29 | | 61.69 | 4.41 | 10.12 | | >225 |
| 40. | 55.39 | 4.65 | 7.18 | | 55.52 | 4.77 | 7.30 | | 162.5-166 |
| 41. | 56.10 | 6.52 | 20.14 | | 55.66 | 6.71 | 19.69 | | 129-131 |
| 42. | 65.24 | 6.39 | 4.23 | | 65.42 | 6.16 | 3.78 | | 130-133.5 |
| 43. | 70.59 | 7.96 | 4.84 | | 70.35 | 8.13 | 4.79 | | 111-113 |
| 44. | 68.37 | 4.88 | 3.99 | | 68.61 | 4.89 | 3.79 | | 120-123 |
| 45. | 70.59 | 7.96 | 4.84 | | 70.48 | 7.97 | 4.71 | | 108-110 |
| 46. | 60.75 | 6.37 | 5.90 | | 60.97 | 6.18 | 5.80 | | 100.5-103 |
| 47. | 64.50 | 7.57 | 5.02 | | 64.42 | 7.58 | 5.01 | | 97-100 |
| 48. | 64.86 | 5.98 | 7.56 | | 64.50 | 6.01 | 7.52 | | 165-169 |
| 49. | 72.18 | 3.76 | 0.00 | | 72.13 | 3.84 | 0.00 | | >225 |
| 50. | 72.51 | 8.76 | 4.23 | | 72.39 | 8.84 | 4.12 | | 120-122 |
| 51. | 64.50 | 7.58 | 5.01 | | 64.75 | 7.65 | 4.69 | | 200.5-204 |
| 52. | | 7.74 | 4.33 | | | 7.82 | 4.30 | | 88-89 |
| 53. | 65.24 | 6.39 | 4.23 | | 65.15 | 6.46 | 4.23 | | 93.-97 |
| 54. | 60.49 | 6.77 | 4.70 | | 60.54 | 6.76 | 4.65 | | 114-116 |
| 55. | 64.04 | 7.17 | 4.98 | | 63.90 | 7.11 | 4.93 | | 105-106 |
| 56. | 61.00 | 7.17 | 4.74 | | 60.49 | 6.92 | 4.65 | | 146-148 |
| 57. | 63.14 | 7.79 | 4.33 | | 63.22 | 7.82 | 4.36 | | 59-61 |
| 58. | 63.14 | 7.79 | 4.33 | | 63.17 | 7.86 | 4.26 | | 102-104 |
| 59. | 63.14 | 7.79 | 4.33 | | 63.35 | 7.68 | 4.20 | | 89-90 |
| 60. | 60.15 | 6.64 | 3.69 | | 59.84 | 6.66 | 3.64 | | 112-113 |

TABLE 1-continued

| | Carrier Properties | | | | | | | | |
|---|---|---|---|---|---|---|---|---|---|
| | Anal. Calculated For | | | | Found | | | | Melting Point |
| Compound | C | H | N | S | C | H | N | S | (° C.) |
| 61. | 65.53 | 8.85 | 6.65 | | 65.34 | 8.73 | 6.67 | | 89-92 |
| 62. | 61.00 | 7.17 | 4.74 | | 60.94 | 7.12 | 4.49 | | 104-108 |
| 63. | 66.43 | 8.20 | 4.56 | | 66.29 | 8.23 | 4.36 | | 77-78 |
| 64. | 65.51 | 7.90 | 4.77 | | 65.52 | 8.06 | 4.54 | | 97-98 |
| 65. | 69.59 | 9.28 | 4.77 | | 69.64 | 9.35 | 4.86 | | 62-65 |
| 66. | 68.41 | 8.04 | 5.32 | | 68.41 | 8.06 | 5.28 | | 88-89 |
| 67. | 62.12 | 7.49 | 4.53 | | 61.94 | 7.45 | 4.43 | | 98-99 |
| 68. | 64.04 | 7.17 | 4.98 | | 64.07 | 7.16 | 4.95 | | 106-107 |
| 69. | 52.64 | 5.89 | 4.09 | | 52.63 | 5.85 | 4.03 | | 109-110 |
| 70. | 63.15 | 7.74 | 4.33 | | 63.26 | 7.90 | 4.14 | | 97-100 |
| 71. | 52.64 | 5.89 | 4.09 | | 52.67 | 5.99 | 3.97 | | 114-115 |
| 72. | 46.31 | 5.18 | 3.61 | | 46.25 | 4.86 | 3.52 | | 143-144 |
| 73. | 49.89 | 3.94 | 3.42 | | 49.92 | 3.85 | 3.39 | | 170-171 |
| 74. | 72.19 | 5.48 | 4.01 | | 71.51 | 5.33 | 3.75 | | 180 |
| 75. | 66.46 | 6.16 | 4.08 | | 66.47 | 6.26 | 4.06 | | 168.5-171 |
| 76. | 67.37 | 5.26 | 4.91 | | 67.31 | 5.25 | 5.07 | | 130-133 |
| 77. | 65.65 | 5.78 | 4.26 | | 65.49 | 6.04 | 4.26 | | 179-183 |
| 78. | 49.89 | 3.94 | 3.42 | | 49.8 | 3.71 | 3.29 | | 237-238 |
| 79. | 65.65 | 5.78 | 4.26 | | 65.21 | 6.05 | 4.24 | | 156-158 |
| 80. | 56.38 | 4.45 | 3.87 | | 56.4 | 4.21 | 3.91 | | 130-131 |
| 81. | 56.38 | 4.45 | 3.87 | | 56.46 | 4.5 | 3.84 | | 197-198 |
| 82. | 56.6 | 7.49 | 4.4 | | 56.3 | 7.49 | 4.14 | | 58-62 |
| 83. | 57.03 | 8.2 | 3.91 | | 57.17 | 7.8 | 3.7 | | 138-140 |
| 84. | 57.58 | 7.11 | 3.95 | | 57.52 | 7.7 | 3.94 | | |
| 85. | 56.38 | 4.45 | 3.87 | | 56.31 | 4.25 | 3.64 | | 230-231 |
| 86. | 57.42 | 6.42 | 4.46 | | 57.14 | 6.45 | 4.2 | | 116-117 |
| 87. | 61 | 7.17 | 4.74 | | 61.18 | 7.05 | 4.65 | | 108-109 |
| 88. | 62.12 | 7.49 | 4.53 | | 62.34 | 7.21 | 4.39 | | 107-109 |
| 89. | 58.63 | 6.76 | 4.27 | | 58.53 | 6.81 | 4.2 | | 117-118 |
| 90. | 66.46 | 6.16 | 4.08 | | 66.18 | 6.15 | 3.84 | | 100-104 |
| 91. | 62.16 | 5.21 | 4.03 | | 61.93 | 4.97 | 3.86 | | 183-185 |
| 92. | 62.16 | 5.21 | 4.03 | | 62.2 | 5.14 | 3.98 | | 167-170 |
| 93. | 58.63 | 6.76 | 4.27 | | 58.64 | 6.83 | 4.19 | | 106-108 |
| 94. | 65.65 | 5.81 | 4.25 | | 65.56 | 5.64 | 4.2 | | 153-156 |
| 95. | 49.89 | 3.94 | 3.42 | | 49.9 | 3.81 | 3.18 | | 216-217 |
| 96. | 69.82 | 7.64 | 5.09 | | 69.91 | 7.66 | 5.02 | | 129-131 |
| 97. | 46.31 | 5.18 | 3.61 | | 46.54 | 4.95 | 3.64 | | 122-123 |
| 98. | 56.8 | 6.55 | 8.28 | | 56.69 | 6.67 | 8.1 | | |
| 99. | 56.8 | 6.55 | 8.28 | | 57.37 | 6.57 | 8.33 | | 117-118 |
| 100. | 60.33 | 5.06 | 7.82 | | 59.98 | 4.97 | 7.67 | | 207-209 |
| 101. | 66.46 | 6.16 | 4.08 | | 66.37 | 6.32 | 3.96 | | 126-128 |
| 102. | 50.29 | 5.63 | 3.91 | | 50.14 | 5.7 | 3.76 | | 129-131 |
| 103. | 70.93 | 5.95 | 6.89 | | 70.94 | 6.44 | 6.89 | | |
| 104. | 65.84 | 6.14 | 8.53 | | 65.94 | 6.19 | 8.54 | | 228-231 |
| 105. | 64.96 | 5.77 | 8.91 | | 64.89 | 5.82 | 8.82 | | |
| 106. | 66.65 | 6.48 | 8.18 | | 66.39 | 6.49 | 8.05 | | 140-142 |
| 107. | 66.47 | 6.12 | 4.07 | | 66.5 | 6.26 | 4.08 | | 140-142 |
| 108. | 60.33 | 5.06 | 7.82 | | 60.32 | 4.99 | 7.78 | | 150-151 |
| 109. | 57.41 | 6.42 | 4.46 | | 57.07 | 6.44 | 4.39 | | 121-123 |
| 110. | 44.46 | 4.97 | 3.46 | | | | | | 133-135 |
| 111. | 69.28 | 7.03 | 4.25 | | 68.86 | 7.07 | 4.11 | | 147-149 |
| 112. | 55.55 | 6.22 | 8.64 | | 55.27 | 5.99 | 8.5 | | 120-121 |
| 113. | 53.99 | 4.26 | 3.7 | | 53.98 | 4.25 | 3.63 | | 210 decom |
| 114. | 57.49 | 7.39 | 4.74 | | 57.72 | 7.57 | 4.43 | | 80-83 |
| 115. | 65.5 | 7.9 | 4.77 | | 64.97 | 7.79 | 4.75 | | 90-92 |
| 116. | 65.5 | 7.9 | 4.77 | | 65.11 | 8.03 | 4.71 | | 125-127 |
| 117. | 71.26 | 8.3 | 4.2 | | 70.6 | 7.89 | 4.83 | | 94-96 |
| 118. | 56.29 | 4.17 | 7.72 | | 56.23 | 4.01 | 7.6 | | 173-175 |
| 119. | 47.89 | 3.81 | 3.29 | | 47.52 | 3.71 | 3.16 | | 236-237 |
| 120. | 55.7 | 6.55 | 13 | | 55.71 | 6.58 | 13.05 | | 123-5 |
| 121. | 57.98 | 5.81 | 7.95 | | 57.9 | 7.11 | 7.82 | | 131-133 |
| 122. | 51.74 | 5.5 | 4.02 | | 51.41 | 5.43 | 3.61 | | 118-119.5 |
| 123. | 41.22 | 4.38 | 3.2 | | 41.45 | 4.36 | 2.94 | | 143-144.5 |
| 124. | 57.06 | 6.06 | 4.44 | | 57.02 | 6.12 | 4.35 | | 57-58 |
| 125. | 61.18 | 4.83 | 4.2 | | 60.71 | 4.76 | 3.89 | | 214 decom |
| 126. | 55.55 | 6.22 | 8.64 | | 55.4 | 6.24 | 8.53 | | 150-151 |
| 127. | 65.17 | 4.83 | 4.47 | | 65.27 | 4.87 | 4.48 | | 208-209 |
| 128. | 73.03 | 8.99 | 4.06 | | 72.92 | 9.36 | 4.1 | | 99-101 |
| 129. | 72.25 | 5.44 | 4 | | 72.14 | 5.24 | 4.01 | | 216-217 |
| 130. | 52.56 | 5.58 | 8.17 | | 52.66 | 5.44 | 8.21 | | 96-100 |
| 131. | 56.28 | 6.41 | 9.38 | | 56.32 | 6.42 | 9.28 | | 98-100 |
| 132. | 52.56 | 5.58 | 8.17 | | 52.46 | 5.65 | 7.86 | | 150-153 |
| 133. | 69.89 | 4.89 | 4.53 | | 69.64 | 5 | 4.54 | | 136-9 |
| 134. | 71.68 | 5.2 | 4.2 | | 71.24 | 5.1 | 4.13 | | 251-253 |

TABLE 1-continued

| | Carrier Properties | | | | | | | | |
|---|---|---|---|---|---|---|---|---|---|
| | Anal. Calculated For | | | | Found | | | | Melting Point |
| Compound | C | H | N | S | C | H | N | S | (° C.) |
| 135. | 65.64 | 5.78 | 4.25 | | 65.3 | 5.91 | 4.04 | | 79-83 |
| 136. | 33.92 | 3.61 | 2.64 | | 34.48 | 3.84 | 2.48 | | 164-165 |
| 137. | 57.06 | 6.06 | 4.44 | | 57.09 | 6.17 | 4.45 | | 88-89 |
| 138. | 69.79 | 7.69 | 5.09 | | 69.68 | 7.78 | 5.08 | | 102-3 |
| 139. | 69.28 | 7.04 | 4.25 | | 68.99 | 7 | 4.1 | | 107-108 |
| 140. | 66.42 | 6.62 | 4.84 | | 66.2 | 6.49 | 4.81 | | 88-9 |
| 141. | 58.62 | 6.76 | 4.27 | | 58.66 | 6.93 | 4.18 | | 134-135 |
| 142. | 63.38 | 7.21 | 5.28 | | 63.22 | 7.28 | 5.24 | | 71-73 |
| 143. | 56.29 | 4.17 | 7.72 | | 56.19 | 4.04 | 7.65 | | 156-160 |
| 144. | 71.13 | 7.88 | 3.77 | | 70.39 | 7.91 | 3.64 | | 95-97 |
| 145. | 58.44 | 6.06 | 8.02 | | 58.25 | 6.38 | 7.84 | | 165-8 |
| 146. | 54.22 | 5.79 | 5.75 | | 54.26 | 5.65 | 5.69 | | 77-78.5 |
| 147. | 54.22 | 5.79 | 5.75 | | 54.21 | 5.85 | 5.61 | | 80-81 |
| 148. | 58.78 | 4.93 | 40.3 | | 58.64 | 4.89 | 3.97 | | 172-173 |
| 149. | 56.19 | 4.72 | 3.85 | | 56.31 | 4.67 | 3.86 | | 177 |
| 150. | 66.46 | 4.65 | 4.31 | | 66.41 | 4.56 | 4.23 | | 158-160 |
| 151. | 58.61 | 7.24 | 5.69 | | 58.79 | 7.35 | 5.66 | | |
| 152. | 54.22 | 5.79 | 5.75 | | 54.21 | 5.72 | 5.62 | | 54-55 |
| 153. | 60.85 | 4.25 | 7.89 | | 60.27 | 4.37 | 7.89 | | >260 |
| 154. | 62.5 | 7.3 | 10.14 | | 64.77 | 7.27 | 9.9 | | 187-190 |
| 155. | 55.4 | 6.5 | 3.6 | | 55.56 | 6.51 | 3.5 | | 114-116 |
| 156. | 45.85 | 4.9 | 4.86 | | 46.06 | 4.78 | 4.71 | | 67-68 |
| 156. | 48.8 | 4.7 | 4.4 | | 48.81 | 4.64 | 4.39 | | 144-146 |
| 157. | 50.3 | 5.1 | 4.2 | | 50.25 | 5.12 | 3.99 | | 141-143 |
| 158. | 55.5 | 4.1 | 3.8 | | 55.55 | 3.88 | 3.75 | | 190-192 |
| 159. | 64.97 | 6.9 | 5.05 | | 64.7 | 6.82 | 5.02 | | 171-174 |
| 160. | 54.3 | 3.7 | 4 | | 54.31 | 3.58 | 3.83 | | 222-224 |
| 161. | 56.4 | 6.7 | 3.5 | | 56.69 | 6.98 | 3.11 | | 76-78 |
| 162. | 63.63 | 6.47 | 5.3 | | 64.76 | 6.84 | 4.74 | | 188-191 |
| 163. | 48.91 | 4.48 | 5.19 | | 48.89 | 4.31 | 5.10 | | 88.5-90 |
| 164. | 66.66 | 10.04 | 5.18 | | 66.69 | 10.77 | 5.16 | | 67.5-70.5 |
| 165. | 39.42 | 4.21 | 4.18 | | 39.19 | 4.35 | 3.88 | | oil |
| 166. | 53.05 | 5.19 | 5.16 | | 53.06 | 5.03 | 4.86 | | 151-152 |
| 167. | 65.53 | 7.85 | 4.78 | | 65.4 | 7.84 | 4.57 | | 85-89 |
| 168. | 68.99 | 6.11 | 4.47 | | 68.62 | 5.87 | 4.49 | | 162-6 |
| 169. | 69.71 | 6.47 | 4.28 | | 69.67 | 6.58 | 4.50 | | 132.5-135 |
| 170. | 61.21 | 7.53 | 9.52 | | 61.21 | 7.68 | 9.46 | | 134-135 |
| 171. | 62.14 | 7.44 | 4.53 | | 61.96 | 7.52 | 4.57 | | 101-104 |
| 172. | 58.63 | 6.71 | 6.22 | | 58.15 | 6.83 | 6.04 | | |
| 173. | 52.96 | 3.26 | 4.12 | | 52.96 | 3.28 | 4.02 | | 225-227 |
| 174. | 57.42 | 6.42 | 4.46 | | 57.3 | 6.38 | 4.39 | | 119-120 |
| 175. | 68.99 | 6.11 | 4.47 | | 68.84 | 6.08 | 4.51 | | 131-4 |
| 176. | 66.43 | 8.2 | 4.56 | | 66.42 | 8.16 | 4.51 | | 109-110 |
| 177. | 62.14 | 6.82 | 5.57 | | 61.96 | 6.66 | 5.52 | | 127-128 |
| 178. | 51.00 | 4.56 | 3.97 | | 51.09 | 4.61 | 3.93 | | |
| 179. | 67.36 | 5.30 | 4.90 | | 67.26 | 5.24 | 4.91 | | 185-186 |
| 180. | 66.43 | 8.20 | 4.56 | | 66.32 | 8.60 | 5.12 | | 51.5-55 |
| 181. | 69.92 | 6.79 | 8.58 | | 67.02 | 6.93 | 8.20 | | 81-84 |
| 182. | 66.46 | 8.14 | 4.56 | | 66.43 | 8.34 | 4.47 | | 82-84 |
| 183. | 62.13 | 4.89 | 22.64 | | 62.05 | 4.88 | 22.45 | | 271-272 |
| 184. | 68.16 | 7.32 | 6.36 | | 67.73 | 7.44 | 6.70 | | 114-117 |
| 185. | 71.30 | 5.98 | 5.73 | | 71.10 | 5.97 | 5.74 | | 146-149 |
| 186. | 68.16 | 7.32 | 6.36 | | 67.94 | 7.31 | 6.41 | | 105-108 |
| 187. | 65.51 | 7.90 | 4.77 | | 65.35 | 7.63 | 4.59 | | 102-103 |
| 188. | 64.50 | 7.58 | 5.01 | | 64.19 | 7.69 | 4.83 | | 133-134 |
| 189. | 64.5 | 7.58 | 5.01 | | 64.5 | 7.57 | 4.90 | | 116-118 |
| 190. | 61.15 | 7.71 | 3.97 | | 61.27 | 7.79 | 4.08 | | 124-127 |
| 191. | 65.5 | 7.9 | 4.77 | | 65.32 | 7.94 | 4.7 | | 114-115 |
| 192. | 56.77 | 6.51 | 8.28 | | 56.83 | 6.76 | 8.21 | | 141-143 |
| 193. | 60.29 | 4.74 | 8.79 | | 60.17 | 4.58 | 8.74 | | 202-205 |
| 194. | 48.8 | 4.7 | 4.4 | | 48.81 | 4.64 | 4.39 | | 144-146 |

These carrier compounds or poly amino acids, and peptides, including the amino acids, may be used to deliver active agents including, but not limited to, biologically or chemically active agents such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g. an ester, anhydride, or an anhydride linkage.

Peptides are two or more amino acids joined by a peptide bond. Peptides can vary in length from dipeptides with two amino acids to poly peptides with several hundred amino acids. See *Chambers Biological Dictionary*, editor Peter M. B. Walker, Cambridge, England: Chambers Cambridge, 1989, page 215. Special mention is made of di-peptides, tri-peptides, tetra-peptides, and penta-peptides.

Salts such as, for example, sodium salt of these carrier compounds can be used as well.

Many of the compounds described herein are derived from amino acids.

Many of the compounds of the present invention can be readily prepared from amino acids including, but not limited to, aminocaprylic acid, butyrylhydroxaminic acid, aminophenylbutyric acid, aminophenylhexanoic acid, aminophenylpropionic acid, amino salicylic acid, aminophenylsuccinic acid, aminononanic acid, aminonicotinic acid, amino valenic acid, aminophenylacetic acid, aminocaproic acid, aminoundecanoic acid, aminoheptanoic acid, aminohydroxybenzoic acid, and aminodecanoic acid by methods within the skill of those in the art based upon the present disclosure and the methods described in U.S. patent application Ser. Nos. 60/017,902, filed Mar. 29, 1996; 08/414,654, filed Mar. 31, 1995; 08/335,148, filed Oct. 25, 1994; and 60/003,111, filed Sep. 1, 1995.

For example, these compounds may be prepared by reacting the single acid with the appropriate agent which reacts with free amino moiety present in the amino acids to form amides. Protecting groups may be used to avoid unwanted side reactions as would be known to those skilled in the art.

The carrier compound may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0-500 mM sodium chloride gradient is employed.

Delivery Systems

The compositions of the present invention may include one or more active agents.

In one embodiment, compounds or salts of compounds 1-193 or poly amino acids or peptides that include at least one of these compounds or salts may be used directly as a delivery carrier by simply mixing one or more compound or salt, poly amino acid or peptide with the active agent prior to administration.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent is an amount effective to accomplish the purpose of the particular active agent. The amount in the composition typically is a pharmacologically, biologically, therapeutically, or chemically effective amount. However, the amount can be less than a pharmacologically, biologically, therapeutically, or chemically effective amount when the composition is used in a dosage unit form, such as a capsule, a tablet or a liquid, because the dosage unit form may contain a multiplicity of carrier/biologically or chemically active agent compositions or may contain a divided pharmacologically, biologically, therapeutically, or chemically effective amount. The total effective amounts can then be administered in cumulative units containing, in total, pharmacologically, biologically, therapeutically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers provides extremely efficient delivery, particularly in oral, intranasal, sublingual, intraduodenal, or subcutaneous systems. Therefore, lower amounts of biologically or chemically active agent than those used in prior dosage unit forms or delivery systems can be administered to the subject, while still achieving the same blood levels and therapeutic effects.

The amount of carrier in the present composition is a delivery effective amount and can be determined for any particular carrier or biologically or chemically active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil; or any combination thereof.

Administration of the present compositions or dosage unit forms preferably is oral or by intraduodenal injection.

The delivery compositions of the present invention may also include one or more enzyme inhibitors. Such enzyme inhibitors include, but are not limited to, compounds such as actinonin or epiactinonin and derivatives thereof. These compounds have the formulas below:

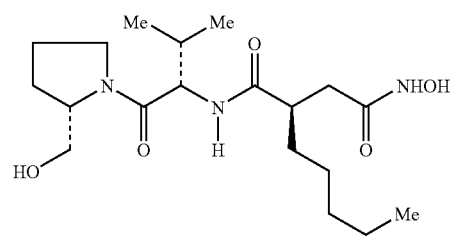

Actinonin

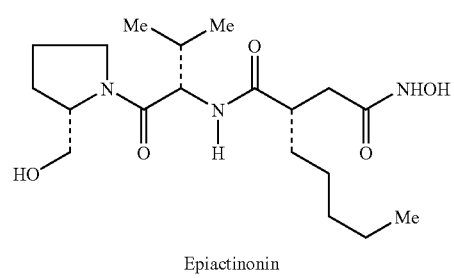

Epiactinonin

Derivatives of these compounds are disclosed in U.S. Pat. No. 5,206,384. Actinonin derivatives have the formula:

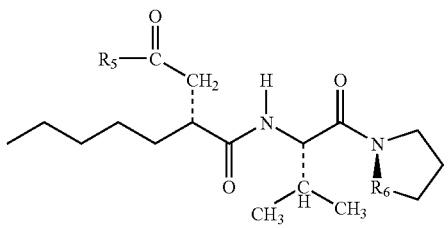

wherein $R^5$ is sulfoxymethyl or carboxyl or a substituted carboxy group selected from carboxamide, hydroxyaminocarbonyl and alkoxycarbonyl groups; and $R^6$ is hydroxyl, alkoxy, hydroxyamino or sulfoxyamino group. Other enzyme inhibitors include, but are not limited to, aprotinin (Trasylol) and Bowman-Birk inhibitor.

The compounds and compositions of the subject invention are useful for administering biologically or chemically active agents to any animals such as birds; mammals, such as primates and particularly humans; and insects. The system is particularly advantageous for delivering chemically or biologically or chemically active agents which would otherwise be destroyed or rendered less effective by conditions encountered before the active agent hits the target zone (i.e. the area in which the active agent of the delivery composition are to be released) and within the body of the animal to which they are administered. Particularly, the compounds and compositions of the present invention are useful in orally administering active agents, especially those which are not ordinarily orally deliverable.

DESCRIPTION OF THE PREFERRED EMBODIMENTS

The following examples illustrate the invention without limitation. All parts are given by weight unless otherwise indicated.

Example 1

Carrier Preparation

General Preparations of Carriers. The following procedures were used to prepare the compounds described herein. Many of the compounds were prepared by reaction of the appropriate amino acid with the appropriate acid chloride. The preparation of compound 79 is given as a representative example of the compounds prepared in this manner.

Preparation of Compound 79. Method A. A 1 L round bottom flask fitted with a magnetic stirrer was charged with 3-(4-aminophenyl)propionic acid (46.3 g, 0.28 moles, 1.17 equiv.) and 2 M aqueous sodium hydroxide (300 mL). 2,3-dimethoxybenzoylchloride (48.0 g, 0.24 moles, 1.00 equiv.) was added portionwise over 1 h to the stirred solution. After the addition, the reaction was stirred for 2.5 h at ambient temperature, and the pH of the solution was kept at ca 10 by the addition of 10M sodium hydroxide. The solution was then acidified with 1 M hydrochloric acid (3×100 mL), water (100 mL), and air dried. It was redissolved in boiling acetone (ca 500 mL), decolorized with activated charcoal (3 g), and filtered. Water (1.5 L) was added to the filtrate to induce the formation of a brown oil. The brown oil solidified upon stirring at room temperature for 10 min. The crude solid was collected by filtration and recrystallized from 70% methanol-water (v/v) to afford compound 79 as a tan solid (39.5) g, 50%).

Compounds 1, 5, 30, 31, 33, 36, 53-66, 68, 69, 71-74, 78, 80-88, 95, 97-99, 102, 108-110, 112-115, 119, 121-126, 136, 137, 139, 141, 144, 146, 147, 151, 152, 155-158, 160, 161, 163, 165, 166, 170, 172-174, 176, 177, 184-186, 188, 189, 191 and 192 were also prepared by this process.

Preparation of Compound 79. Method B. A 2 L three-neck round bottom flask was fitted with a magnetic stirrer and two addition funnels under an argon atmosphere. A suspension of 3-(4-aminophenyl)propionic acid (46.3 g, 0.28 moles, 1.17 equiv.) in ethyl acetate (700 mL) was added to the flask. A solution of 2,3-dimethoxybenzoylchloride (48.0 g, 0.24 moles, 1.00 equiv.) in ethyl acetate (250 mL) was charged to one of the addition funnels and added dropwise over 1 h. Triethylamine (28.20 g, 0.28 moles, 1.00 equiv.) was subsequently charged to the second funnel and added dropwise over 15 min. The reaction was stirred at ambient temperature for 3 h, and the solvent was evaporated in vacuo giving a residual brown oil. Water (600 mL) was added to the residue followed by sodium hydroxide (2 M, 500 mL), and the mixture was stirred at ambient temperature for 3 hours. The resultant brown solution was acidified with 2 M hydrochloric acid (ca 1 L). After cooling the mixture in an ice bath for 1 h, a yellow solid formed and was collected by filtration. The solid was washed with water (3×1.5 L) and recrystallized from 50% ethanol-water (v/v) to give compound 79 as a tan solid (59.2 g, 68%).

Compounds 18, 32, 37, 41, 168, 175, and 183 were also prepared by this process.

Preparation of Compound 79. Method C. A 2 L round bottom flask equipped with a magnetic stirrer and a reflux condenser was charged with a suspension of 3-(4-aminophenyl)propionic acid (46.3 g, 0.28 moles, 1.17 equiv.) in dichloromethane (560 mL). Chlorotrimethylsilane (62.36 g, 0.57 moles, 2.05 equiv.) was added in one portion, and the mixture was heated to reflux for 1 h under argon. The reaction was allowed to cool to room temperature and was placed in an ice bath (internal temperature<10° C.). The reflux condenser was replaced with an addition funnel containing triethylamine (42.50 g, 0.42 moles, 1.50 equiv.). The triethylamine was added dropwise over 15 min, and a yellow solid formed during the addition. The funnel was replaced by another addition funnel containing a solution of 2,3-dimethoxybenzoylchloride (48.0 g, 0.24 moles, 1.00 equiv. in dichloromethane (100 mL). The solution was added dropwise over 30 min. The reaction was stirred in the ice bath for another 30 min and at ambient temperature for 1 h. The dichloromethane was evaporated in vacuo to give a brown oil. The brown oil was cooled in an ice bath, and an ice-cold solution of 2 M sodium hydroxide (700 mL) was added. The ice bath was removed, and the reaction was stirred for 2 h to afford a clear brown solution. The solution was acidified with 2 M sulfuric acid (400 mL) and stored at ca 5° C. for 1 hour. A yellow solid formed and was collected by filtration. The solid was washed with water (3×100 mL) and recrystallized from 50% ethanol-water (v/v) to afford compound 79 as tan needles (64.7 g, 82%).

Compounds 2-4, 6-17, 19-29, 34, 38-40, 42-48, 50-52, 67, 70, 75-77, 89-94, 96, 100, 101, 107, 111, 116-118, 127-132, 134, 135, 193, 142, 143, 148, 149, 159, 162, 164, 169, 178-182, 187, and 190 were also prepared by this process.

Preparation of Compound 35. A solution of O-acetylsalicyloyl chloride (24.68 g, 124 mmol, 1 equiv) in tetrahydrofuran (300 mL) was cooled in an ice bath. Triethylamine (25 g, 249 mmol, 2 equiv) was added dropwise via an additional funnel. The methyl 9-aminononanoate hydrochloride was dissolved in DMF (190 mL, slightly warm to dissolve), charged to an addition funnel and added dropwise to the above mixture. The reaction was stirred in the ice-bath for 20 min and a room temperature for 2 h. Evaporation of the THF under reduced pressure gave a pink DMF solution. The pink solution was cooled in an ice-bath, and 2 M aqueous sodium hydroxide (300 mL) was added. After being stirred at room temperature for 12 h, the mixture was acidified with 2 M hydrochloric acid (500 mL). The solution was cooled in an ice-bath, and a solid formed. The solid was collected by filtration and was recrystallized from 50% ethanol/water to give compound 35 (32 g, 87%) as an off-white solid.

Preparation of Compound 49. 1-(2-hydroxyphenyl)-3-(4-methylbenzoate)-1,3-propane dione (3.00 g, 0.0101 mil.) is placed in a 100 ml round bottomed flask fitted with argon purge, magnetic stir bar and cold water condenser. Glacial acetic acid (20 mls) and concentrated sulfuric acid (5 mls) were added, and heating of the reaction mixture was initiated. The reaction mixture was allowed to heat at a reflux for 6 h before heating was discontinued. The reaction mixture was allowed to come to room temperature, and then was poured in 100 mls of ice/water. This was stirred for approximately ½ h before the mixture was filtered, and a brown solid was isolated. The brown solid was recrystallized twice from acetic acid, yielding compound 49 as a tan solid (1.44 g, 53.8%).

Preparation of Compound 167. 2-coumaranone (4.21 g, 0.0314 mol) was dissolved, with stirring, in acetonitrile (75 mls) in a 250 ml round bottomed flask fitted with a magnetic stir bar, argon purge and cold water condenser. Triethylamine (3.18 g, 0.0314 mol) and 8-aminocaprylic acid (5.00 g, 0.0314 mol) were added, and a tan slurry was formed. Heating was started, and the reaction mixture was allowed to reflux overnight. After heating overnight, thin layer chromatography of the reaction mixture (50% ethyl acetate/50% hexane) indicated that the reaction had gone to completion. Heating was stopped, the reaction mixture was allowed to cool to room temperature, and was concentrated in vacuo. The resulting residue was taken up in methylene chloride, and was washed with two, 100 ml portions of 1N hydrochloric acid solution. The methylene chloride layer was dried with sodium sulfate and was concentrated in vacuo. The resulting tan solid was allowed to dry in vacuo overnight, yielding compound 167 as a tan solid (8.35 g, 70.4%).

Preparation of Compound 171. 1,4-benzodioxan-2-one (3.93 g, 0.0262 mol) was dissolved, with stirring, in acetonitrile (70 mls) in a 250 ml round bottomed flask fitted with a magnetic stir bar, argon purge and cold water condenser. Triethylamine (2.64 g, 0.0262 mol) and 8-aminocaprylic acid (500 g, 0.0262 mol) were added and a tan slurry was formed. Heating was started, and the reaction mixture was allowed to reflux for approximately 3 hours. At this time, thin layer chromatography of the reaction mixture (50% ethyl acetate/50% hexane) indicated that the reaction had gone to completion. Heating was discontinued, and the reaction mixture was allowed to cool to room temperature and was concentrated in vacuo. The resulting residue was taken up in methylene chloride and was washed with a 100 ml portion of 1N hydrochloric acid solution. At this time, a tan solid was noted to precipitate, and it was isolated by filtration. This tan solid was washed further with an additional 100 ml portion of 1 N hydrochloric acid solution, and then with 100 ml of water. The resulting tan solid was allowed to dry in vacuo overnight yielding Compound 171 as a tan solid (7.73 g, 95.6%).

Preparation of Compound 120. A solution of 3.00 g (18.3 mmol) of 2-nitrophenylisocyanate and 5 mL of tetrahydrofuran was added dropwise over 10 min to an ice bath-cooled solution of 2.08 g (13.1 mmol) of 8-aminocaprylic acid, 1.40 mL of 10 N NaOH and 40 mL of water. The reaction mixture was stirred an additional 30 min, warmed to 25° C. and treated with 3% HCl solution until pH was 5. The yellow precipitate was filtered off and rinsed with 100 ml of water. The yellow solid was recrystallized in 2-propanol and water to give 3.7 g of compound 120 as pale yellow crystals.

Compounds 104-106 were also prepared by this procedure.

Preparation of Compound 133. A suspension of 2.40 g (16.3 mmol) and 2.80 g (15.6 mmol) of 4-(4aminophenyl)butyric acid in 20 mL of propylene glycol, 2.40 mL (1.74 g, 17.3 mmol) of triethylamine and 10 mg (0.08 mmol) of dimethylaminopyridine was heated to 140° C. The mixture became a clear solution after 5 min at 140° C. After stirring for 330 min, the reaction mixture was cooled to 25° C. and diluted with 20 mL of water. The solid phthalimide which had formed was filtered off. The filtrate was acidified with 3% HCl solution. The resulting solid was filtered off and was recrystallized from 2-propanol and water to give 0.62 g of compound 133 as a tan solid.

Preparation of Compound 138. A solution of 1.73 g (12.9 mmol) of phthalic dialdehyde, 2.04 g 8-aminocaprylic acid and 20 mL of acetic acid was heated to reflux for 10 min. The reaction mixture was cooled to 40° C., diluted with water and extracted with $CH_2Cl_2$ (2×20 mL). The organic phase was washed with water and brine, dried over $Na_2SO_4$ and evaporated. The residue was dissolved in ether and extracted with 2N NaOH. The layers were separated. The aqueous layer was made acidic with 3% HCl and extracted with $CH_2Cl_2$. The organic phase was dried over $Na_2SO_4$ and evaporated. The yellow residue was crystallized from acetonitrile and water to give 1.25 g of compound 138 as a yellow solid.

Preparation of Compound 140. A mixture of 1.40 g (9.48 mmol) of phthalic anhydride and 1.51 g (9.48 mmol) of 8-aminocaprylic acid was heated to 150° C. for 5 min. Upon cooling, 2.61 g of solid compound 140 was received.

Compound 150 was also prepared by this procedure.

Preparation of Compound 145. A suspension of 2.11 g (10.1 mmol) ethyl carbamoylanthranilic acid and 5 mL of $CH_2Cl_2$ was treated with 2.20 mL of oxalyl chloride. After stirring for 1 h the volatiles were stripped off. At that same time, a suspension of 1.60 g (10.1 mmol) of 8-aminocaprylic acid and 15 mL of $CH_2Cl_2$ was treated with 2.60 mL (2.23 g, 20.5 mmol) of TMSCl. This mixture was heated to reflux for 90 min, cooled in an ice bath and treated with 4.30 mL (3.12 g, 30.9 mmol) of triethylamine. Five min later, a slurry of the residue from the oxalyl chloride reaction in 20 mL of $CH_2Cl_2$ was added. The reaction mixture was warmed to 25° C. and stirred overnight. Upon acidification of the mixture with 3% HCl, a white solid formed. The solid was filtered off and recrystallized from EtOH and water to give 1.88 g of compound 145.

Compound 153 was also prepared by this procedure.

Preparation of Compound 154. A suspension of 4.02 g (25.6 mmol) of trans-4-aminomethylcyclohexane-carboxylic acid, 4.18 g (25.6 mmol) of isatoic anhydride, 20 mL of $CH_2Cl_2$, 20 mL of dioxane, and 4 mL of water was heated to reflux for 12 h. The solution was cooled to 25° C. and extracted with ether (4×20 mL). The organic layer was dried over $Na_2SO_4$ and concentrated. The resulting solid was recrystallized from EtOH and water to give 4.95 g of compound 154.

Compound 103 is available from Aldrich Chemical Company, Inc., Milwaukee, Wis.

Example 2

Parathyroid Hormone Dosing Solutions

Intracolonic ("IC") dosing compositions containing 100 mg/kg of carrier and 25 μg/kg of parathyroid hormone in 25% aqueous propylene glycol or oral gavage ("PO") dosing solution containing 400 mg/kg of carrier and 100 μg/kg of parathyroid hormone in water, were prepared with carriers 9, 33, 35, 77, 79, 109, 110, 123, 136, 141, and 169. The dosing solutions are designated P-carrier number-DS.

Comparative Example 2A

Parathyroid Hormone Dosing Solutions

An intracolonic dosing composition containing 100 mg/kg of a carrier having the formula

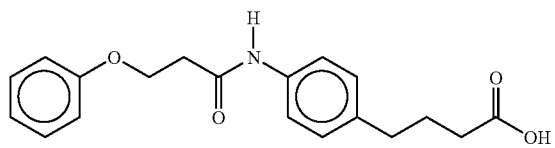

and 25 μg/kg of parathyroid hormone in 25% aqueous propylene glycol was prepared. The dosing solution is identified as P-9A-DS.

Examples 3

In Vivo Parathyroid Hormone Delivery

Male Sprague-Dawley rats weighing between 200-250 g were fasted for 24 hours and were administered ketamine (44 mg/kg) and chlorpromazine (1.5 mg/kg) 15 minutes prior to dosing. The rats were administered one of dosing solutions P-9-DS, P-33-DS, P-35-DS, P-77-DS, P-79-DS, and P-141-DS by oral gavage ("PO") or intra-colonic instillation ("IC"). Blood samples were collected serially from the tail artery for serum determination of parathyroid hormone concentration. Serum parathyroid hormone concentrations were quantified by a parathyroid hormone immunoaccuracy test host.

Results are illustrated in Table 2, below.

Comparative Example 3A

In Vivo Parathyroid Hormone Delivery

The procedure of Example 3 was followed substituting dosing solution P-9A-DS for dosing solution P-9-DS. Results are illustrated in Table 2, below.

Comparative Example 3B

In Vivo Parathyroid Hormone Delivery

The procedure of Example 3 was followed with a dosing solution (at a dose of 25 μg/kg of parathyroid hormone (intracolonic) or 100 μg/kg of parathyroid hormone (oral)), P-ØA-DS, that omitted the carrier.

Results are illustrated in Table 2, below.

TABLE 2

| In vivo Parathyroid Hormone Delivery | |
|---|---|
| Dosing Solution | Mean Peak Serum [PTH] ± Standard Deviation (pg/ml) |
| P-9-DS | 155 ± 105 (IC) |
| P-33-DS | 58 ± 18 (IC) |
| P-35-DS | 50 ± 27 (IC) |
| P-77-DS | 358 ± 274 (PO) |
| P-79-DS | 521 ± 128 (PO) |
| P-109-DS | 128 ± 25 (IC) |
| P-110-DS | 35 ± 11 (IC) |
| P-123-DS | 49 ± 22 (IC) |
| P-136-DS | 106 ± 72 (IC) |
| P-141-DS | 120 ± 120 (PO) |
| P-169-DS | 19 ± 33 (IC) |
| P-9A-DS | 116 ± 48 (IC) |
| P-ØA-DS | 11 ± 2 (PO), 27 ± 27 (IC) |

Example 4

Recombinant Human Growth Hormone Dosing Solutions

Intracolonic dosing compositions containing 25 mg/kg of carrier and 1 mg/kg of rHGH in phosphate buffer or oral gavage dosing solutions containing 600 mg/kg of carrier and 3 mg/kg of rHGH in phosphate buffer were prepared with carriers 9, 35, 36, 47, 62, 64, 67, 77, 79, 90, 94, 107, 109, 136, and 141.

The dosing solutions are designated R-carrier number-DS.

Comparative Example 4A

Recombinant Human Growth Hormone Dosing Solutions

An intracolonic dosing solution was prepared according to the procedure of Example 4, substituting a carrier having the formula

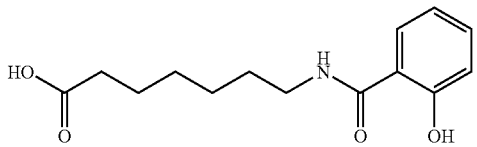 [SMILES: O=C(O)CCCCCCNC(=O)c1ccccc1O]

for the carrier. This dosing solution is designated as R-35A-DS.

Comparative Example 4B

Recombinant Human Growth Hormone Dosing Solutions

An intracolonic dosing solution was prepared according to the procedure of Example 4, substituting a carrier having the formula

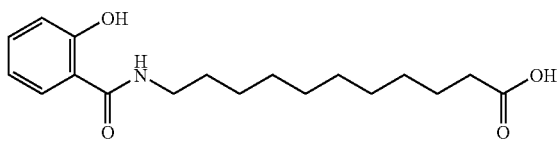 [SMILES: O=C(O)CCCCCCCCCCNC(=O)c1ccccc1O]

for the carrier. This dosing solution is designated as R-35B-DS.

Comparative Example 4C

Recombinant Human Growth Hormone Dosing Solutions

An intracolonic dosing solution was prepared according to the procedure of Example 4, substituting a carrier having the formula

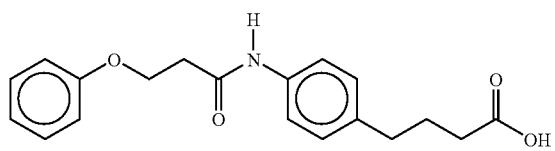

for the carrier. This dosing solution is designated as R-9A-DS.

Example 5

In Vivo Recombinant Human Growth Hormone Delivery

Male Sprague-Dawley rats weighing 200-250 g were fasted for 24 hours and administered ketamine (44 mg/kg) and chlorpromazine (1.5 mg/kg) 15 minutes prior to dosing. The rats were administered one of the dosing solutions of Example 3 by either oral gavage or intracolonic instillation. Blood samples were collected serially from the tail artery for determination of serum rHGH concentrations. Serum rHGH concentrations were quantified by an rHGH immunoassay test kit.

Results are illustrated in Table 3, below.

Comparative Example 5A

In Vivo Recombinant Human Growth Hormone Delivery

The procedure of Example 5 was followed, substituting the dosing solutions of Comparative Examples 3A-3C for the dosing solutions. Results are illustrated in Table 3, below.

Comparative Example 5B

In Vivo Recombinant Human Growth Hormone Delivery

The procedure of Example 5 was followed, with dosing solutions of active agent (at a dose of 1 mg of rHGH/kg (intracolonic) or 3 mg of rHGH/kg (oral)) and no carrier. These dosing solutions are designated R-ØD-DS and R-ØE-DS, respectively. Results are illustrated in Table 3, below.

TABLE 3

In Vivo Recombinant Human Growth Hormone Delivery

| Dosing Solution | Mean Peak Serum [rHGH] ± Standard Deviation (ng/ml) |
|---|---|
| R-9-DS | 125 ± 34 (IC) |
| R-35-DS | 41 ± 46 (PO) |
|  | 108 ± 56 (IC) |
| R-36-DS | 28 ± 11 (IC) |
| R-47-DS | 0 (IC) |
| R-62-DS | 11 ± 12 (IC) |
| R-64-DS | 72 ± 22 (PO) |
| R-67-DS | 19 ± 22 (PO) |
|  | 88 ± 24 (IC) |
| R-77-DS | 34 ± 10 (PO) |
| R-79-DS | 62 ± 51 (PO) |
| R-90-DS | 9 ± 13 (PO) |
| R-94-DS | 39 ± 35 (PO) |
| R-107-DS | 0 ± 0 (PO) |
| R-109-DS | 128 ± 25 (IC) |
| R-136-DS | 106 ± 72 (IC) |
| R-141-DS | 95 ± 14 (IC) |
| R-35A-DS | 17 ± 3 (IC) |
| R-35B-DS | 42 ± 28 (IC) |
| R-9A-DS | 55 ± 17 (IC) |
| R-ØD-DS | 0 ± 0 (IC) |
| R-ØE-DS | 0 ± 0 (IC) |

Example 6

In Vivo Interferon Delivery

An intracolonic dosing composition containing 50 mg/kg of carrier 9 and 250 µg/kg of interferon in 50% propylene glycol was prepared. Rats were administered the dosing composition by intracolonic instillation. Delivery was evaluated by use of an ELISA assay for human interferon α from Biosource, Inc. Mean peak serum interferon concentration was 2611±695.

Comparative Example 6A

In Vivo Interferon Delivery

Rats were administered, orally and by intracolonic instillation, dosing solutions of 1 mg/kg of interferon and no carrier. Delivery was evaluated according to the procedure of Example 6. Mean peak serum interferon concentration was 1951±1857 (PO) and 79±100 (IC).

Example 7

Heparin Dosing Solutions

Intracolonic dosing compositions containing 50 mg/kg of carrier and 25 mg/kg of heparin in 25% aqueous propylene glycol or oral gavage dosing solutions containing 300 mg/kg of carrier and 100 mg/kg of heparin in 25% aqueous propylene glycol were prepared with carriers 9, 35, 47, 50, 58, 62, 64, 67, 76, 96, 102, 109, 110, 111, 117, 122, 123, 139, 141, 144, and 169. The dosing solutions are designated H-carrier number-DS.

Comparative Example 7A

Heparin Dosing Solutions

Comparative intracolonic dosing compositions were prepared according to the procedure of Example 7, substituting the following carriers for the carrier.

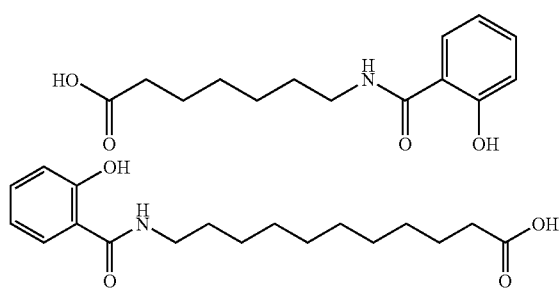

These dosing solutions are designated H-35A-DS, H-35B-DS, and H-109A-DS, respectively.

Examples 8

In Vivo Evaluation of Heparin in Rats

The dosing solutions of Example 7 were administered to fasted rats either by oral gavage or intracolonic instillation.

Blood samples were collected by cardiac puncture following the administration of ketamine (44 mg/kg). Heparin activity was determined by utilizing the activated partial thromboplastin time (APTT) according to the method of Henry, J. B., Clinical Diagnosis and Management by Laboratory Methods; Philadelphia, Pa.; W.B. Saunders (1979).

Results are in illustrated in Table 4, below.

Comparative Examples 8A

In Vivo Evaluation of Heparin in Rats

The dosing solutions of Comparative Example 7A were administered to fasted rats by intracolonic instillation. Blood samples were collected and heparin activity was determined by the method of Example 8.

Results are illustrated in Table 4, below.

Comparative Example 8B

In Vivo Evaluation of Heparin in Rats

An intracolonic dosing solution of 25 mg/kg of heparin and an oral gavage dosing solution of 100 mg/kg of heparin were administered to fasted rats. These dosage solutions were designated H-ØA-DS and H-ØB-DS, respectively.

Blood samples were collected, and heparin activity was determined by the methods of Example 8.

Results are illustrated in Table 4, below.

TABLE 4

| In Vivo Evaluation of Heparin in Rats | |
|---|---|
| Dosing Solution | Heparin APTT (sec) |
| H-9-DS | 48 ± 18 (IC) |
| H-35-DS | 54 ± 27 (PO), 177 ± 85 (IC) |
| H-47-DS | 30 ± 14 (IC) |
| H-50-DS | 40 ± 22 (IC) |
| H-58-DS | 24 ± 4 (IC) |
| H-62-DS | 37 ± 13 (IC) |
| H-64-DS | 59 ± 28 (PO), 168 ± 75 (IC) |
| H-67-DS | 76 ± 36 (IC) |
| H-76-DS | 63 ± 27 (PO) |
| H-96-DS | 36 ± 8 (IC) |
| H-102-DS | 111 ± 108 (IC) |

TABLE 4-continued

| In Vivo Evaluation of Heparin in Rats | |
|---|---|
| Dosing Solution | Heparin APTT (sec) |
| H-109-DS | 56 ± 28 (IC) |
| H-110-DS | 37 ± 9 (IC) |
| H-111-DS | 71 ± 39 (IC) |
| H-117-DS | 140 ± 128 (IC) |
| H-122-DS | 49 ± 21 (IC), 207 ± 7 (PO) |
| H-123-DS | 42 ± 14 (PO) |
| H-139-DS | 31 ± 11 (IC) |
| H-141-DS | 59 ± 26 (IC) |
| H-144-DS | 26 ± 3 (IC) |
| H-35A-DS | 61 ± 29 (IC) |
| H-35B-DS | 51 ± 30 (IC) |
| H-169-DS | 23 ± 2 (IC) |
| H-ØA-DS | 23 ± 2 (PO) |
| H-ØB-DS | 33 ± 6 (IC) |

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A compound selected from the group consisting of

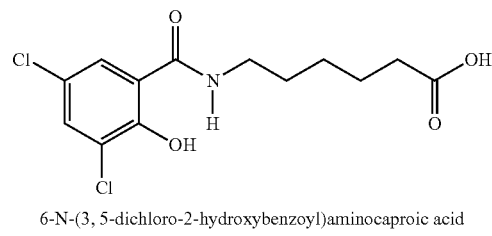

6-N-(3, 5-dichloro-2-hydroxybenzoyl)aminocaproic acid

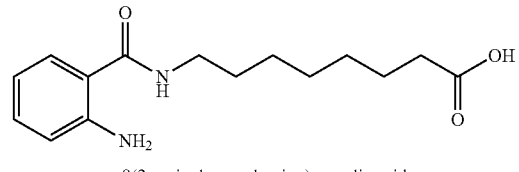

8(2-aminobenzoylamino)caprylic acid

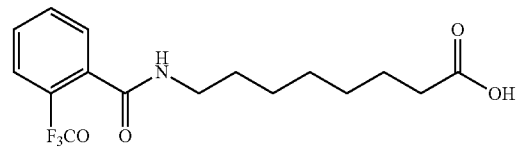

8(2-trifluoromethoxy)benzoylamino caprylic acid

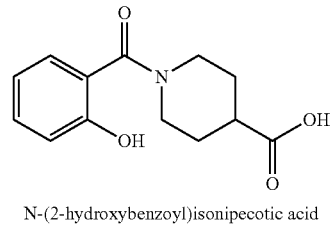

N-(2-hydroxybenzoyl)isonipecotic acid

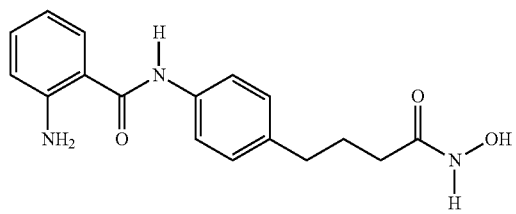
4-[4-(2-aminobenzoylamino)phenyl]butyrylhydroxamic acid

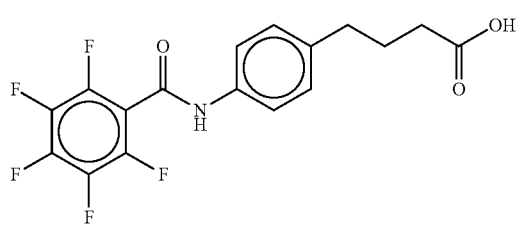
4-(4-(pentafluorobenzoyl)aminophenyl)butyric acid

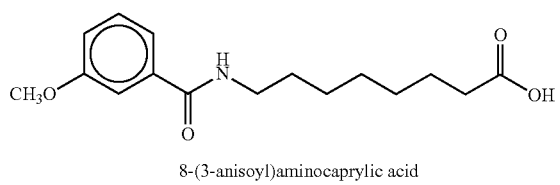
8-(3-anisoyl)aminocaprylic acid

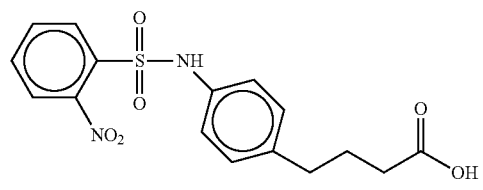
4-(4-(2-nitrobenzenesulfonyl)aminophenyl)butyric acid

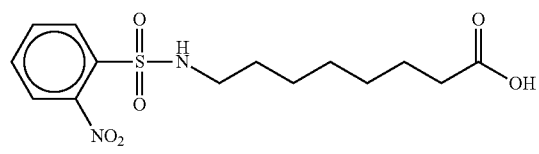
8-(2-nitrobenzenesulfonyl)aminocaprylic acid

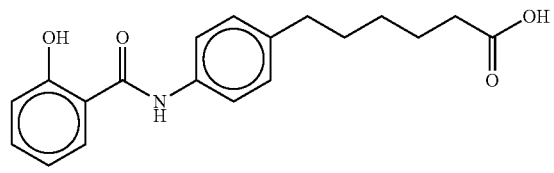
6-(4-(salicyloyl)aminophenyl)hexanoic acid

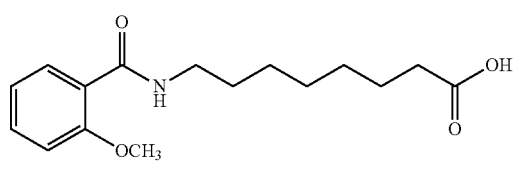
8-(2-methoxylbenzoyl)amino caprylic acid

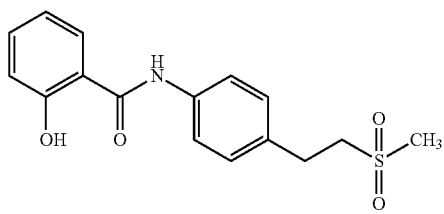
2-[4-Salicyloylamino)phenyl]ethyl methyl sulfone

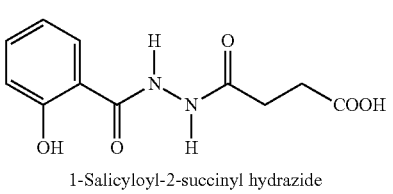
1-Salicyloyl-2-succinyl hydrazide

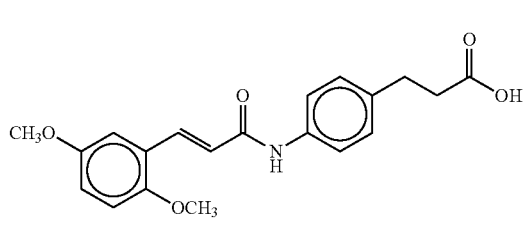
3-(4-(2,5-dimethoxycinnamoyl)aminophenyl)propionic acid

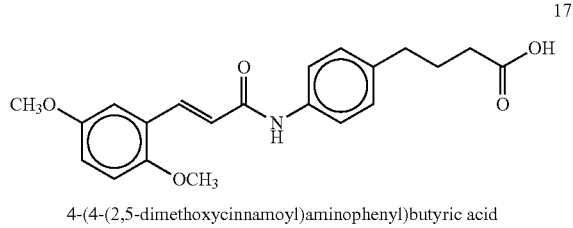
4-(4-(2,5-dimethoxycinnamoyl)aminophenyl)butyric acid

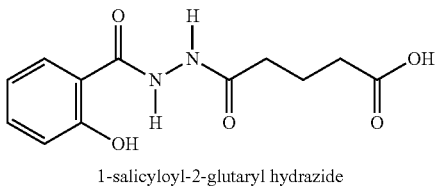
1-salicyloyl-2-glutaryl hydrazide

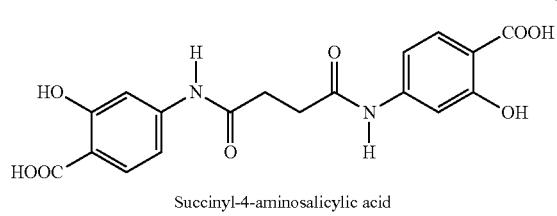
Succinyl-4-aminosalicylic acid

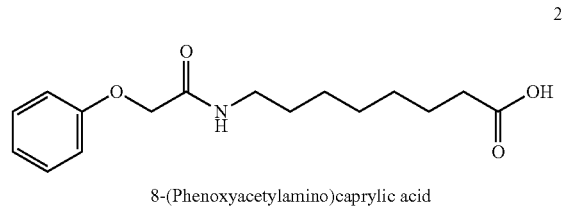
8-(Phenoxyacetylamino)caprylic acid

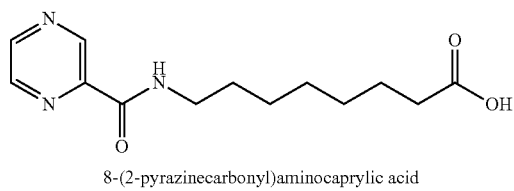
8-(2-pyrazinecarbonyl)aminocaprylic acid

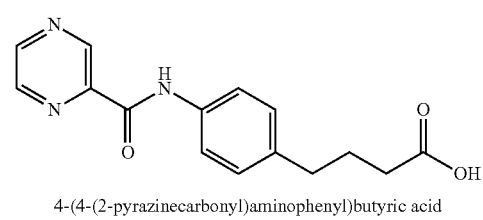
4-(4-(2-pyrazinecarbonyl)aminophenyl)butyric acid

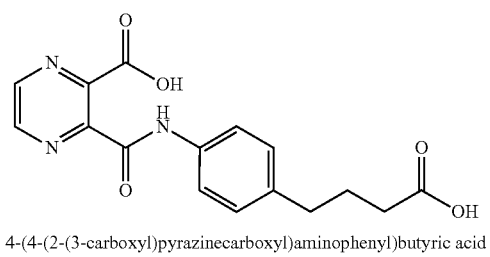
4-(4-(2-(3-carboxyl)pyrazinecarboxyl)aminophenyl)butyric acid

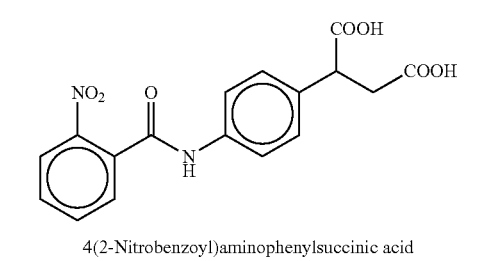
4(2-Nitrobenzoyl)aminophenylsuccinic acid

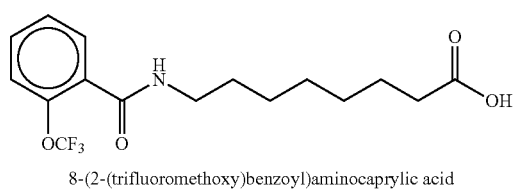
8-(2-(trifluoromethoxy)benzoyl)aminocaprylic acid

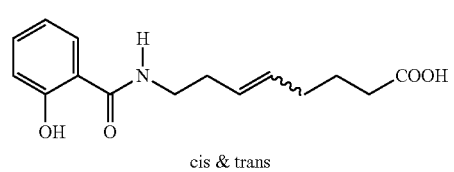
cis & trans

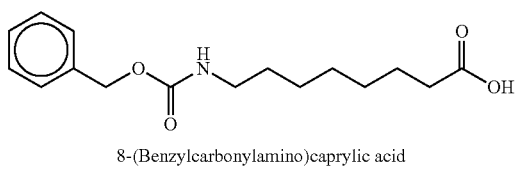
8-(Benzylcarbonylamino)caprylic acid

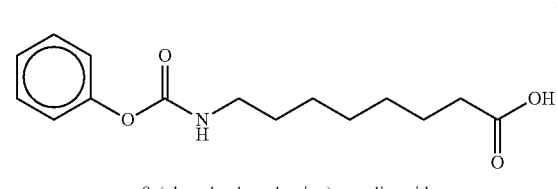
8-(phenylcarbonylamino)caprylic acid

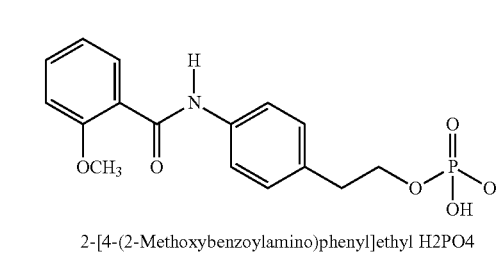
2-[4-(2-Methoxybenzoylamino)phenyl]ethyl H2PO4

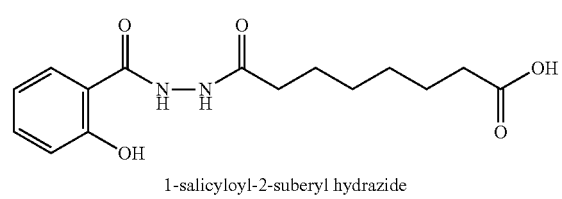
1-salicyloyl-2-suberyl hydrazide

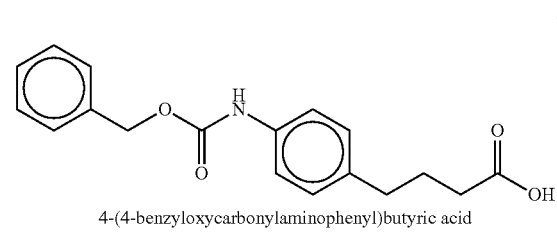
4-(4-benzyloxycarbonylaminophenyl)butyric acid

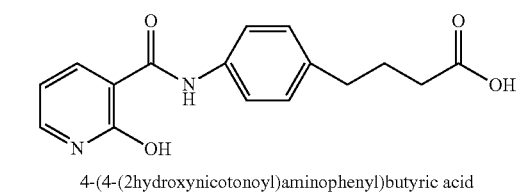
4-(4-(2hydroxynicotonoyl)aminophenyl)butyric acid

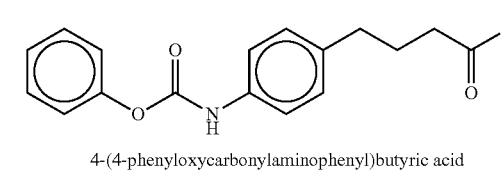
4-(4-phenyloxycarbonylaminophenyl)butyric acid

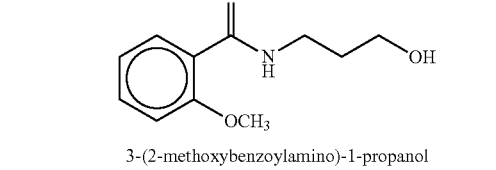
3-(2-methoxybenzoylamino)-1-propanol

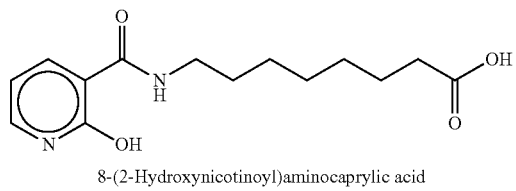
8-(2-Hydroxynicotinoyl)aminocaprylic acid

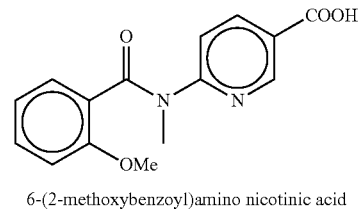
6-(2-methoxybenzoyl)amino nicotinic acid

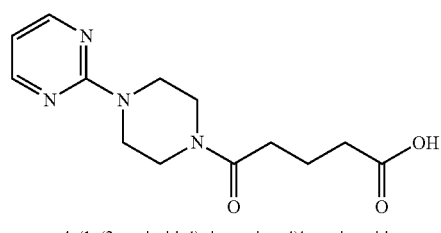
4-(1-(2-pyrimidyl)piperazinoyl)butyric acid

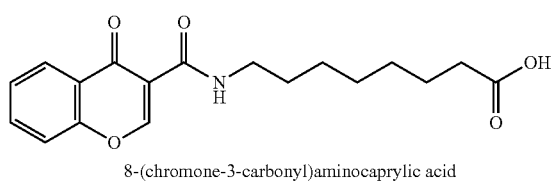
8-(chromone-3-carbonyl)aminocaprylic acid

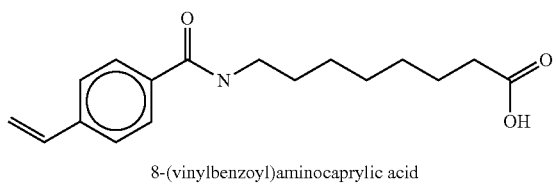
8-(vinylbenzoyl)aminocaprylic acid

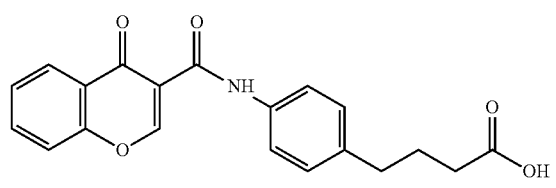
4-(4-chromone-3-carbonyl)aminophenyl)butyric acid

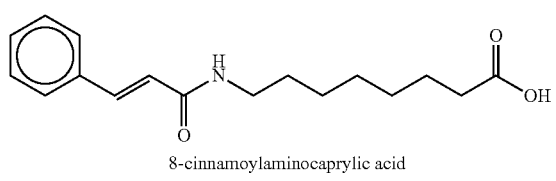
8-cinnamoylaminocaprylic acid

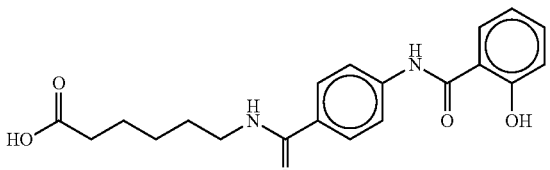
N-(4-salicylolyamino)-6-caproic acid

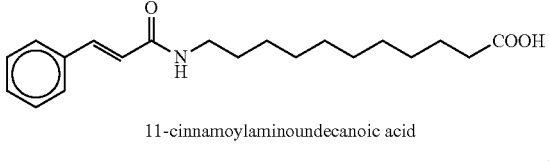
11-cinnamoylaminoundecanoic acid

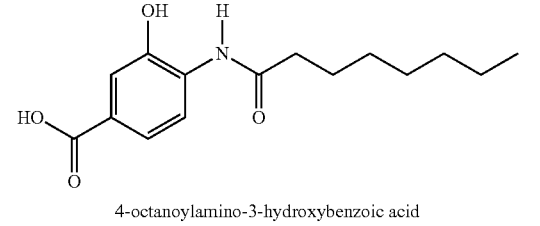
4-octanoylamino-3-hydroxybenzoic acid

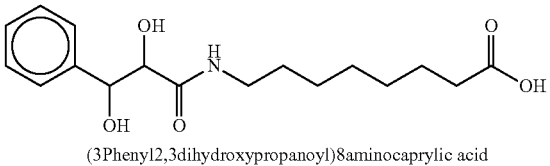
(3Phenyl2,3dihydroxypropanoyl)8aminocaprylic acid

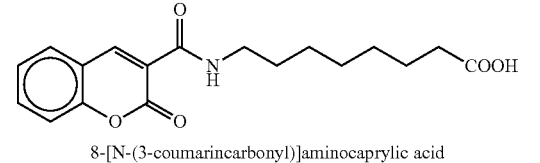
8-[N-(3-coumarincarbonyl)]aminocaprylic acid

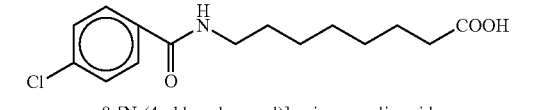
8-[N-(4-chlororbenzoyl)]aminocaprylic acid

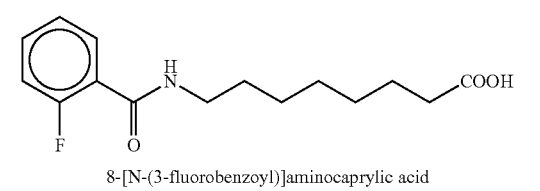
8-[N-(3-fluorobenzoyl)]aminocaprylic acid

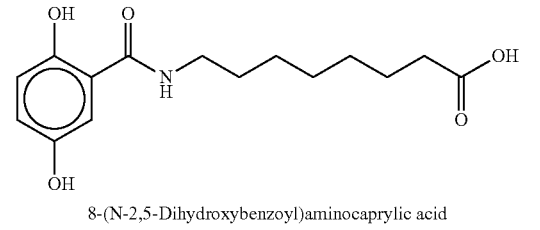
8-(N-2,5-Dihydroxybenzoyl)aminocaprylic acid

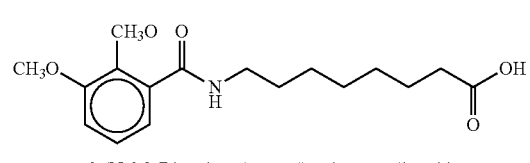
8-(N-2,3-Dimethoxybenzoyl)aminocaprylic acid

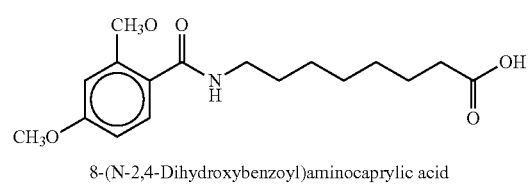
8-(N-2,4-Dihydroxybenzoyl)aminocaprylic acid

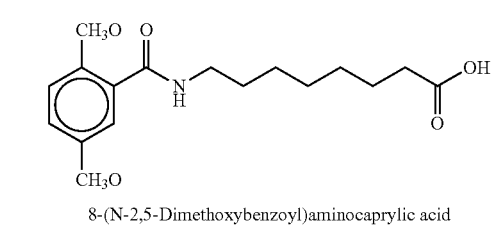
8-(N-2,5-Dimethoxybenzoyl)aminocaprylic acid

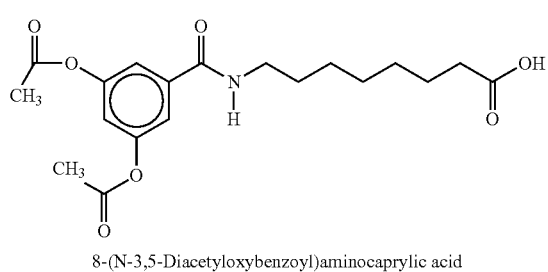
8-(N-3,5-Diacetyloxybenzoyl)aminocaprylic acid

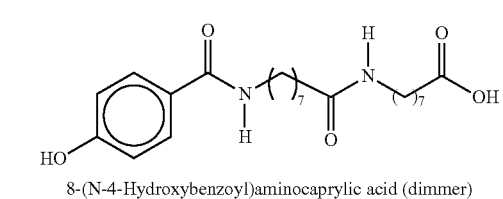
8-(N-4-Hydroxybenzoyl)aminocaprylic acid (dimmer)

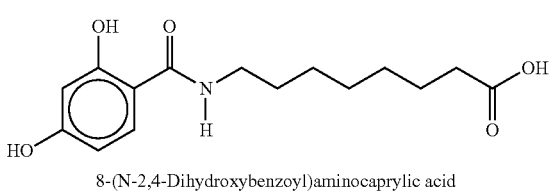
8-(N-2,4-Dihydroxybenzoyl)aminocaprylic acid

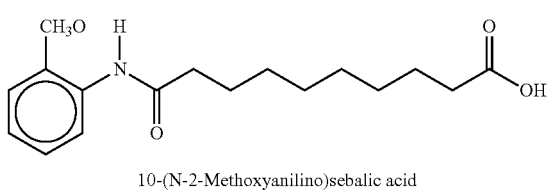
10-(N-2-Methoxyanilino)sebalic acid

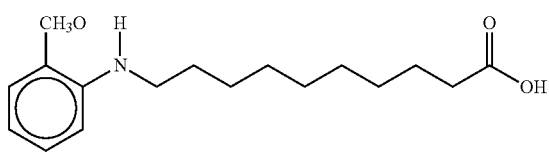
2-Methoxybenzenaminodecanoic acid

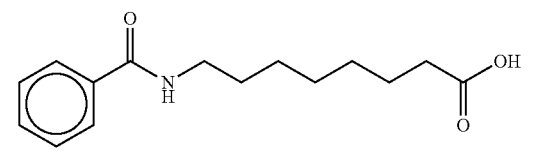
8-(N-benzoyl)aminocaprylic acid

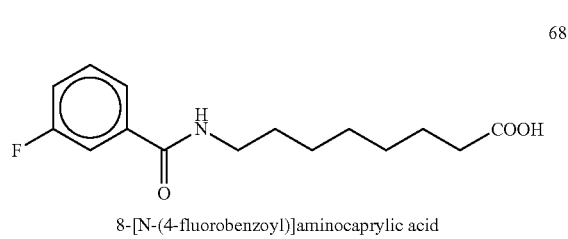
8-[N-(4-fluorobenzoyl)]aminocaprylic acid

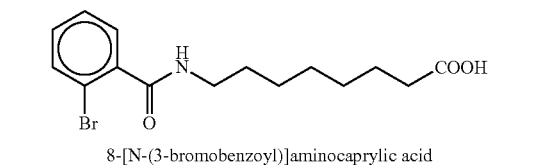
8-[N-(3-bromobenzoyl)]aminocaprylic acid

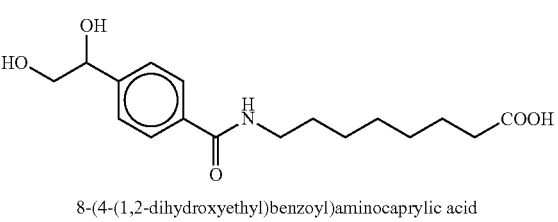
8-(4-(1,2-dihydroxyethyl)benzoyl)aminocaprylic acid

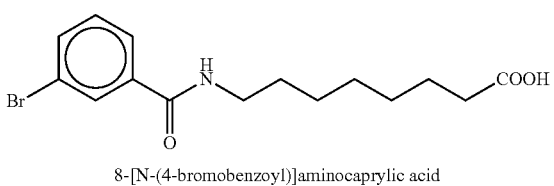
8-[N-(4-bromobenzoyl)]aminocaprylic acid

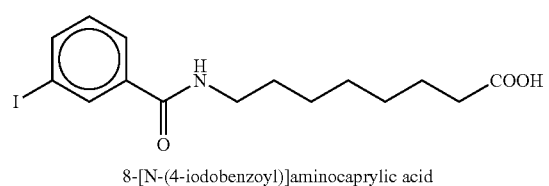
8-[N-(4-iodobenzoyl)]aminocaprylic acid

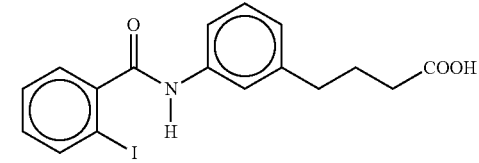
4-{4-[N-(2-iodobenzoyl)aminophenyl]}butyric acid

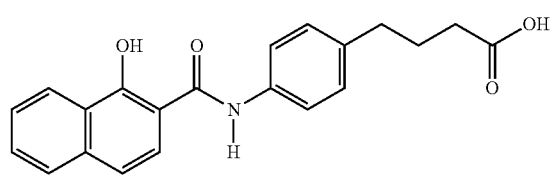
4-{4-[N-(1-hydroxy-2-naphtyoyl)aminophenyl]}butyric acid

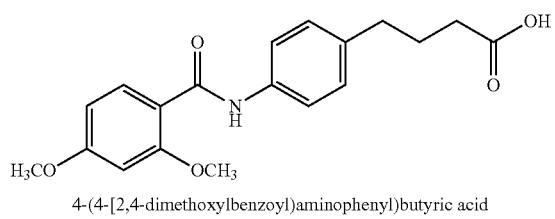
4-(4-[2,4-dimethoxylbenzoyl)aminophenyl)butyric acid

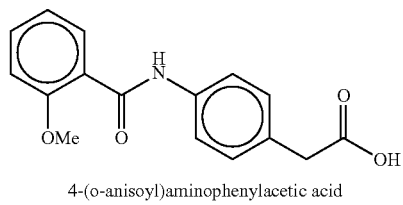
4-(o-anisoyl)aminophenylacetic acid

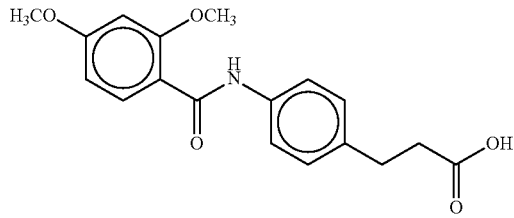
3-[4-(2,4-dimethoxybenzoyl)aminophenyl]propionic acid

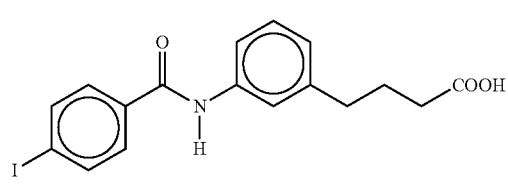
4-{4-[N-(4-iodobenzoyl)]aminophenyl}butyric acid

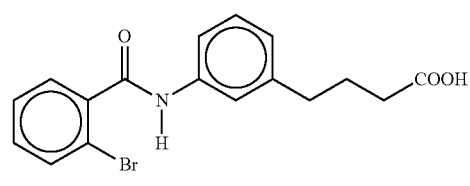
4-{4-[N-2-bromobenzoyl)]aminophenyl}butyric acid

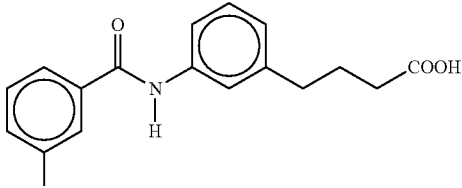
4-{4-[N-3-bromobenzoyl)]aminophenyl}butyric acid

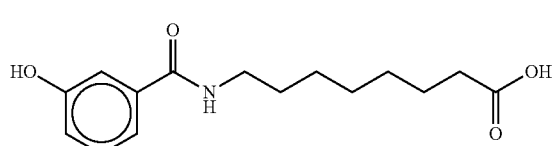
8-(N-3,5Dihyroxybenzoyl)aminocaprylic acid

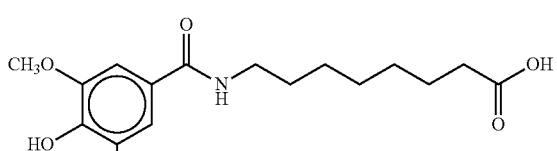
8-(N-3,5 Dimethoxy 4-hydroxybenzoyl)aminocaprylic acid

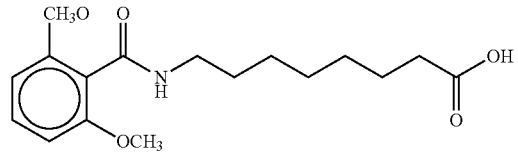
8-(N-2-6-Dimethoxybenzoyl)aminocaprylic acid

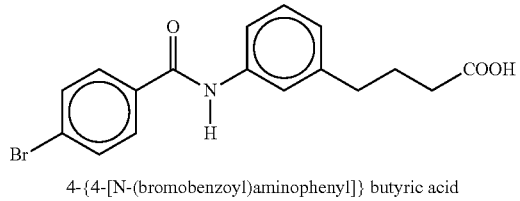
4-{4-[N-(bromobenzoyl)aminophenyl]} butyric acid

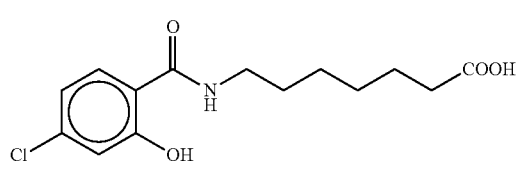
8-(2-hydroxy-4-chlorobenzoyl)aminocaprylic acid

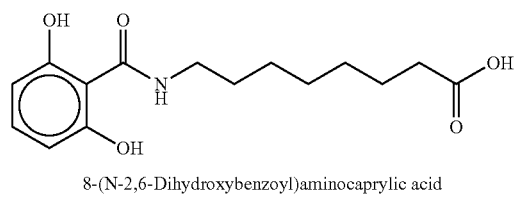
8-(N-2,6-Dihydroxybenzoyl)aminocaprylic acid

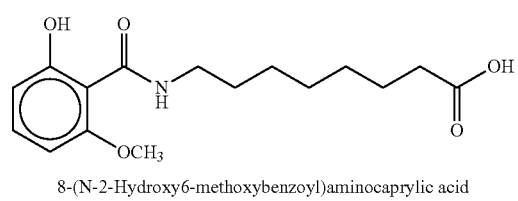
8-(N-2-Hydroxy6-methoxybenzoyl)aminocaprylic acid

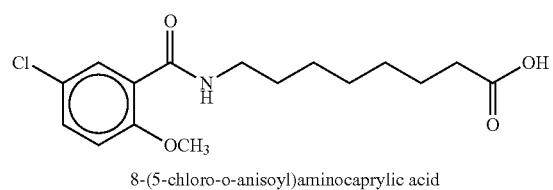
8-(5-chloro-o-anisoyl)aminocaprylic acid

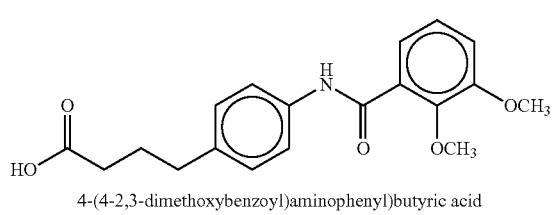
4-(4-2,3-dimethoxybenzoyl)aminophenyl)butyric acid

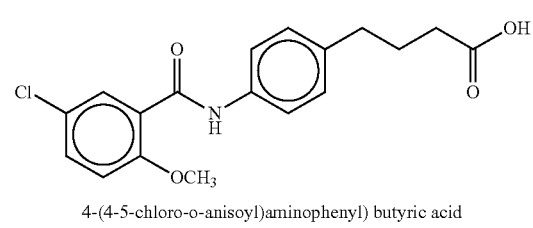
4-(4-5-chloro-o-anisoyl)aminophenyl) butyric acid

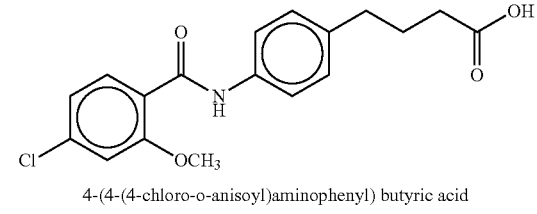
4-(4-(4-chloro-o-anisoyl)aminophenyl) butyric acid

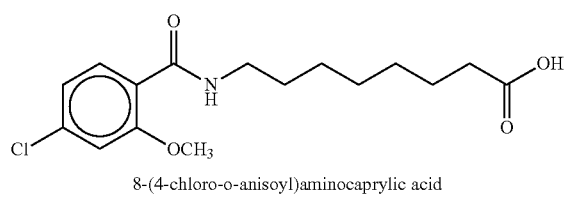
8-(4-chloro-o-anisoyl)aminocaprylic acid

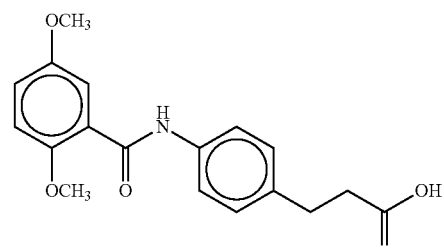
3-(4-(2,5-dimethoxybenzoyl)aminophenyl)propionic acid

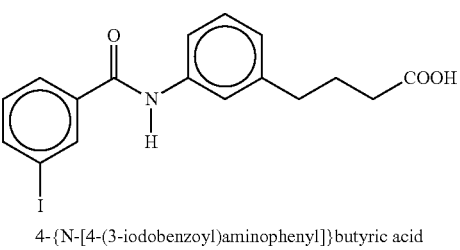
4-{N-[4-(3-iodobenzoyl)aminophenyl]}butyric acid

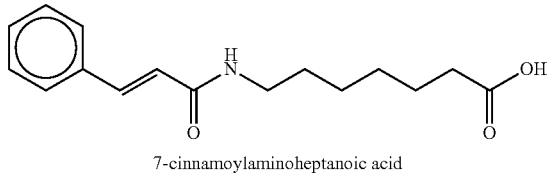
7-cinnamoylaminoheptanoic acid

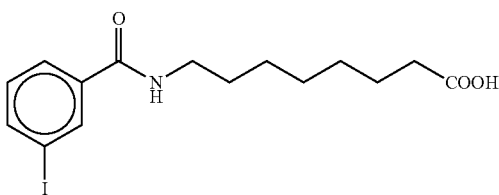
8-N-(3-iodobenzoyl)aminocaprylic acid

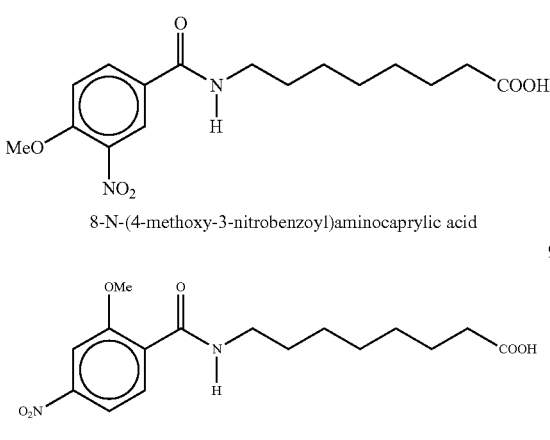
8-N-(4-methoxy-3-nitrobenzoyl)aminocaprylic acid

8-N-(2-methoxy-4-nitrobenzoyl)aminocaprylic acid

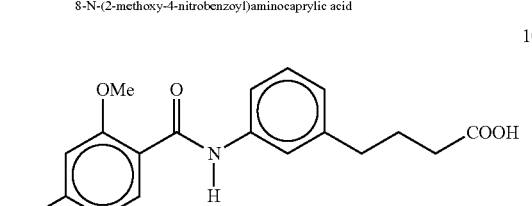
4-{N-[4-(2-methoxy-4-nitrobenzoyl)aminophenyl]}butyric acid

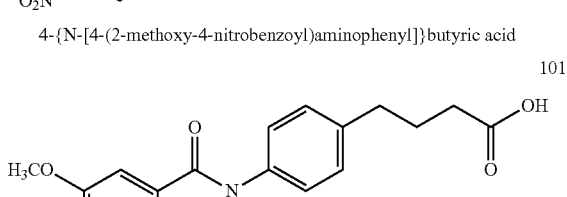
4-(4-(2,5-dimethoxybenzoyl)aminophenyl)butyric acid

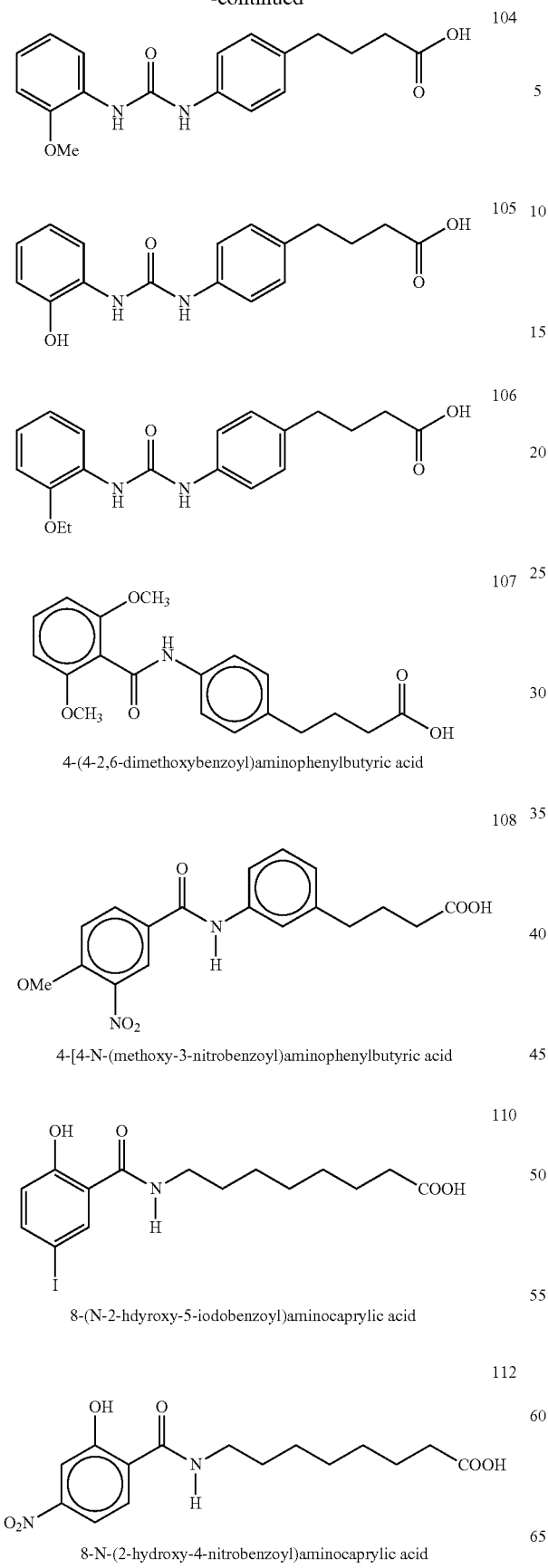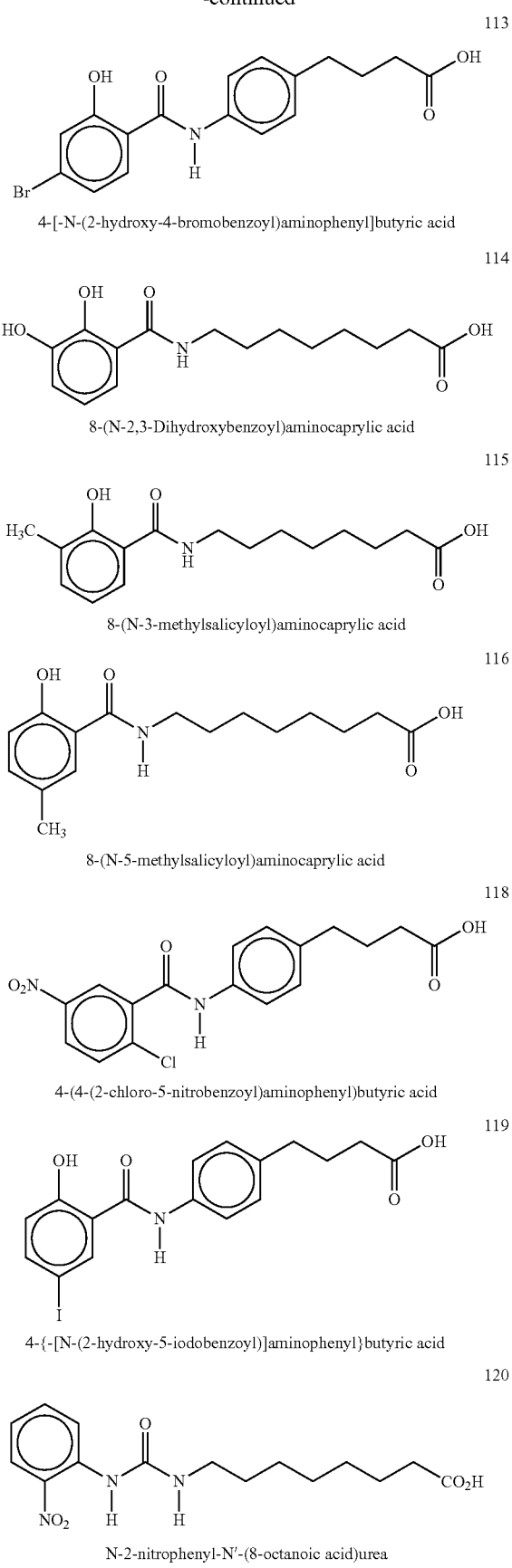

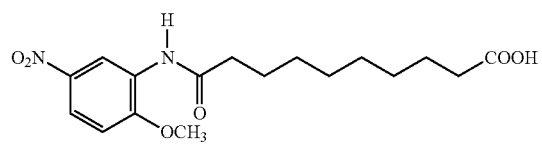
N-(2-methoxy-5-nitrophenyl)sebecoyl amid acid

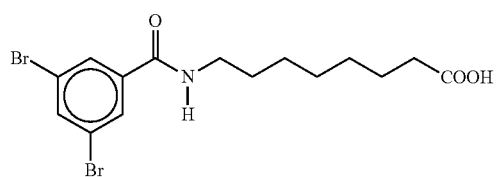
8-[N-(2-acetoxy-3,5-dibromobenzoyl)]aminocaprylic acid

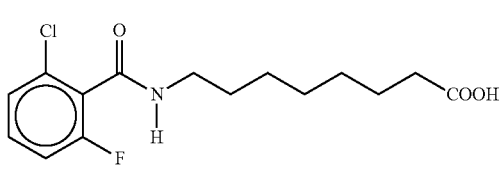
8-[N-(2-chloro-6-flurobenzoyl)]aminocaprylic acid

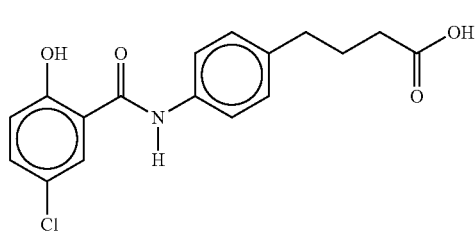

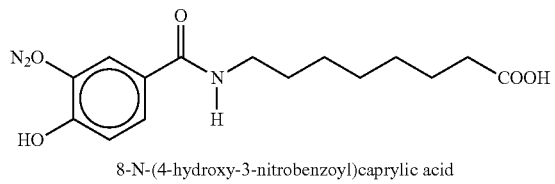
8-N-(4-hydroxy-3-nitrobenzoyl)caprylic acid

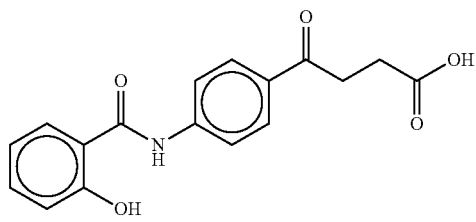
4-(4-Salicyloylmaminophenyl)-4-oxobutryic acid

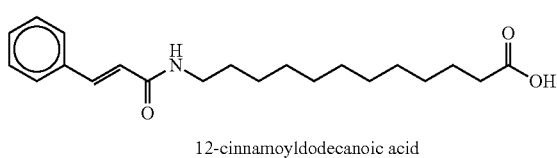
12-cinnamoyldodecanoic acid

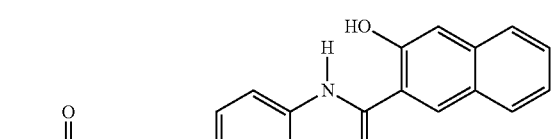
4-{4-[N-(3-hydroxy-2-napthoyl)aminophenyl]}butyric acid

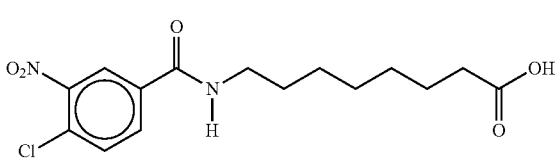
8-(4-chloro-3-nitrobenzoyl)aminocaprylic acid

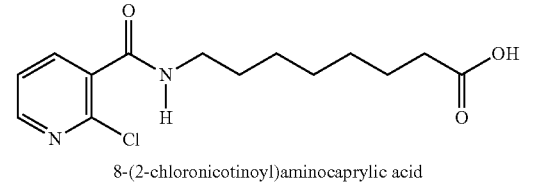
8-(2-chloronicotinoyl)aminocaprylic acid

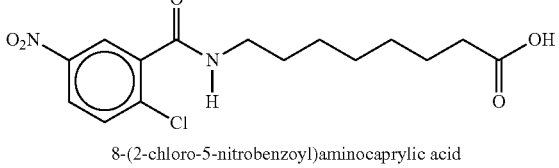
8-(2-chloro-5-nitrobenzoyl)aminocaprylic acid

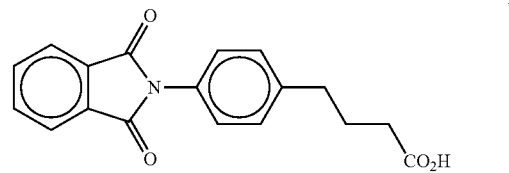
4-(4-phthalimidophenyl)butyric acid

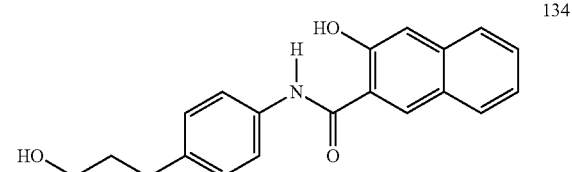
4-{4-N-(hydroxyl-2-napthoyl)aminophenyl]}propanoic acid

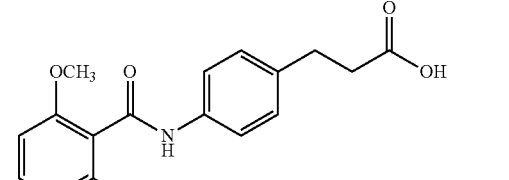
3-(4-(2,6-dimethoxybenzoyl)aminophenyl)propionic acid

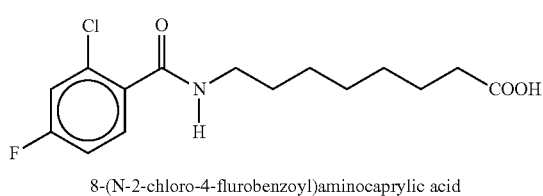
8-(N-2-chloro-4-flurobenzoyl)aminocaprylic acid
137

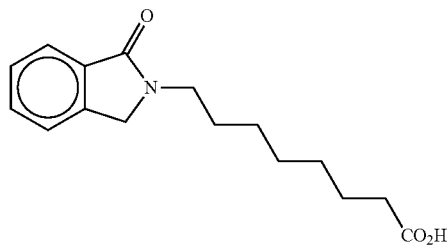
8-(2-(1,2-dihydroisoindole-1-one)octanoic acid
138

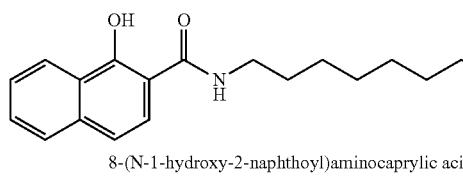
8-(N-1-hydroxy-2-naphthoyl)aminocaprylic acid
139

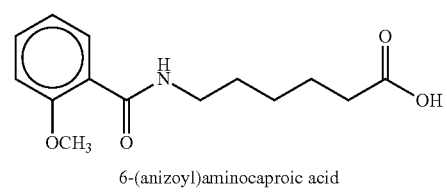
6-(anizoyl)aminocaproic acid
142

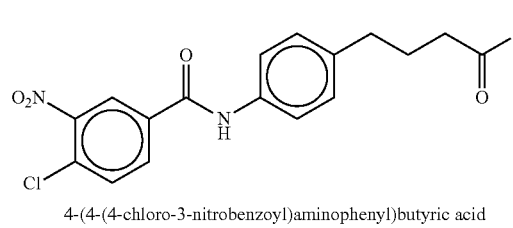
4-(4-(4-chloro-3-nitrobenzoyl)aminophenyl)butyric acid
143

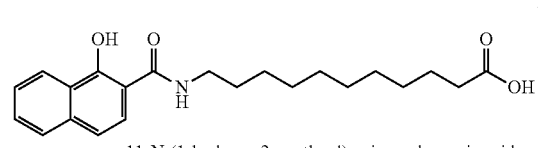
11-N-(1-hydroxy-2-napthoyl)aminoundecanoic acid
144

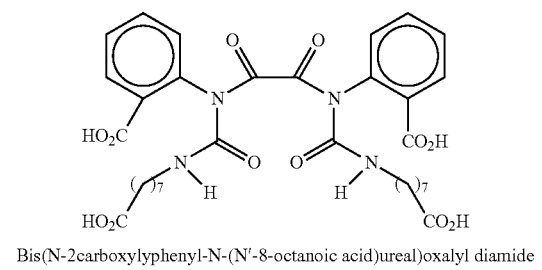
Bis(N-2carboxylyphenyl-N-(N′-8-octanoic acid)ureal)oxalyl diamide
145

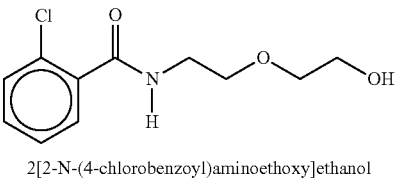
2[2-N-(4-chlorobenzoyl)aminoethoxy]ethanol
146

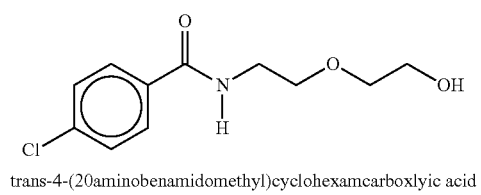
trans-4-(20aminobenamidomethyl)cyclohexamcarboxlyic acid
147

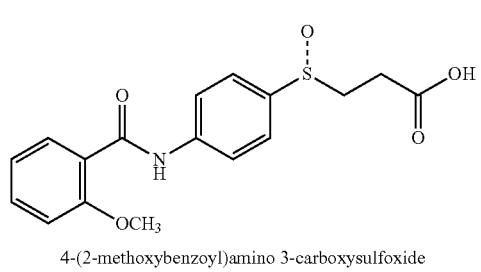
4-(2-methoxybenzoyl)amino 3-carboxysulfoxide
148

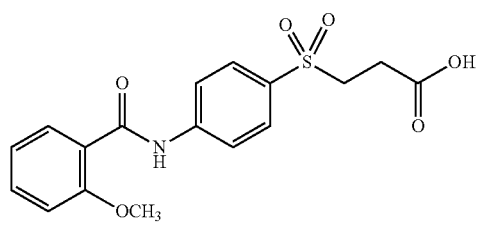
4-(2-methoxybenzoyl)amino 3-carboxypropylsulfone
149

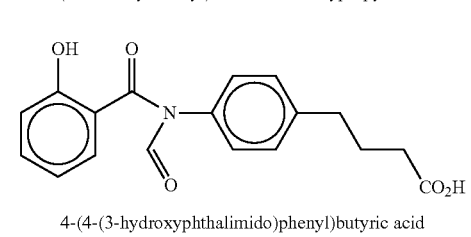
4-(4-(3-hydroxyphthalimido)phenyl)butyric acid
150

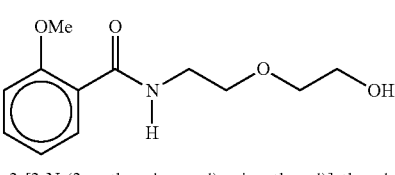
2-[2-N-(2-methoxybenzoyl)aminoethoxyl)]ethanol
151

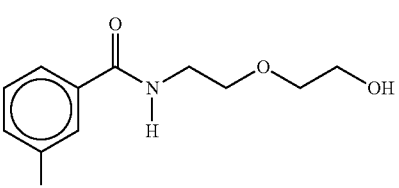
2-[2-N-(3-chlorobenzoyl)aminoethoxyl)]ethanol
152

153

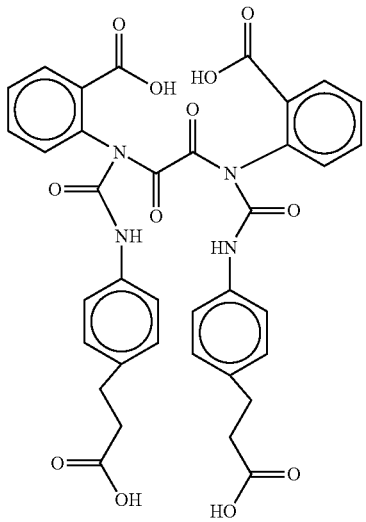

Bis(N-2-carboxyphenyl-N-(N'-3(4-aminophenyl)
propionic acid)ureal)oxaylyl diamide

154

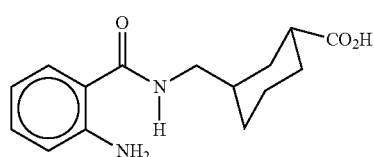

11-N-(3,5-dichloro-2-hdyroxybenzoyl)
aminoudecanoic acid

155

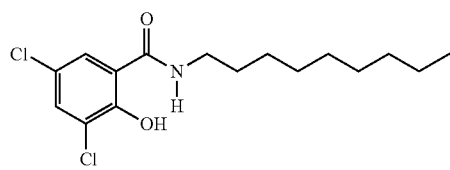

2-[N-(2-bromobenzoyl)aminoethoxy]ethanol

156

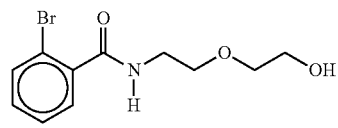

7-N-(3,5-dichloro-2-hydroxybenzoyl)
aminoheptanoic acid

157

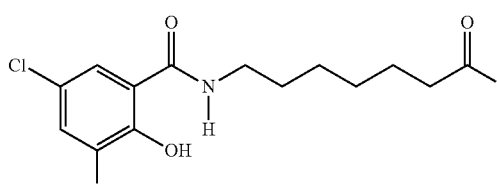

7-N-(3,5-dichloro-2-hydroxybenzoyl)aminoheptanoic acid

158

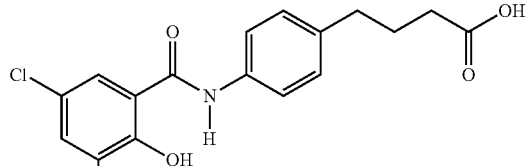

N-[3,5-dichloro-2-hydroxybenzoyl-4(4-aminophenyl)butyric acid

159

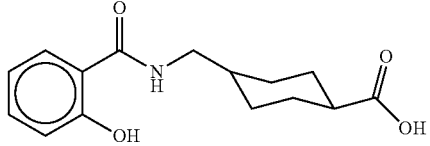

Trans-4-(N-salicyloylaminomethyl)cyclohexane carboxylic acid

160

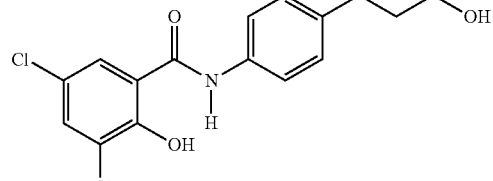

N-[3,5-dichloro-2-hydroxybenzoyl-3-(4-aminophenyl)]propionic acid

161

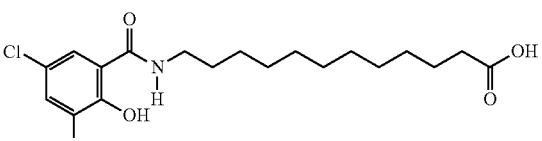

12-N-(3,5-dichloro-2-hydroxybenzoyl)aminododecanoic acid

162

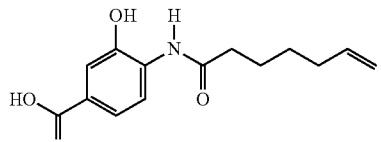

N-(2-hydroxy-4-carboxyl-6-heptenamide

163

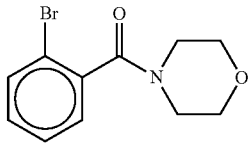

N-(2-bromobenzoyl)morpholine

164

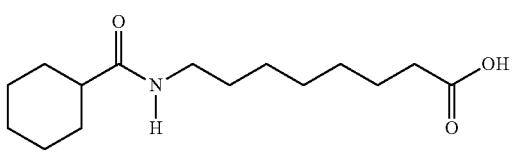

8-N-cyclohexanoylaminocaprylic acid

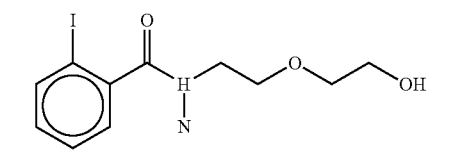

165

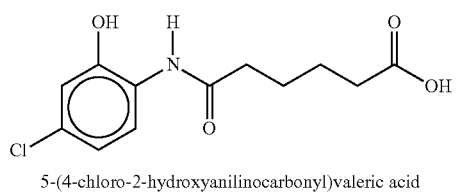

166

5-(4-chloro-2-hydroxyanilinocarbonyl)valeric acid

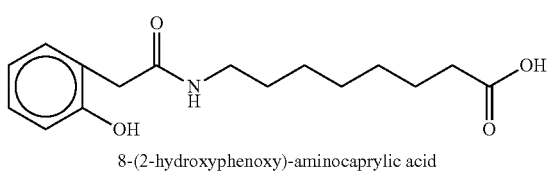

167

8-(2-hydroxyphenoxy)-aminocaprylic acid

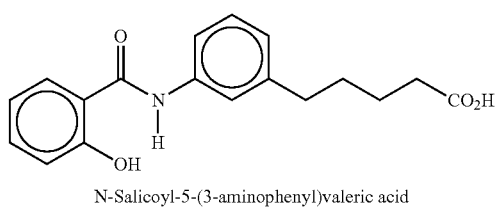

168

N-Salicoyl-5-(3-aminophenyl)valeric acid

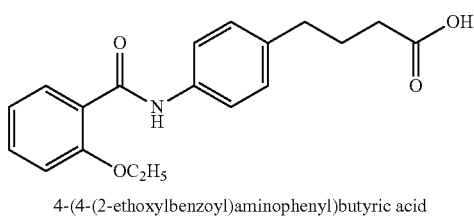

169

4-(4-(2-ethoxylbenzoyl)aminophenyl)butyric acid

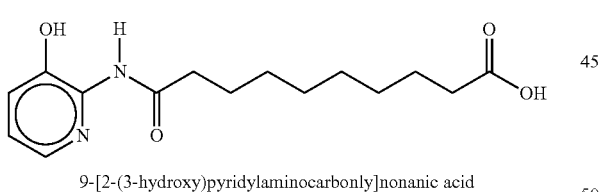

170

9-[2-(3-hydroxy)pyridylaminocarbonly]nonanic acid

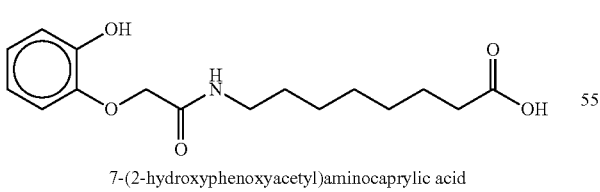

171

7-(2-hydroxyphenoxyacetyl)aminocaprylic acid

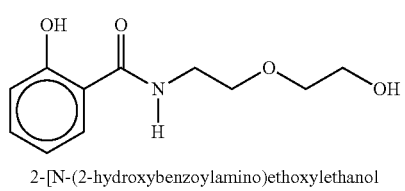

172

2-[N-(2-hydroxybenzoylamino)ethoxylethanol

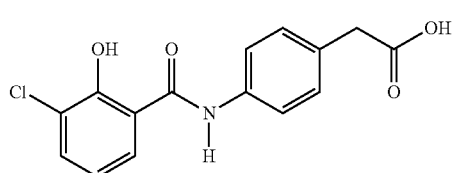

173

4-[N-(3,5-dichloro-2-hydroxybenzoyl)]aminophenylacetic acid

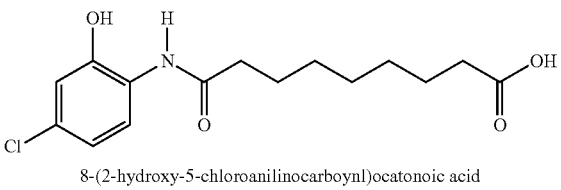

174

8-(2-hydroxy-5-chloroanilinocarboynl)ocatonoic acid

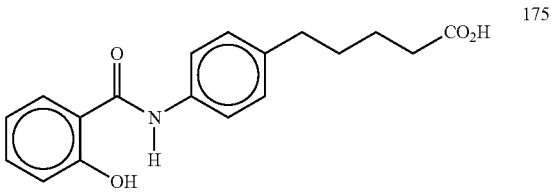

175

N-salicoyl-5-4-(4-aminophentyl)valeric acid

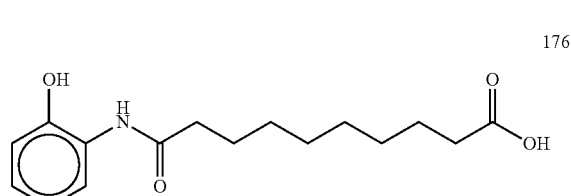

176

9-(2-hydroxy-5-methylanilinocarbonyl)nonanoic acid

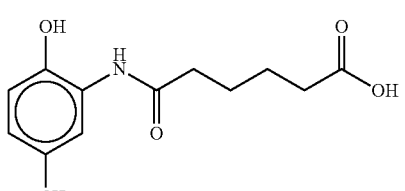

177

5-(2-hydroxy-5-methylanilinocarbonyl)valeric acicd

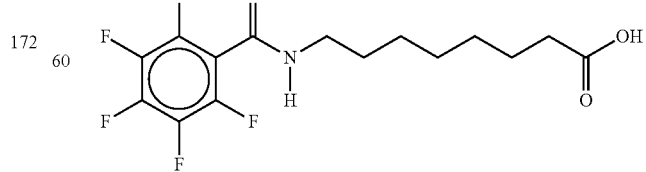

178

8-(pentafluorobenzoyl)aminocaprylic acid

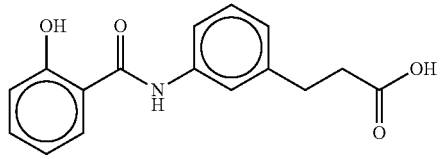
3-(3-(salicyloyl)aminophenyl)propionic acid

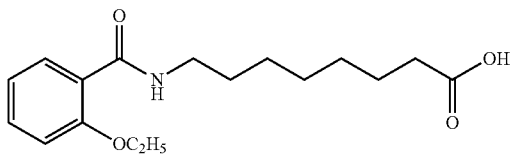
8-(2-ethoxybenzoyl)aminocaprylic acid

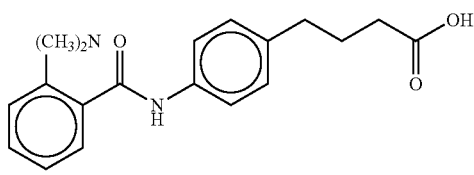
4-(4-(2-Dimethylamino benzoic)aminophenyl)butyric acid

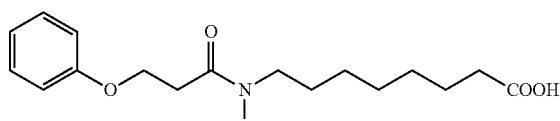
8-(3-Phenoxylpropionylamino)caprylic acid

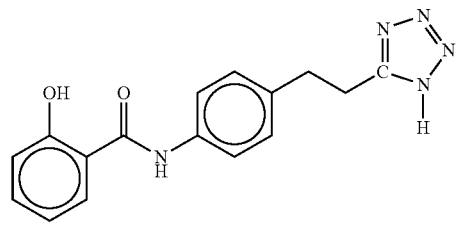
4-(Salicyloyl)aminophenylethyltetrazole

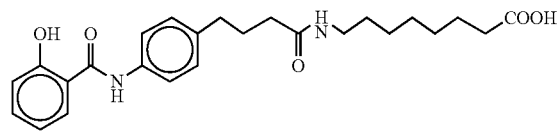
8-(-(4(N-Saliciloyl-4-aminophenyl)butyric)aminocaprylic acid [sic]

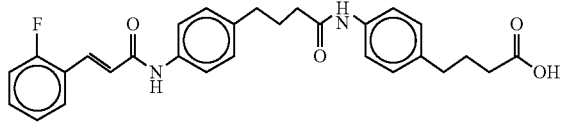
4-(4-(N-(2-Fluorocinnamoyl))aminophenyl)butyric

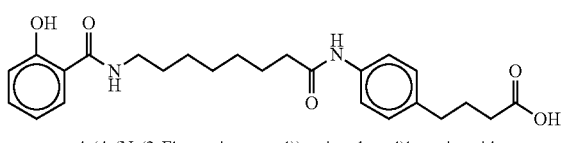
4-(4-(N-(2-Fluorocinnamoyl))aminophenyl)butyric acid

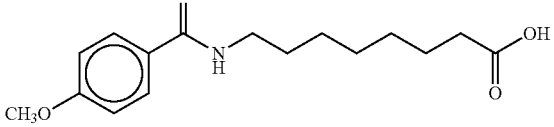
8-(p-anisoyl)aminocaprylic acid

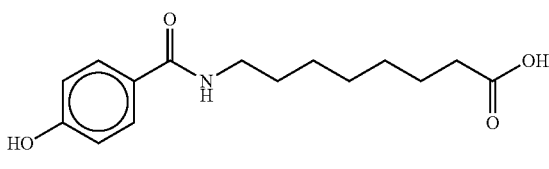
8-(4-Hydroxybenzoyl)aminocaprylic acid

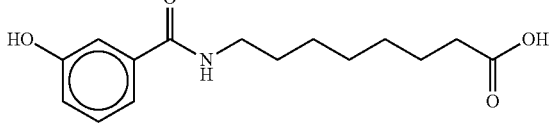
8-(3-Hydroxybenzoyl)aminocaprylic acid

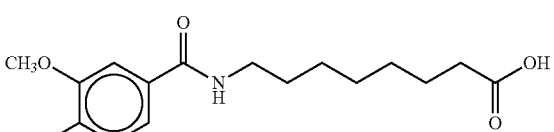
8-(3,4,5-Trimethoxybenzoyl)aminocaprylic acid

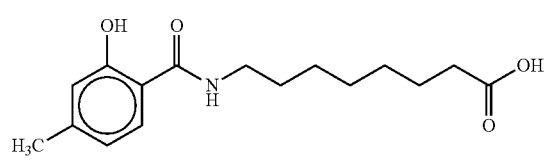
8(-N-4-Methylsalicloyl)aminocarpillic acid [sic]

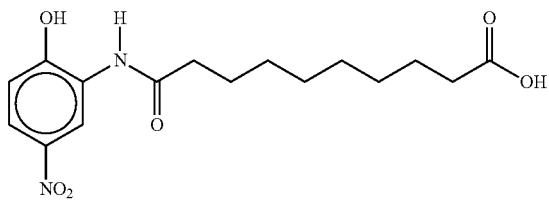
N-10-(2-hydroxy-5-nitroanilino)decanoic acid

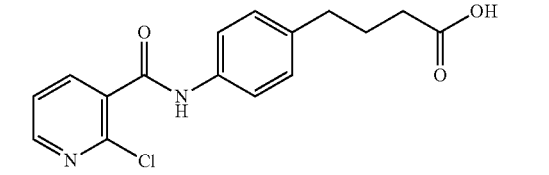
4-(4-(2-chloricotinoyl)aminophenyl)butyric acid and a salt of any of the foregoing.

* * * * *